(12) United States Patent
Tsai et al.

(10) Patent No.: US 10,920,272 B2
(45) Date of Patent: Feb. 16, 2021

(54) HIGH-THROUGHPUT METHOD FOR CHARACTERIZING THE GENOME-WIDE ACTIVITY OF EDITING NUCLEASES IN VITRO

(71) Applicant: St. Jude Children's Research Hospital, Inc., Memphis, TN (US)

(72) Inventors: Shengdar Q. Tsai, Memphis, TN (US); Cicera R. Lazzarotto, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 16/695,719

(22) Filed: Nov. 26, 2019

(65) Prior Publication Data

US 2020/0115750 A1 Apr. 16, 2020

Related U.S. Application Data

(63) Continuation of application No. PCT/US2019/031673, filed on May 10, 2019.

(60) Provisional application No. 62/669,603, filed on May 10, 2018, provisional application No. 62/797,664, filed on Jan. 28, 2019.

(51) Int. Cl.
*C12Q 1/6874* (2018.01)
*C12N 15/10* (2006.01)
*C40B 50/06* (2006.01)

(52) U.S. Cl.
CPC ........ *C12Q 1/6874* (2013.01); *C12N 15/102* (2013.01); *C12N 15/1065* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 5,965,443 A | 10/1999 | Reznikoff et al. | |
| 9,458,453 B2* | 10/2016 | Firnberg et al. | ....... C07H 21/04 |
| 9,822,407 B2 | 11/2017 | Joung et al. | |
| 9,850,484 B2 | 12/2017 | Joung et al. | |
| 2013/0202605 A1 | 8/2013 | Asmus et al. | |
| 2013/0203605 A1* | 8/2013 | Shendure et al. | . C12N 15/1093 506/2 |
| 2015/0259743 A1* | 9/2015 | Burgess et al. | ...... C12Q 1/6869 506/2 |
| 2015/0376628 A1* | 12/2015 | Schoenherr et al. | ........................ C12N 15/1031 435/91.4 |
| 2017/0088833 A1* | 3/2017 | Joung et al. | ......... C12Q 1/6855 |

OTHER PUBLICATIONS

Cameron et al., "Mapping the genomic landscape of CRISPR-Cas9 cleavage," Nat. Methods 2017, 14(6):600-606, with 3 pages of Supplementary Online Methods, published online May 1, 2017. (Year: 2017).*

(Continued)

*Primary Examiner* — Kaijiang Zhang
(74) *Attorney, Agent, or Firm* — Kacvinsky Daisak Bluni, PLLC

(57) ABSTRACT

The invention relates to a high-throughput method for characterizing the genome-wide activity of editing nucleases in vitro.

21 Claims, 65 Drawing Sheets

Specification includes a Sequence Listing.

(56) References Cited

OTHER PUBLICATIONS

Adey A., 2010, Rapid, low-input, low-bias construction of shotgun fragment libraries by high-density in vitro transposition. Genome Biol 11:R119.
Kia et al., 2017, 'Improved genome sequencing using an engineered transposase', BMC Biotechnology, 17(1):6.
Picelli et al., Genome Research, 2014, 24(12):2033-40.
Reznikoff, WS., 2008, 'Transposon Tn5', Annu Rev Genet 42:269-286.
Tsai et al., 2017, 'CIRCLE-seq: a highly sensitive in vitro screen for genome-wide CRISPR-Cas9 nuclease off-targets', Nat. Methods 14(6):607-614.
Tsai et al., 2015, 'GUIDE-seq Enables Genome-Wide Profiling of Off-Target Cleavage by CRISPR-Cas Nucleases', Nature Biotechnology 33(2):187-197.
International Search Report dated Aug. 7, 2019, in corresponding International patent application No. PCT/US19/31673 four (4) sheets.
International Search Report and Written Opinion for the International Patent Application No. PCT/US19/31673, dated Aug. 7, 2019, 9 pages.
Lazzaroto et al. Change-Seq Reveals Genetic and Epigenetic Effects on CRISPR-CAS9 Genome-Wide Activity, Nature Biotechnology, (online) www.nature.com/naturebiotechnology, 26 pages.
Lazzaroto et al. Change-Seq Reveals Genetic and Epigenetic Effects on CRISPR-CAS9 Genome-Wide Activity, (Supplementary) Nature Biotechnology, (online) www.nature.com/naturebiotechnology, 20 pages.

* cited by examiner

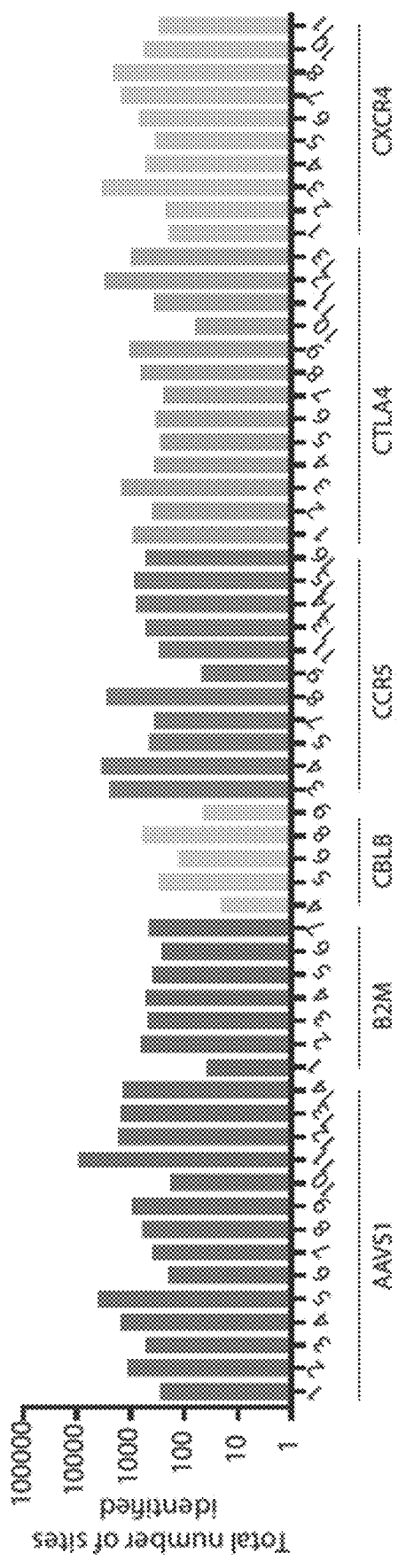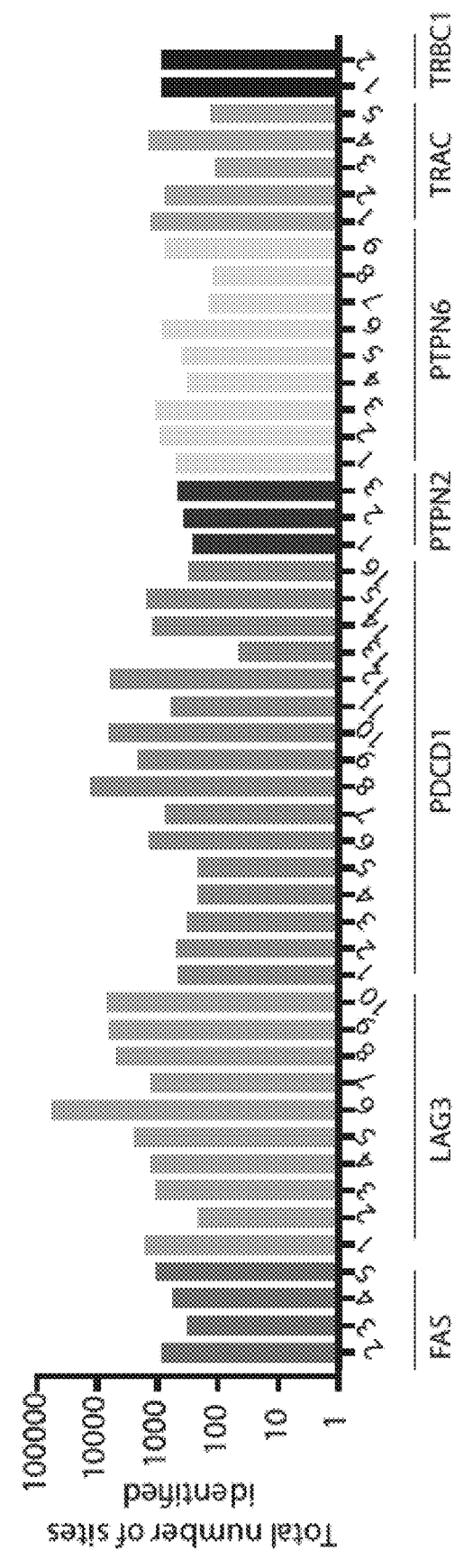
FIG. 11A
FIG. 11B

US 10,920,272 B2

HIGH-THROUGHPUT METHOD FOR CHARACTERIZING THE GENOME-WIDE ACTIVITY OF EDITING NUCLEASES IN VITRO

CROSS-REFERENCE TO RELATED APPLICATIONS

This application is a Continuation of PCT Application No. PCT/US19/03167, filed May 10, 2019, which claims priority to U.S. Provisional Application No. 62/669,603, filed May 10, 2018, and U.S. Provisional Application No. 62/797,664, filed Jan. 28, 2019. The disclosure of all of the foregoing references is herein incorporated by reference in its entirety.

SEQUENCE LISTING

The instant application contains a Sequence Listing which has been submitted electronically in ASCII format and is hereby incorporated by reference in its entirety. Said ASCII copy, created on Nov. 26, 2019, is named 8550_001_SL.txt and is 60,156 bytes in size.

FIELD OF THE INVENTION

The invention relates to a high-Throughput method for characterizing the genome-wide activity of editing nucleases 132 vitro.

BACKGROUND OF THE INVENTION

Genome editing is a transformative, broadly applicable technology for making targeted changes to the genomes of living cells with promise for fundamentally new treatments for human genetic diseases and cancer. However, the safety of these approaches can be difficult to evaluate, because adverse functional consequences of genome editing are not fully understood.

Unintended adverse consequences of therapeutic gene editing can jeopardize promising new therapies. For example, inadvertent activation of proto-oncogenes can predispose to cancer, similar to what was observed with γ-retroviral vectors used in gene therapy for several inherited immunodeficiencies. It is likely critical, therefore, to define potential genotoxic effects of genome editing and biological consequences. Indeed. "off-target" oncogenic mutations can occur at frequencies below the detection thresholds of conventional assays. Taken together, it is important to understand the genome-wide activity of genome editors to define the full spectrum of unintended effects (such as, e.g., off-target mutations) and predict safety.

Significant progress has been made in developing methods to define the genome-wide activity of genome editing nucleases over the past several years. The present inventors have developed Genome-wide Unbiased Identification of Double-stranded breaks Enabled by sequencing (GUIDE-seq), a method for identifying editor-induced off-target mutagenic activity in cells (see FIG. 2) (as described, e.g., in U.S. Pat. No. 9,822,407 and Tsai et al., GUIDE-seq Enables Genome-Wide Profiling of Off-Target Cleavage by CRISPR-Cas Nucleases, Nature Biotechnology, 2014, 187-197, incorporated herein by reference in their entirety). More recently, the present inventors described Circularization for in vitro Reporting of Cleavage Effects by sequencing (CIRCLE-seq), a method for selectively sequencing genomic DNA fragments that can be cleaved by genome editors in vitro (see FIGS. 3A-3B) (as described, e.g., in Tsai et al., CIRCLE-seq: a highly sensitive in vitro screen for genome-wide CRISPR-Cas9 nuclease off-targets, Nat. Methods, 2017, 14, 607-614 and U.S. Pat. No. 9,850,484, both incorporated herein by reference in their entirety). CIRCLE-seq allowed to detect nuclease-induced imitation sites which were previously detected using cell-based methods such as GUIDE-seq as well as many other bona fide nuclease-induced mutation sites. However, CIRCLE-seq has limitations including high DNA input requirements, labor-intensive processing steps, and requirement for specialized equipment for random physical DNA shearing.

SUMMARY OF THE INVENTION

As specified in the Background Section, there is a great need in the art to develop new high-throughput methods that can define side effects of genome editing as comprehensively as possible to advance the development of safe and effective therapies. The present invention addresses this and other needs by providing CHANGE-seq (CIRCLE-seq high-throughput automatable interrogation of global editing by sequencing) which is a high-throughput method for characterizing the genome-wide activity of editing nucleases in vitro.

Specifically, in one aspect, the invention provides a method of preparing a library of covalently closed circular double-stranded DNA (dsDNA) molecules, the method comprising: a) providing a sample comprising dsDNA; b) performing a tagmentation of the dsDNA by incubating the dsDNA with a transposome complex comprising a transposase and a transposon DNA to add sequences that enable circularization; c) gap-repairing single-stranded DNA (ssDNA) gaps in the DNA molecules generated in step (b); d) treating the repaired dsDNA molecules to produce staggered DNA ends that can mediate intramolecular circularization; e) incubating the DNA molecules obtained in step (d) with a ligase to induce intramolecular ligation, and f) treating circularized DNA molecules obtained in step (e) with exonuclease(s) to produce a library of covalently closed circular dsDNA molecules.

In a related aspect, the invention provides a method of preparing a library of covalently closed circular double-stranded DNA (dsDNA) molecules, the method comprising: a) providing a sample comprising dsDNA; b) performing a tagmentation of the dsDNA by incubating the dsDNA with a transposome complex comprising a transposase and a transposon DNA to provide a population of dsDNA molecules; c) gap-repairing single-stranded DNA (ssDNA) gaps in the DNA molecules generated in step (b) by treating said DNA molecules with an uracil-tolerant proofreading polymerase; d) treating the repaired DNA molecules with (i) an uracil-specific excision reagent (USER) to remove uracil and (ii) a polynucleotide kinase (PNK) to prepare staggered ends for ligation; e) incubating the DNA molecules obtained in step (d) with a ligase to induce intramolecular ligation and circularize the DNA molecules, and f) treating the circularized DNA molecules obtained in step (e) with an exonuclease to degrade any remaining linear molecules with unligated ends, to produce a library of covalently closed circular dsDNA molecules.

In one embodiment of any of the above methods, the transposon DNA used in step (b) comprises a 19-bp DNA sequence required for transposition and a 4-8 bp sequence for generating an overhang.

In one embodiment of any of the above methods, one strand of the transposon DNA comprises a uracil base which can be excised by the uracil-specific excision reagent (USER) to generate an overhang.

In one embodiment of any of the above methods, the transposon DNA comprises the sequence /5Phos/ACG/ideoxyU/AGATGTGTATAAGAGACAG (SEQ ID NO: 1) or the sequence /5Phos/CTGTCTCTTATACACATCTACGT (SEQ ID NO: 2), wherein /5Phos/indicates 5' phosphorylation and /ideoxyU/ indicates internal dexoyUridine.

In one embodiment of any of the above methods, the transposase used in step (b) is Tn5 transposase or an active mutant or variant thereof. In one specific embodiment, the Tn5 mutant comprises one or more mutations selected from E54K (as described, e.g., in U.S. Pat. No. 5,965,443, which is incorporated herein by reference in its entirety), L372P (as described, e.g., in U.S. Pat. No. 5,965,443), K212R (as described, e.g., in Kia et al., BMC Biotechnology, 2017, 17(1):6, which is incorporated herein by reference in its entirety), P214R (as described, e.g., in Kia et al., BMC Biotechnology, 2017, 17(1):6), G251R (as described. e.g., in Kia et al., BMC Biotechnology, 2017, 17(1):6), and A338V (as described, e.g., in Kia et al., BMC Biotechnology, 2017, 17(1):6). In one specific embodiment, the Tn5 mutant is Tn5-059 (as described, e.g., in Kia et al., BMC Biotechnology, 2017, 17(1):6).

In one embodiment of any of the above methods, the transposase used in step (b) is mu transposase or an active mutant or variant thereof.

In one embodiment of any of the above methods, the uracil-tolerant proofreading polymerase used in step (c) is Kapa Hifi Uracil+DNA Polymerase.

In one embodiment of any of the above methods, step (c) comprises treating said DNA molecules simultaneously with both (i) an uracil-tolerant proofreading polymerase and (ii) a ligase. In one specific embodiment, the ligase is thermostable. In one specific embodiment, the ligase is Taq ligase.

In one embodiment of any of the above methods, the uracil-specific excision reagent (USER) used in step (d)(i) comprises Uracil DNA glycosylase (UDG) and DNA glycosylase-lyase Endonuclease VIII.

In one embodiment of any of the above methods, the polynucleotide kinase (PNK) used in step (d)(ii) is T4 PNK.

In one embodiment of any of the above methods, the DNA ligase in step (e) is T4 DNA ligase.

In one embodiment of any of the above methods, the ligase in step (e) is used at concentrations optimal for intramolecular ligation.

In one embodiment of any of the above methods, DNA concentrations in step (e) is 2.5-5 ng/μl.

In one embodiment of any of the above methods, the exonuclease used in step (f) is selected from ATP-dependent DNase, *E. coli* exonuclease I, Lambda exonuclease, T5 exonuclease, T7 exonuclease, and any combination thereof.

In one embodiment of any of the above methods, step (f) comprises treating the circularized DNA molecules obtained in step (e) with at least one additional exonuclease, and wherein treatments with the first exonuclease and the additional exonuclease can be performed either simultaneously or sequentially. In one specific embodiment, the at least one additional exonuclease is selected from plasmid-safe ATP-dependent exonuclease, Lambda exonuclease, and *E. coli* Exo I.

In one embodiment of any of the above methods, the dsDNA in step (a) is genomic DNA (gDNA) or synthetic DNA. In one specific embodiment, the gDNA is human gDNA.

In one embodiment of any of the above methods, the method further comprises: g) contacting the library of covalently closed circular dsDNA molecules with a genome editing enzyme to induce a site-specific cleavage; h) preparing the cleaved fragments for end-ligation; i) ligating a sequencing adapter, at the cleavage site; j) contacting the library with enzymes that nick at the deoxyuridine; and k) sequencing resulting fragments using primers that bind to the sequencing adapter.

In one embodiment, the genome editing enzyme causes a genome modification that could be converted using an in vitro reaction into a double-stranded break.

In one embodiment, the genome editing enzyme cleaves at on- and/or off-target sites.

In one embodiment, the genome editing enzyme induces blunt or staggered/overhanging ends.

In one embodiment, the genome editing enzyme is selected from genome editing nucleases, base editor proteins and Cas9 nickases.

In one embodiment, the genome editing enzyme is selected from meganucleases, MegaTALs, zinc-finger nucleases (ZFNs), transcription activator effector-like nucleases (TALEN), Clustered Regularly Interspaced Short Palindromic Repeats (CRISPR)/Cas RNA-guided nucleases (CRISPR/Cas RGNs), FokI-dCas9 fusion proteins, fusions of CRISPR/Cas9 and a cytidine deaminase enzyme, and base editors including cytosine base editors (CBEs) and adenine base editors (ABEs).

In one embodiment, the genome editing enzyme is selected from Cas9, Cas12a (Cpf1), CasX, CasY, C2C2, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cu1966, and homologs or modified versions thereof.

In one embodiment, the genome editing enzyme is complexed with a specific guide RNA (gRNA).

In one embodiment, preparing the cleaved fragments for end-ligation in step (h) comprises A-tailing the dsDNA molecules to prevent dsDNA molecule concatemerization.

In one embodiment, preparing the cleaved fragments for end-ligation in step (h) comprises treating the cleaved fragments with a proteinase K (PK).

In one embodiment, the sequencing adapter in step (i) comprises at least a single deoxyuridine and a primer site compatible for use in PCR priming or sequencing. In one specific embodiment, the primer site comprises a next generation sequencing primer binding sequence, a randomized DNA barcode, or unique molecular identifier (UMI).

In one embodiment, the sequencing adapter comprises: a first region; a second region that forms one or more hairpin loops and comprises a primer site compatible for use in PCR priming and/or sequencing; a third region that is complementary to the first region with one additional nucleotide; and wherein the single deoxyuridine is between the second and third regions. In one specific embodiment, the method further comprises: contacting the library with one or more enzymes to nick at the deoxyuridine in the sequencing adapter; using PCR amplification to enrich for adapter-ligated fragments and to add a full sequencing adapter, and sequencing those fragments bearing a sequencing adapter. In one specific embodiment, the one or more enzymes to nick at the deoxyuridine comprise uracil DNA glycosylase (UDG) and/or endonuclease VIII.

In one embodiment, the sequencing adapter does not form hairpin loops.

In one embodiment, the genome editing enzyme is an enzyme that leaves staggered DNA ends, and wherein the method comprises an end-repair step after cleavage of the library of covalently closed circular dsDNA molecules. In one specific embodiment, the genome editing enzyme is selected from Cpf1, ZFNs, TALENs, meganucleases, megaTALs, and dimeric RNA-guided FokI-dCas9 nucleases.

In one embodiment, the genome editing enzyme is a base editor protein, and the method comprises treating the library of covalently closed circular dsDNA molecules with the base editor protein and an additional enzyme that can introduce a break at the site of deaminated bases. In one specific embodiment, the base editor protein is a C→T base editor, and the method comprises treating the base edited dsDNA molecules with an uracil-specific excision reagent (USER). In one specific embodiment, the USER comprises Uracil DNA glycosylase (UDG) and DNA glycosylase-lyase Endonuclease VIII. In one specific embodiment, the base editor protein is a A→G base editor, and the method comprises treating the base edited dsDNA molecules with endonuclease V.

In a related aspect, the invention provides a method for characterizing a genome-wide activity of a genome editing enzyme, the method comprising the steps of any one of the above methods. In one specific embodiment, the genome-wide activity includes unintended off-target activity.

In another aspect, the invention provides a method for determining which of a plurality of genome editing nucleases is the most specific, said method comprising the steps of any one of the above methods.

In yet another aspect, the invention provides a method for generating a patient-specific profile of genome-wide activity of a genome editing enzyme, the method comprising the steps of any one of the above methods.

In a further aspect, the invention provides kits for use in the methods of the invention. The kits can include, for example, one or more of the following components: a transposase, a custom transposon DNA, an uracil-tolerant proofreading polymerase, an uracil-specific excision reagent (USER) (e.g., Uracil DNA glycosylase (UDG) and DNA glycosylase-lyase Endonuclease VIII), a polynucleotide kinase (PNK), a ligase, an exonuclease, a genome editing enzyme (e.g., Cas9 protein), a guide RNA (e.g., a control gRNA), a gDNA template (e.g., a control gDNA template), a sequencing adapter, primers that bind to the sequencing adapter, and/or a container, and/or instructions for use in any one or more methods described herein.

These and other aspects of the present invention will be apparent to those of ordinary skill in the art in the following description, claims and drawings.

BRIEF DESCRIPTION OF THE DRAWINGS

(FIG. 1A) Schematic of CHANGE-seq method which reduces cell genomic DNA input requirement, processing time and steps, and cost compared to standard CIRCLE-seq, and substantially increases scalability. The shown embodiment of the method comprises efficient genomic DNA (gDNA) circularization using Tn5-transposon based tagmentation, followed by in vitro cleavage with Cas9 ribonucleoprotein complex, adapter ligation, PCR, and high-throughput sequencing. (FIG. 1B) Manhattan plots of position and frequency of in vitro off-target activity (raw read count) detected by CHANGE-seq for 8 sites targeted against human CCR5, PDCD1, and TRAC locus. Arrow indicates intended on-target site. (FIG. 1C) Manhattan plots of position and frequency of in vitro off-target activity (normalized read count) detected by CHANGE-seq for 8 sites targeted against human CCR5, PDCD1, and TRAC locus. Arrow indicates intended on-target site. (FIG. 1D) Sequence logos summarizing the weighted frequency of bases at genomic off-target sites. (FIG. 1E) Visualization of CHANGE-seq output for TRAC site #1 (SEQ ID NOS 3-18, respectively, in order of appearance) and CCR5 site #3 (SEQ ID NOS 19-34, respectively, in order of appearance). Each row is an off-target site where mismatches relative to the intended target are marked with boxed nucleotides (A, C, G, or T). (FIG. 1F) Barplot of numbers of off-target sites detected by CHANGE-seq method at 8 sites tested at PDCD1, TRAC locus, and CCR5.

(FIG. 3A) Schematic of CIRCLE-seq used for selective sequencing of Cas9-cleaved genomic DNA (gDNA). DNA circularized using a novel restriction-enzyme independent method and circularized DNA molecules are enzymatically purified by exonuclease selection. gDNA circles are treated with Cas9, only cleaved, linearized molecules have free ends for adapter-ligation and high-throughput sequencing. (FIG. 3B) Venn diagrams comparing off-target sites detected by CIRCLE-seq and GUIDE-seq. For most sites, CIRCLE-seq detects all sites previously detected by GUIDE-seq as well as many additional bona fide sites of nuclease-induced mutagenesis in cells.

FIG. 4 discloses SEQ ID NOS 1-2, respectively, in order of appearance.

FIG. 9A discloses SEQ ID NOS 77-112, respectively, in order of appearance. FIG. 9B discloses the "pilot" sequences as SEQ ID NOS 113-149 and the "optimized" sequence as SEQ ID NOS 150-186, all respectively, in order of appearance.

FIGS. 11A-11B. Barplot of number of sites detected by CHANGE-seq for 110 Cas9 gRNAs targeted against 13 human genes.

DETAILED DESCRIPTION OF THE INVENTION

Figure 1A:
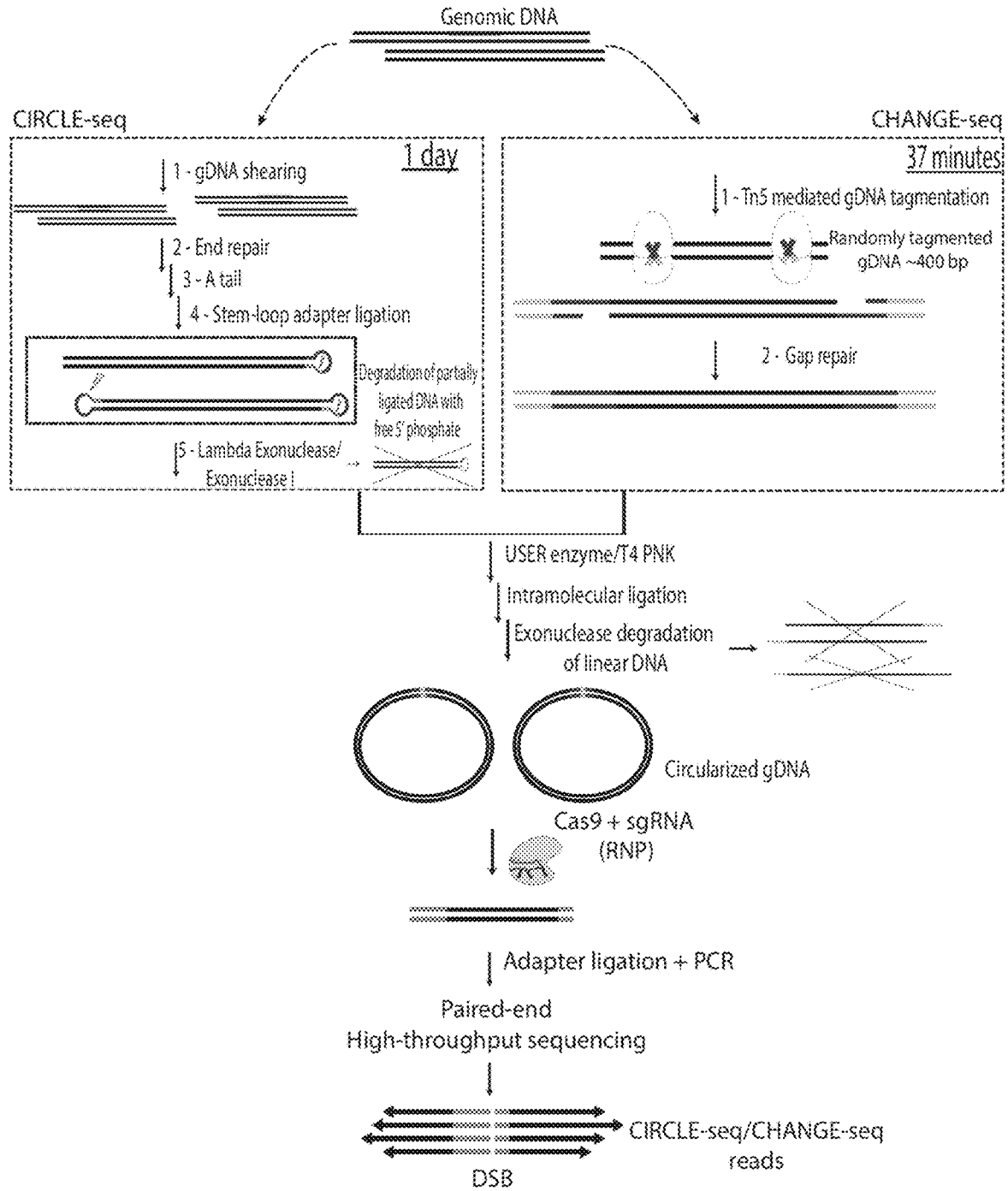
FIGS. 1A-1F. CHANGE-seq method used for high-throughput characterization of therapeutic T-cell targets.
Figure 1B:
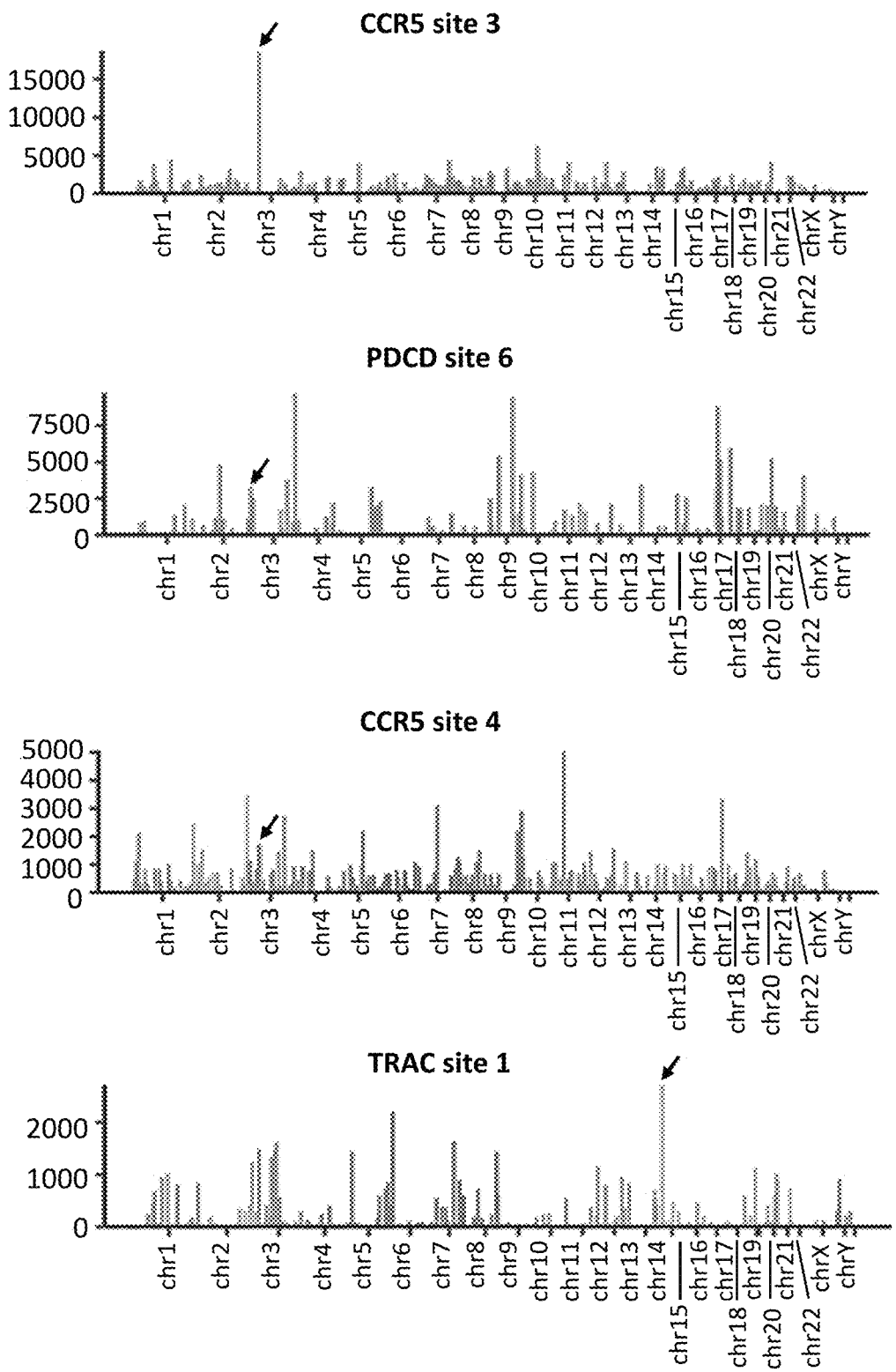
Figure 1C:
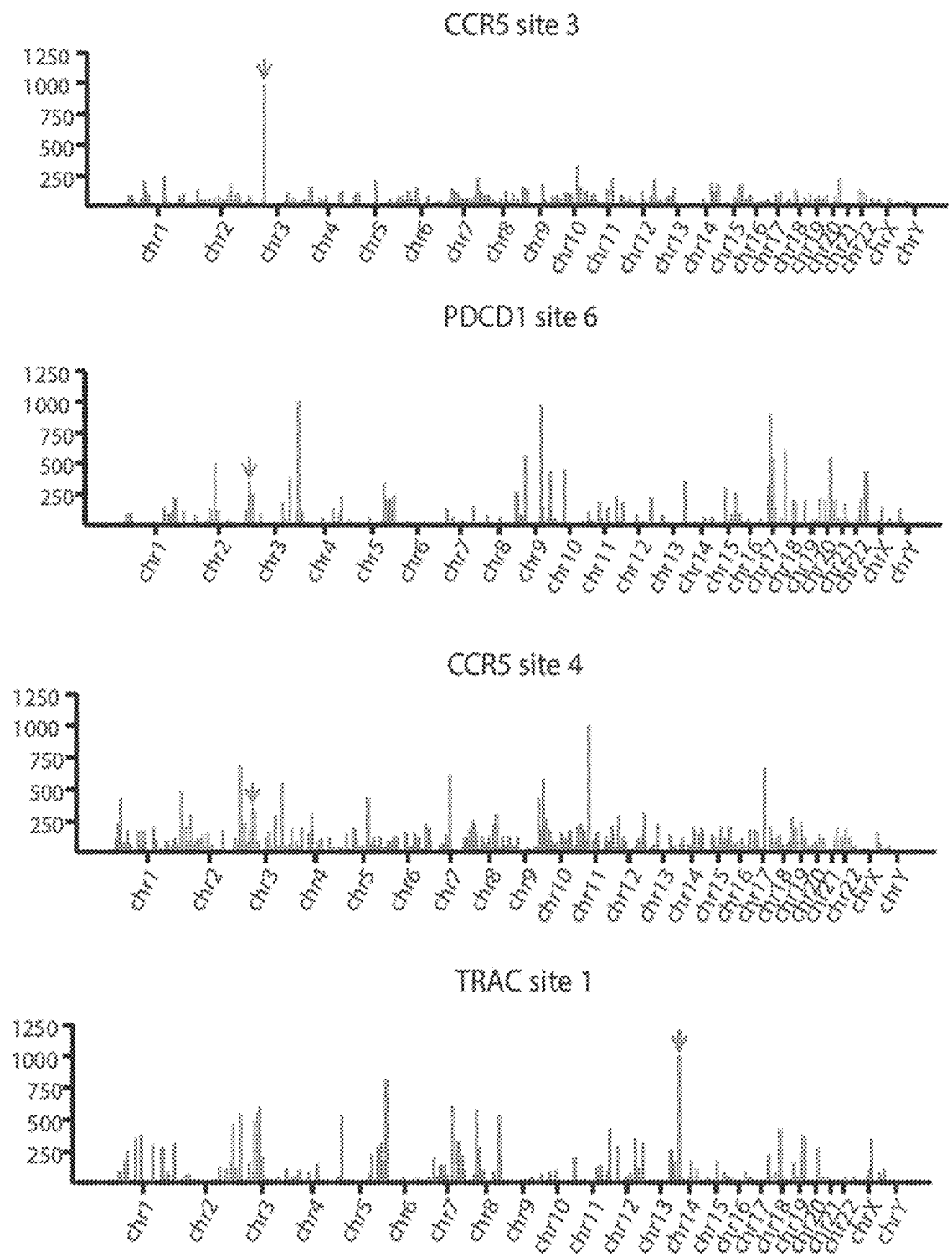
Figure 1D:
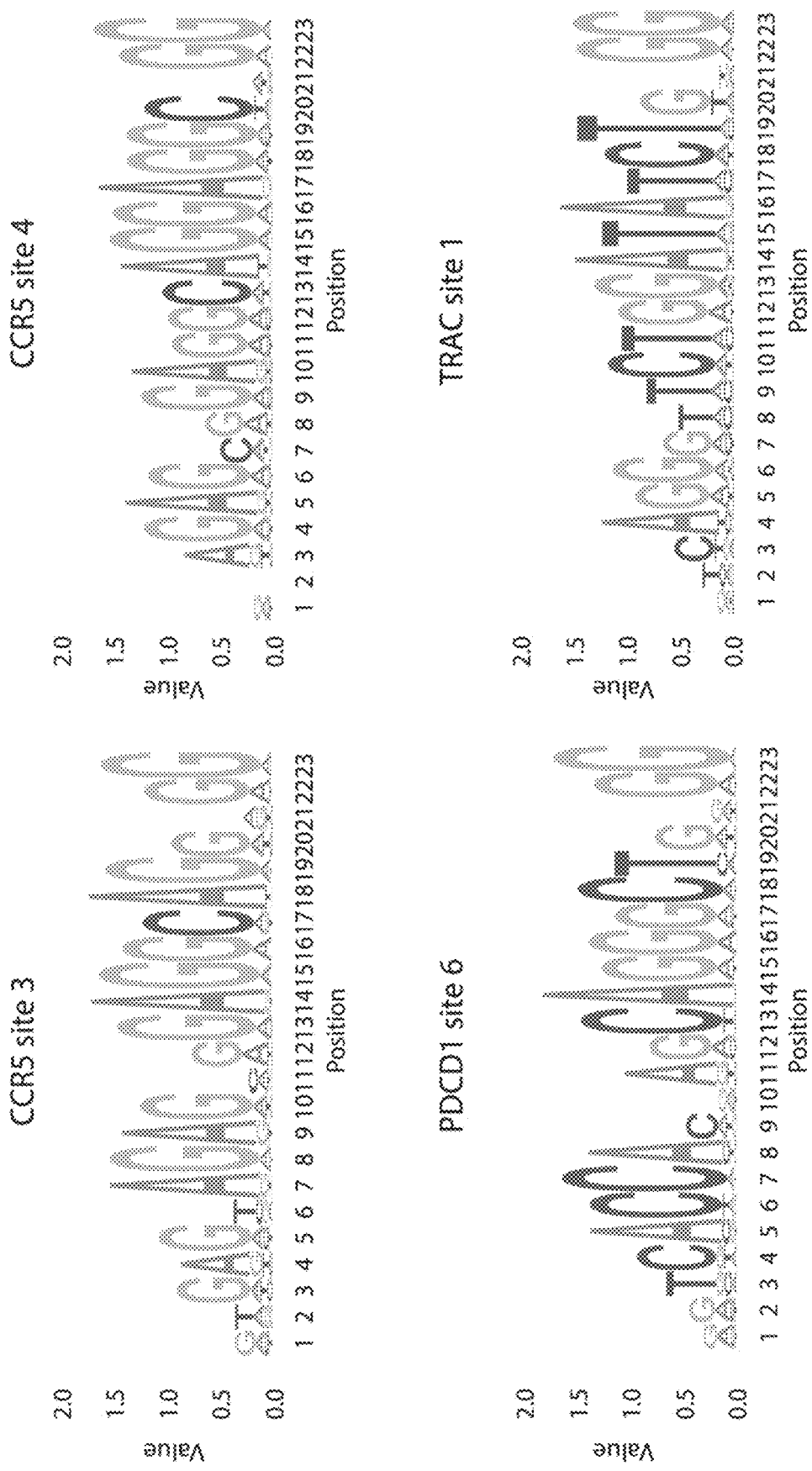
Figure 1E:
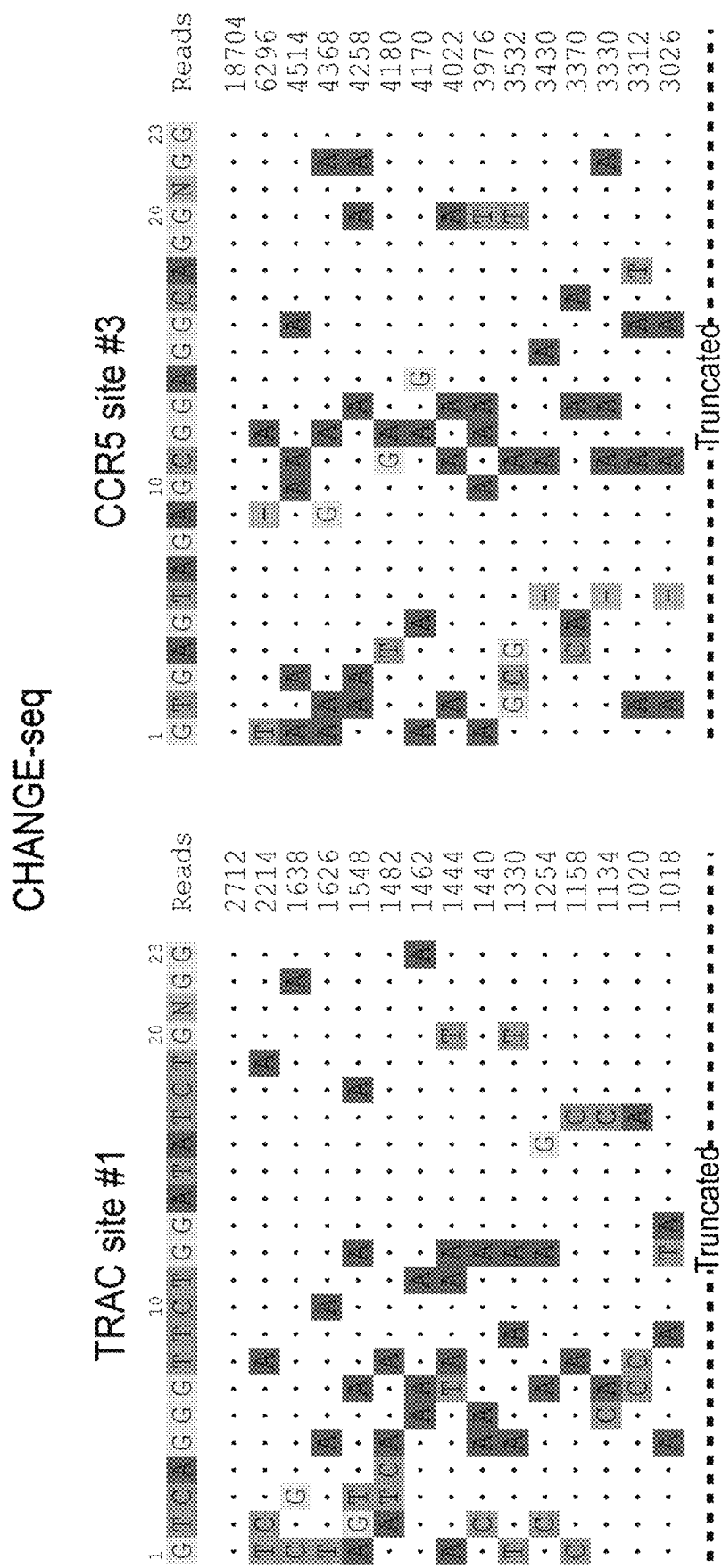
Figure 1F:
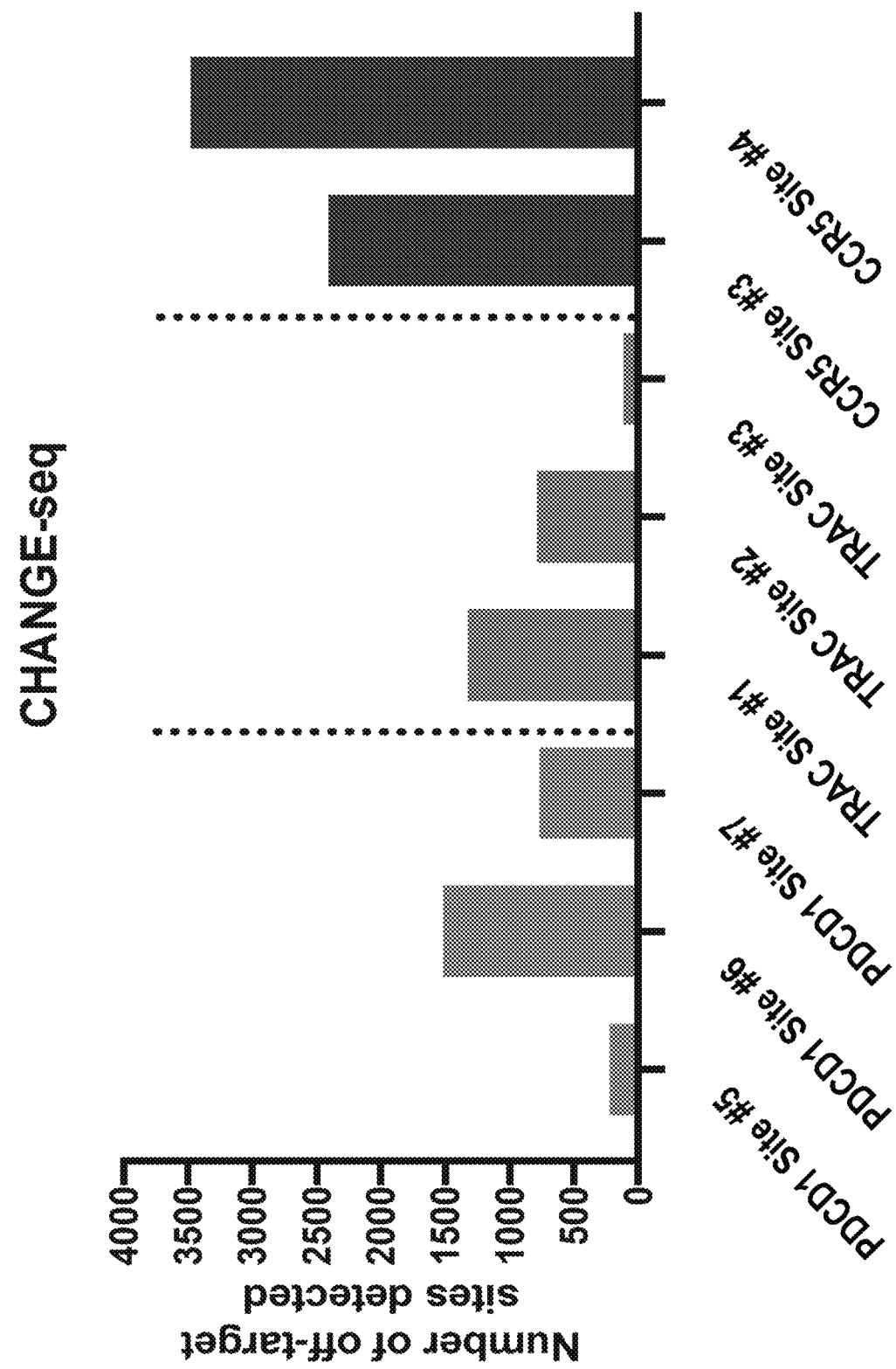
Figure 2:
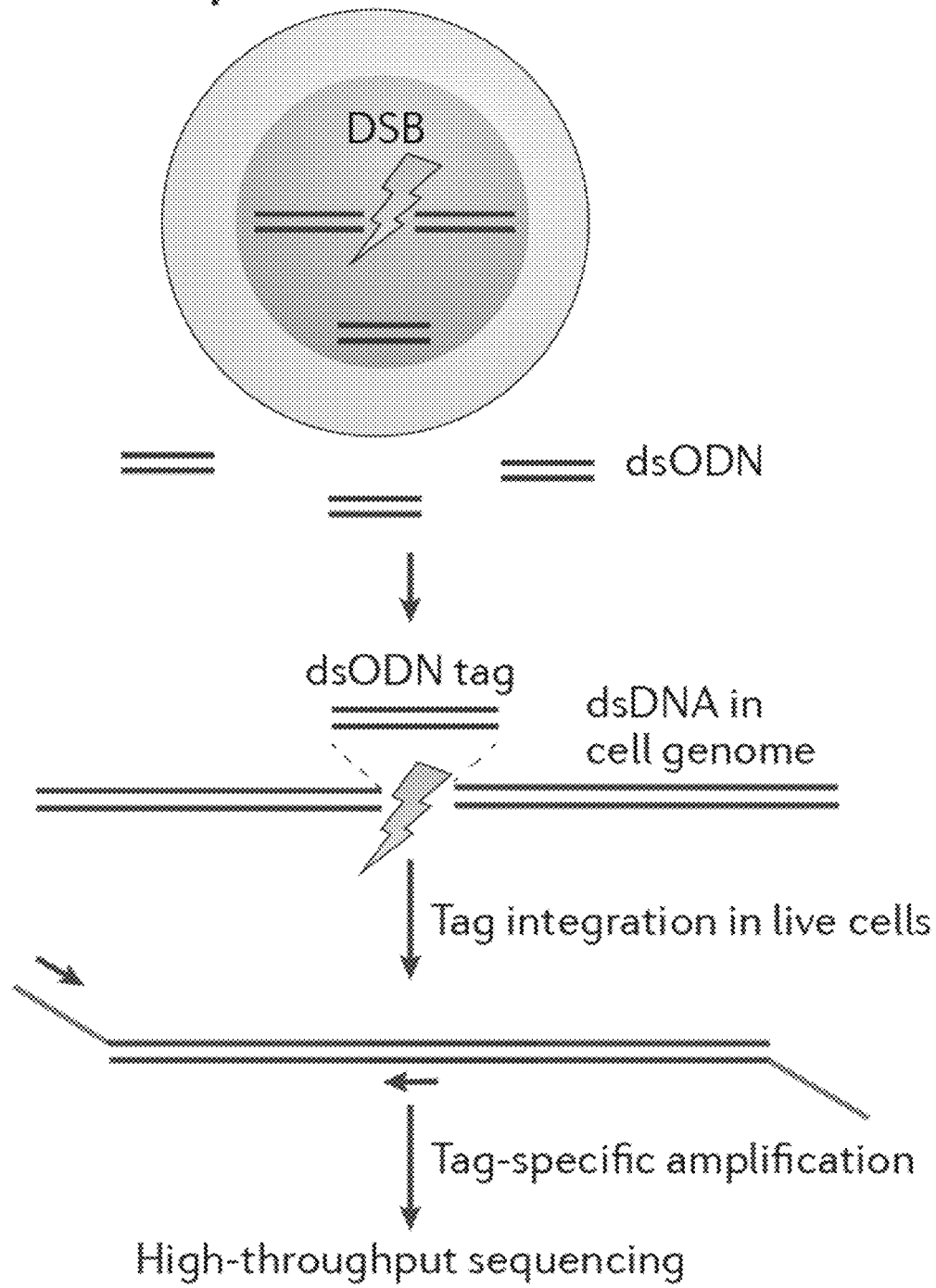
FIG. 2. GUIDE-seq overview. GUIDE-seq is a method to determine the genome-wide nuclease activity of CRISPR-Cas9 in live cells. It is based on the integration of an end-protected short double-stranded oligodeoxynucleotide (dsODN) tag into cellular double stranded breaks (DSBs), followed by tag-specific amplification to amplify genomic flanking regions.
Figure 3A:
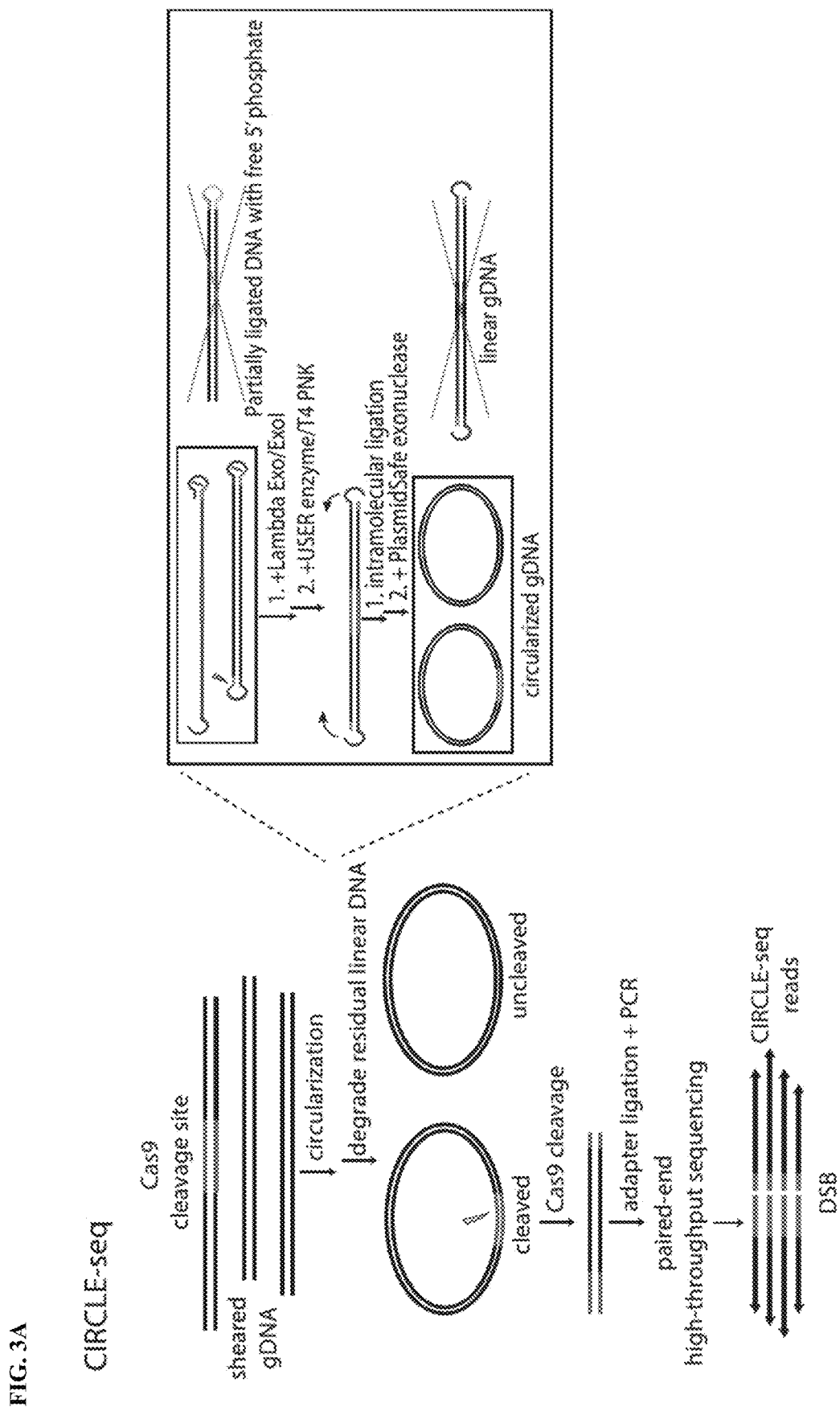
FIGS. 3A-3B. CIRCLE-seq overview.
Figure 3B:
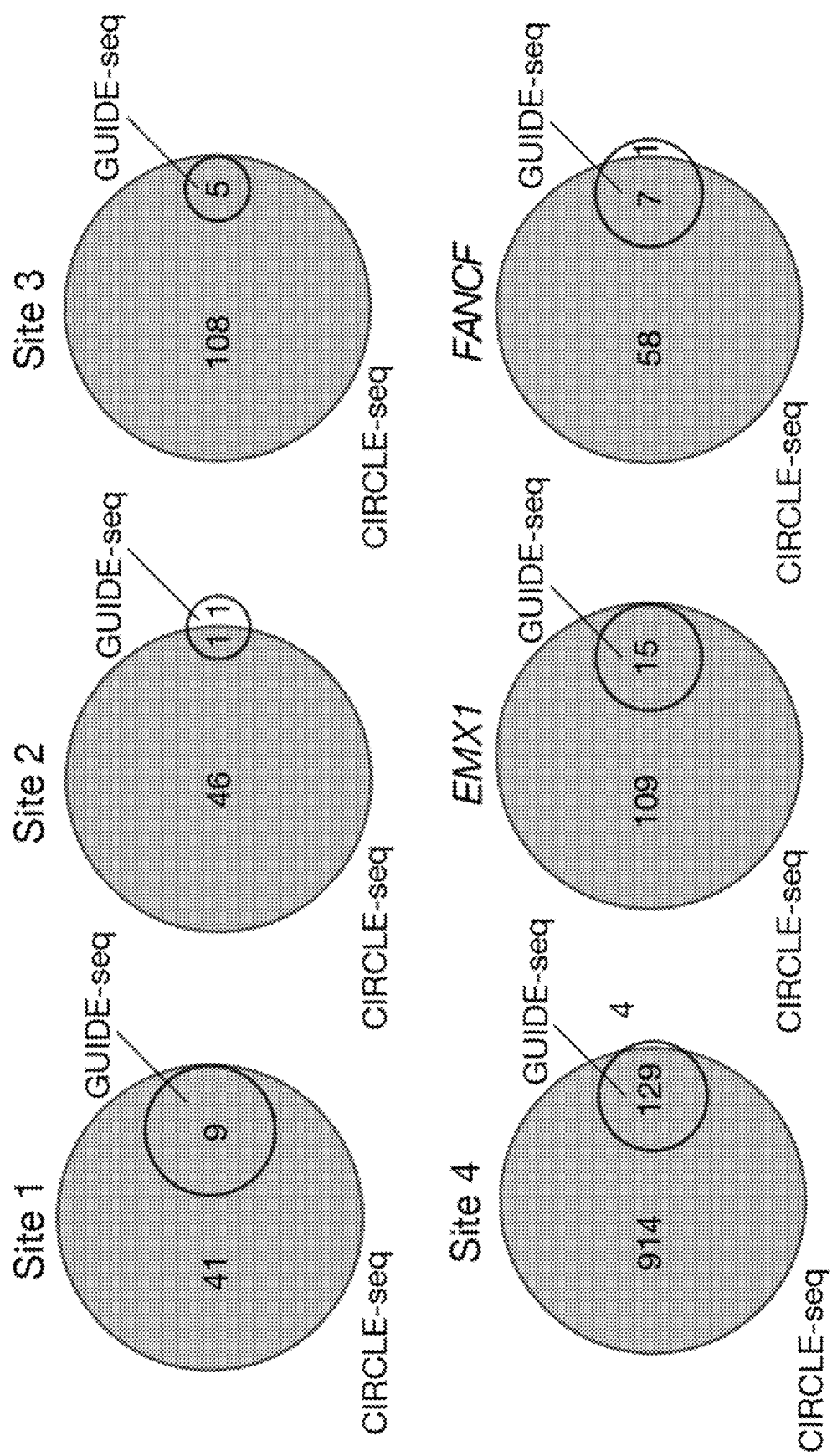
Figure 4:
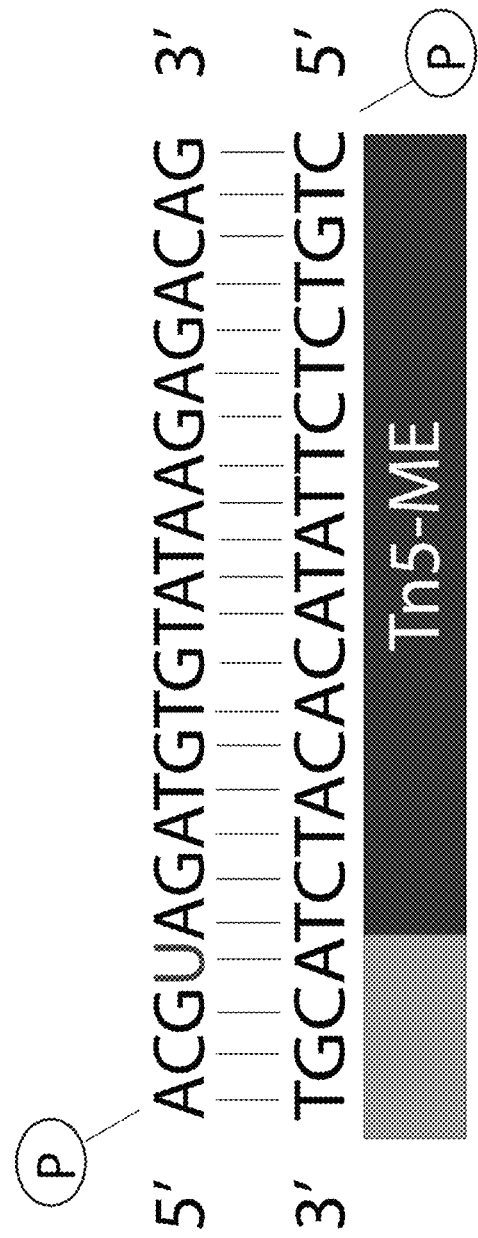
FIG. 4. Composition of the annealed mosaic end double-stranded oligonucleotides used in CHANGE-seq. P denotes phosphorylation, U indicates an internal deoxyUridine base.

The present invention provides CHANGE-seq (CIRCLE-seq high-throughput automatable interrogation of global editing by sequencing; previously referred to informally as CIRCLE-seq-HT) method for high-throughput characterization of the genome-wide activity of editing nucleases in vitro. The broad conception of the CHANGE-seq method is as follows:

1) Tagmentation of DNA, adding sequences that enable circularization;
2) Gap-repairing tagmented DNA to close gaps generated during tagmentation;
3) Treating DNA to produce staggered DNA ends that can mediate efficient intramolecular circularization;
4) Incubating DNA with a ligase at concentrations optimal for intramolecular ligation; and
5) Treating circularized DNA molecules with exonuclease(s) to produce purified, covalently closed dsDNA molecules.

CHANGE-seq method produces a highly purified library of covalently closed circular dsDNA (by degrading non-circular DNA) and allows to overcome limitations of the CIRCLE-seq protocol previously developed by the present inventors (as described, e.g., in Tsai et al. CIRCLE-seq: a highly sensitive in vitro screen for genome-wide CRISPR-Cas9 nuclease off-targets, Nat. Methods, 2017, 14, 607-614 and U.S. Pat. No. 9,850,484, both incorporated herein by reference in their entirety). CHANGE-seq utilizes a new enzymatic workflow for generation of circularized genomic DNA, which involves extensively optimized tagmentation, gap-repair, exonuclease treatment and adapter-ligation steps to achieve higher enrichment levels for nuclease-cleaved DNA and more sites detected than CIRCLE-seq. CHANGE-seq tagmentation-based workflow increases circularization yield and reduces DNA (e.g., genomic DNA) input requirement by approximately 5-fold to about 5 μg and substantially simplifies the prior CIRCLE-seq method by eliminating requirement for physical shearing instrument and nine enzymatic or purification steps. As compared to CIRCLE-seq, CHANGE-seq reduces processing steps, time (e.g., CHANGE-seq simplifies labor-intensive portion of the library preparation from 10 steps taking one day to a single 7-minute step), and cost, while improving scalability, reproducibility and reliability as to the sites detected.

In direct comparisons, the inventors found that CHANGE-seq can achieve comparable or higher levels of enrichment than the original CIRCLE-seq method. CHANGE-seq read counts are strongly correlated with CIRCLE-seq read counts, and the overlap in sites detected by CHANGE-seq and CIRCLE-seq is comparable to the overlap between CIRCLE-seq technical replicates. Using CHANGE-seq, it is now possible to define CRISPR-Cas nuclease (e.g., CRISPR-Cas9) genome editing activity at a scale not previously achievable by CIRCLE-seq.

The CHANGE-seq method involves performing a tagmentation of the dsDNA. In one embodiment, the tagmentation is conducted by incubating the dsDNA with a transposome complex comprised of transposase and transposon DNA to provide a population of dsDNA molecules. In one embodiment, Tn5 transposase (or an active mutant or variant thereof) is used. Tn5 transposase mediates the insertion of DNA associated with short 19-bp mosaic ends (Reznikoff, W S. Transposon Tn5. Annu Rev Genet 42, 269-286 (2008)) and is used for preparations of whole genome sequencing, ATAC-seq, and other genomic sequencing libraries (Adey A. Rapid, low-input, low-bias construction of shotgun fragment libraries by high-density in vitro transposition. Genome Biol 11:R119 (2010)).

In one embodiment of the CHANGE-seq method of the invention, Tn5 transposase and an optimized end-repair/gap-repair/overhang-generation approach is utilized to circularize genomic DNA (gDNA) in a restriction-enzyme independent fashion. The streamlined process is substantially different from the CIRCLE-seq workflow for circularization and eliminates the need for physical shearing of the DNA using a Covaris ultrasonication instrument (See FIG. 1A-1F, FIG. 4). The inventors have optimized the CHANGE-seq method to generate covalently-closed circular DNA and to maximize enrichment for nuclease-cleaved gDNA fragments.

This method can be used to rapidly evaluate the specificity of CRISPR-Cas nucleases for therapeutics, or for any application where it would be beneficial to define the genome-wide activity of editing nucleases in vitro. For example, it can be used to evaluate the relative specificity of different targets against the same gene or genetic element, various nucleases, and formulations. Additionally, it can be used to rapidly generate patient-specific profiles of genome-wide activity.

The CHANGE-seq method has a number of advantages compared to existing technology CIRCLE-seq, such as for example and not limitation:

1. Reduction of the DNA input requirements (e.g., by approximately 5-fold);
2. Reduction of the processing time by approximately 12 hours, eliminating 10 enzymatic or purification steps;
3. Elimination of the requirement for physical shearing of gDNA by sonication requiring specialized instrumentation;
4. Elimination of the possibility of shearing-associated DNA damage confounding results; and
5. Improvement of scalability, enabling testing of more targets, formulations, or sources of gDNA.

The CHANGE-seq methods of the invention can be used to detect unintended effects of editing nucleases to advance the development of safe and effective therapies. For example, the methods of the invention can be used to rapidly analyze the genome-wide activity of a large number of different genome-editing nucleases to determine which are the most specific. The experimental framework disclosed herein can increase confidence in the safety of the next generation of promising genome editing therapies.

Without wishing to be bound by theory, it is suggested that the methods of the present invention can change the paradigm for defining the safety of therapeutic genome editing towards using new high-throughput methods to define the genome-wide activity of genome editors as comprehensively as possible. Ultimately, these methods can have utility for rigorously comparing the safety of novel genome editing methods.

The methods of the invention can be used for assessing the activity of all classes of genome editing nucleases, including, without limitation, meganucleases, zinc finger nucleases (ZFNs), transcription activator effector-like nucleases (TALENs), and CRISPR-Cas RNA-guided nucleases. S. pyogenes Cas9, one of the first discovered and most commonly used RNA-guided nucleases, is a simple-two component system comprised of Cas9 protein and a short associated single guide RNA (gRNA).

The specificity of CRISPR-Cas nucleases can be modulated by gRNA truncation, dimerization, paired nicking, variants engineered by structure-guided design or bacterial selection, and synthetic gRNA modifications. Additionally, CRISPR-Cas nucleases that can function robustly in human cells have been discovered from many other species including Cas9 from *S. aureus, N meningitides*, and Cpf1 from *Acidaminococcus* and *Lachnospiraceae*.

The CHANGE-seq methods described herein can improve confidence in emerging genome editing therapeutic strategies.

The results obtained can be directly applicable to many genome editing strategies that are the subject of intense investigation, such as for example and not limitation, the treatment of HIV or cancer immunotherapy.

Using the approach described herein, the inventors were able to reduce the DNA input requirements (e.g., approximately five-fold), and associated processing time and cost so that the approach can be substantially scaled to interrogate hundreds of target sites or samples.

In accordance with the present invention there may be employed conventional pharmacology and molecular biology techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M J. Gait ed. 1984); *Nucleic Acid Hybridization* (B. D. Hames & S. J. Higgins eds. (1985)); *Transcription and Translation* (B. D. Hames & S. J. Higgins, eds. (1984)); *Animal Cell Culture* (R. I. Freshney, ed. (1986»; *Immobilized Cells and Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994); among others.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Defining Genetic Factors that Govern Genome Editor Activity by Generating Large-Scale In Vitro Genome-Wide Activity Profiles Rationale.

It is hypothesized that there are genetic sequence determinants that govern the cleavage activity of genome editors at a mismatched off-target site. For example, the inventors have observed that G:U wobble base pairings are generally well-tolerated but there may be many other more subtle or position-specific effects that have not yet been detected. In the case of CRISPR-Cas genome editors, these properties may be particularly generalizable, as the targeting specificity is primarily directed by Watson-Crick gRNA:DNA base pairing interactions. It can be easier to first define these genetic determinants in a simpler in vitro context, where activity is not influenced by epigenetic factors like chromatin accessibility.

General rules that govern the genome-wide off-target activity of engineered nucleases are not well understood. Large-scale datasets that characterize genome editing nuclease genome-wide activity do not exist, because the methods have been labor-intensive and require relatively large amounts of cells that make them difficult to scale. High-throughput in vitro genome editing activity profiling might enable the derivation of rules and features that define the biochemical activity of genome editors in the context of human genomic DNA (gDNA).

Experimental Studies.

The inventors have developed a significantly improved method, called CHANGE-seq, that overcomes the bottleneck to generating large-scale genome editor genome-wide activity data. Briefly, the inventors designed and extensively optimized a molecular biology workflow for circularizing human gDNA by use of Tn5 transposition, an enzyme that is now widely used for preparation of whole-genome sequencing and ATAC-seq libraries followed by optimized gap repair and intramolecular ligation. In comparison to the standard CIRCLE-seq method, this method reduces amount of gDNA input requirements by approximately 5-fold, reduces certain labor-intensive processing steps and time from 1 day to 7 minutes, while maintaining excellent correlation in read counts when compared with CIRCLE-seq method (see FIGS. 1A-1F).

Figure 8A:
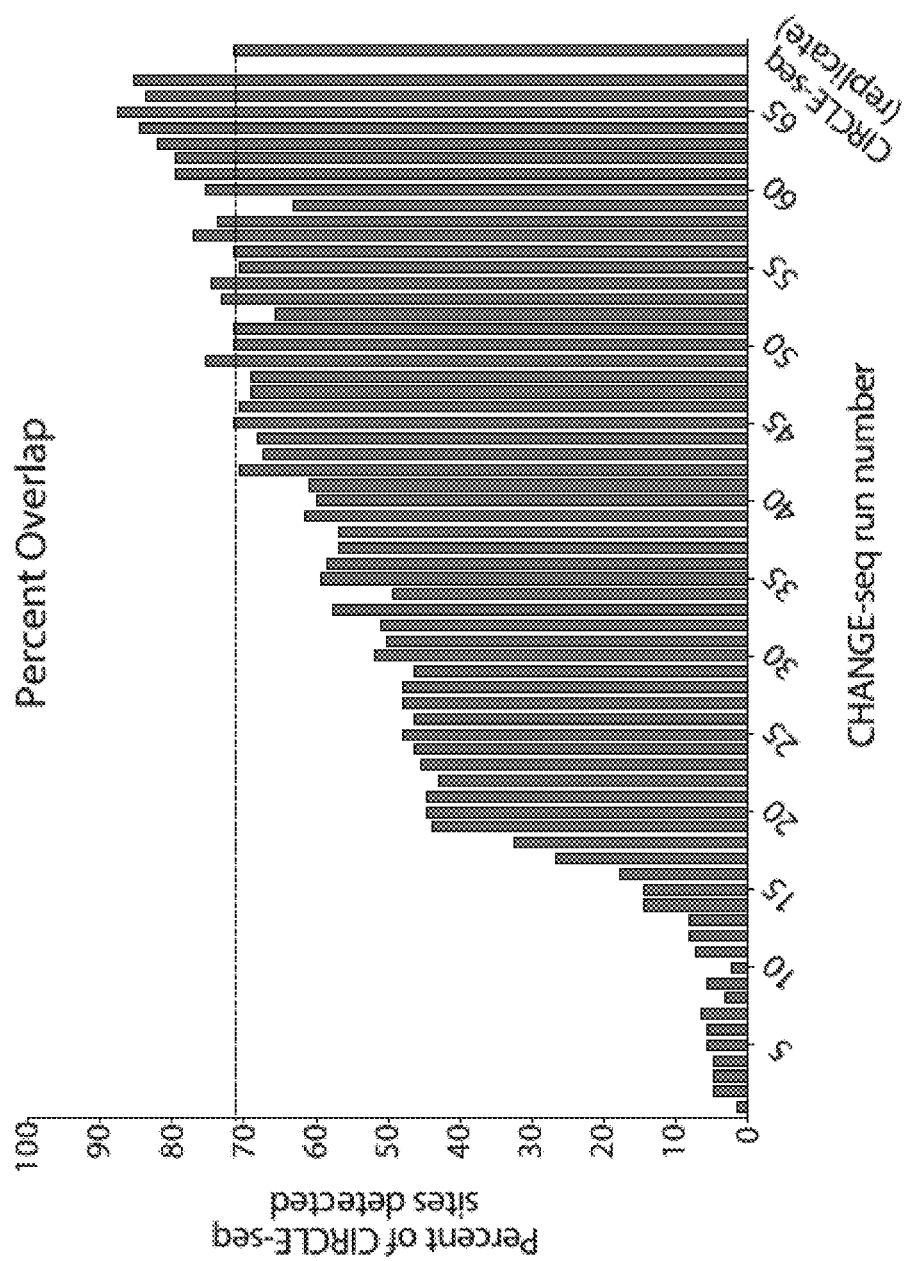
FIGS. 8A-8B. Plot of percentage of CIRCLE-seq sites (FIG. 8A) and number of sites (FIG. 8B) detected across CHANGE-seq optimization experiments using a sgRNA targeted towards EMX1.
Figure 8B:
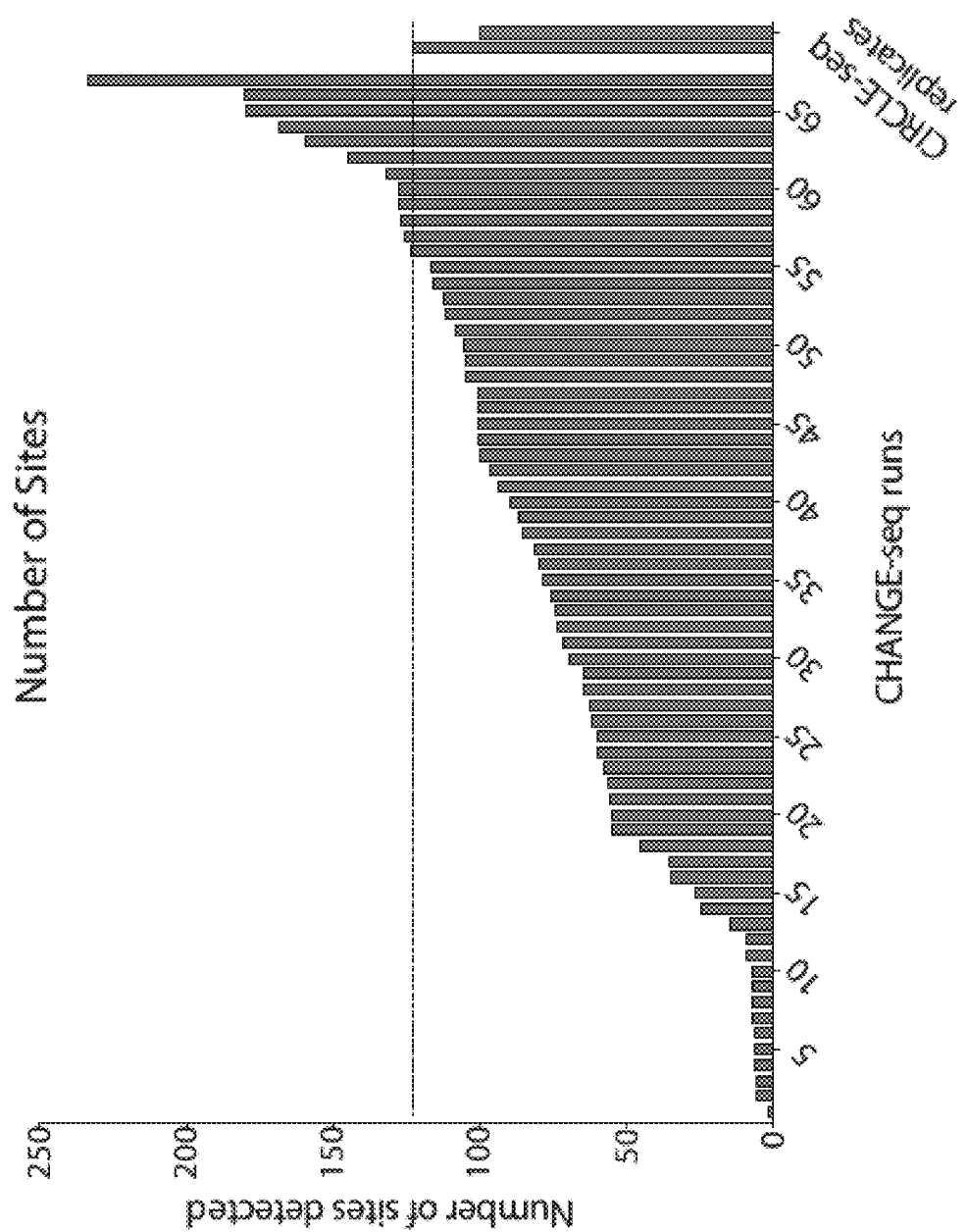
Figure 9A:
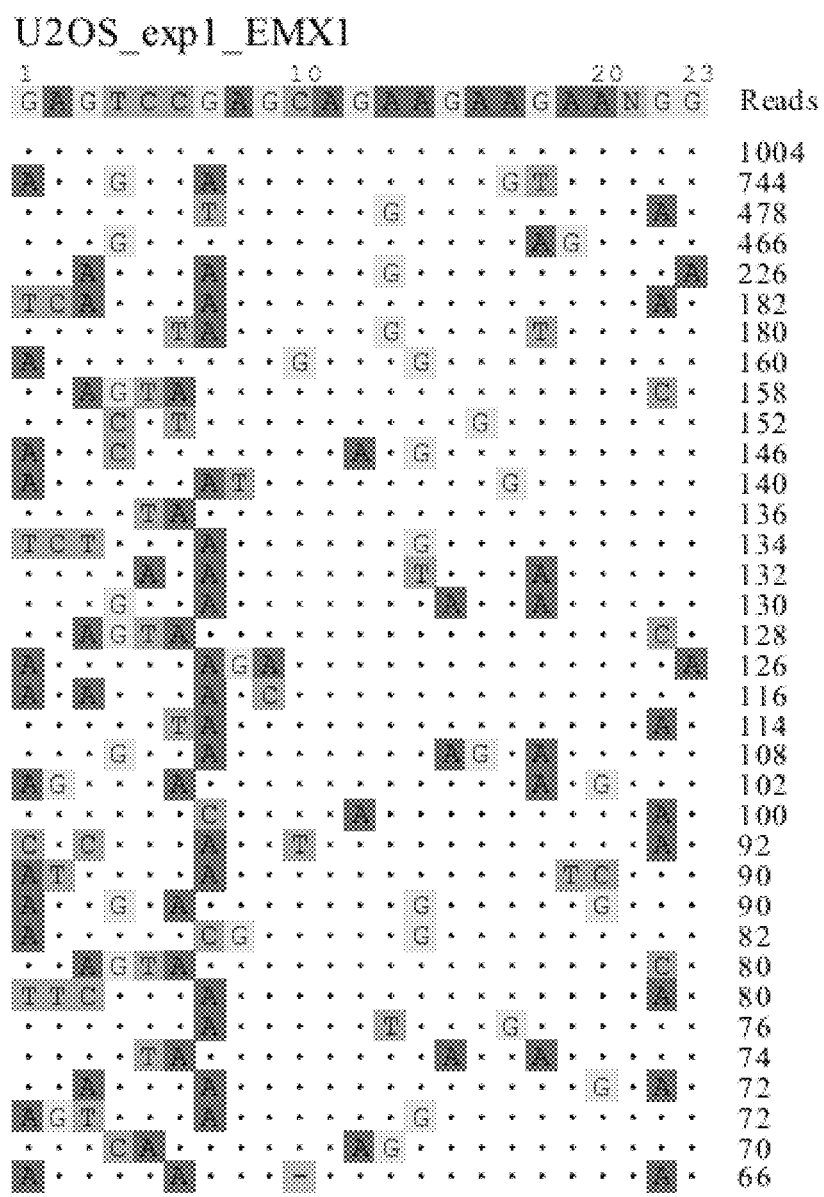
FIGS. 9A-9B. Visualization of on- and off-target sites identified by CHANGE-seq (FIG. 9A) and CIRCLE-seq (FIG. 9B) aligned against intended target site for Cas9: sgRNA complexes targeting EMX1 and VEGFA site 1. Output is truncated to top sites.
Figure 9B:
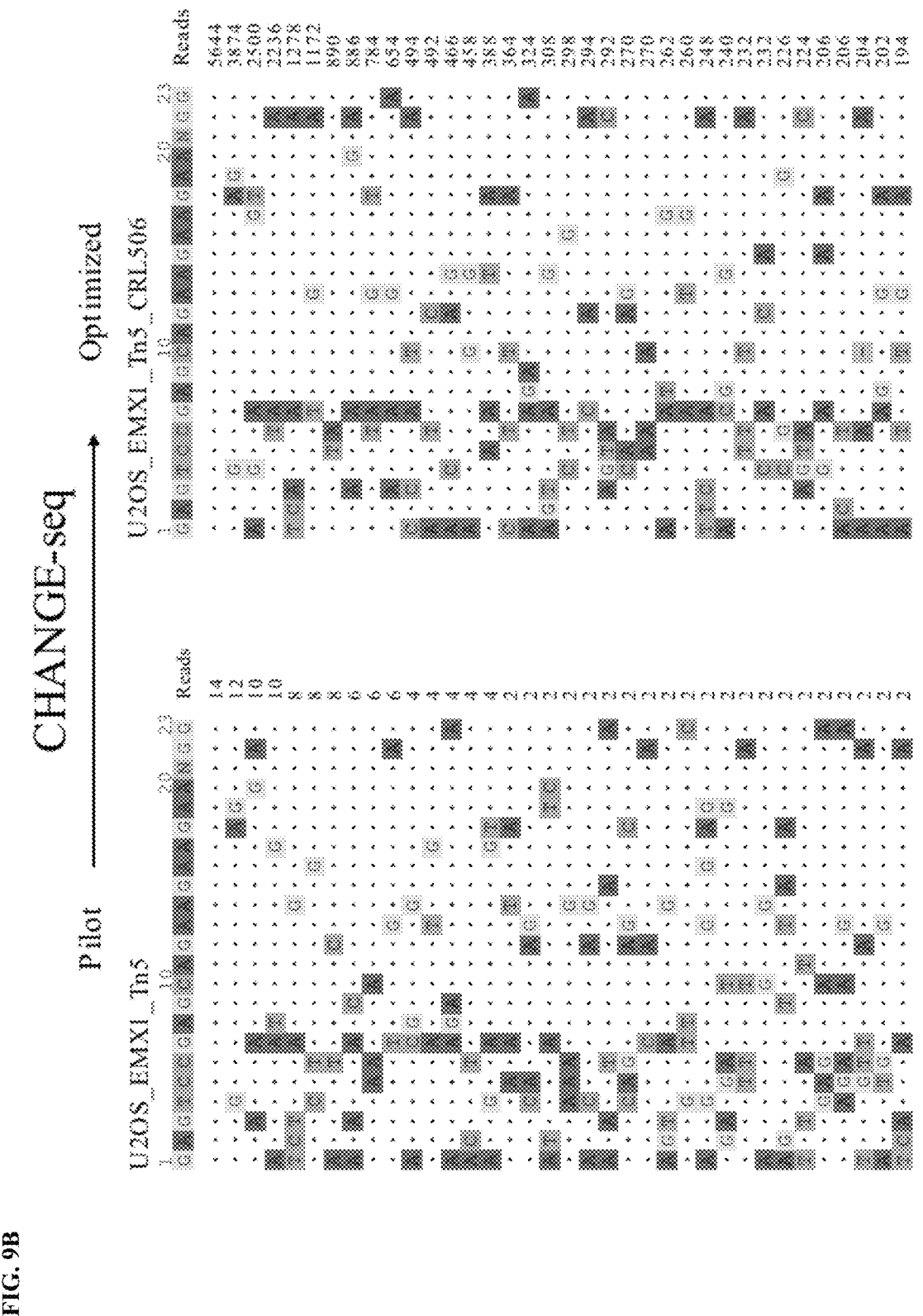
Figure 10:
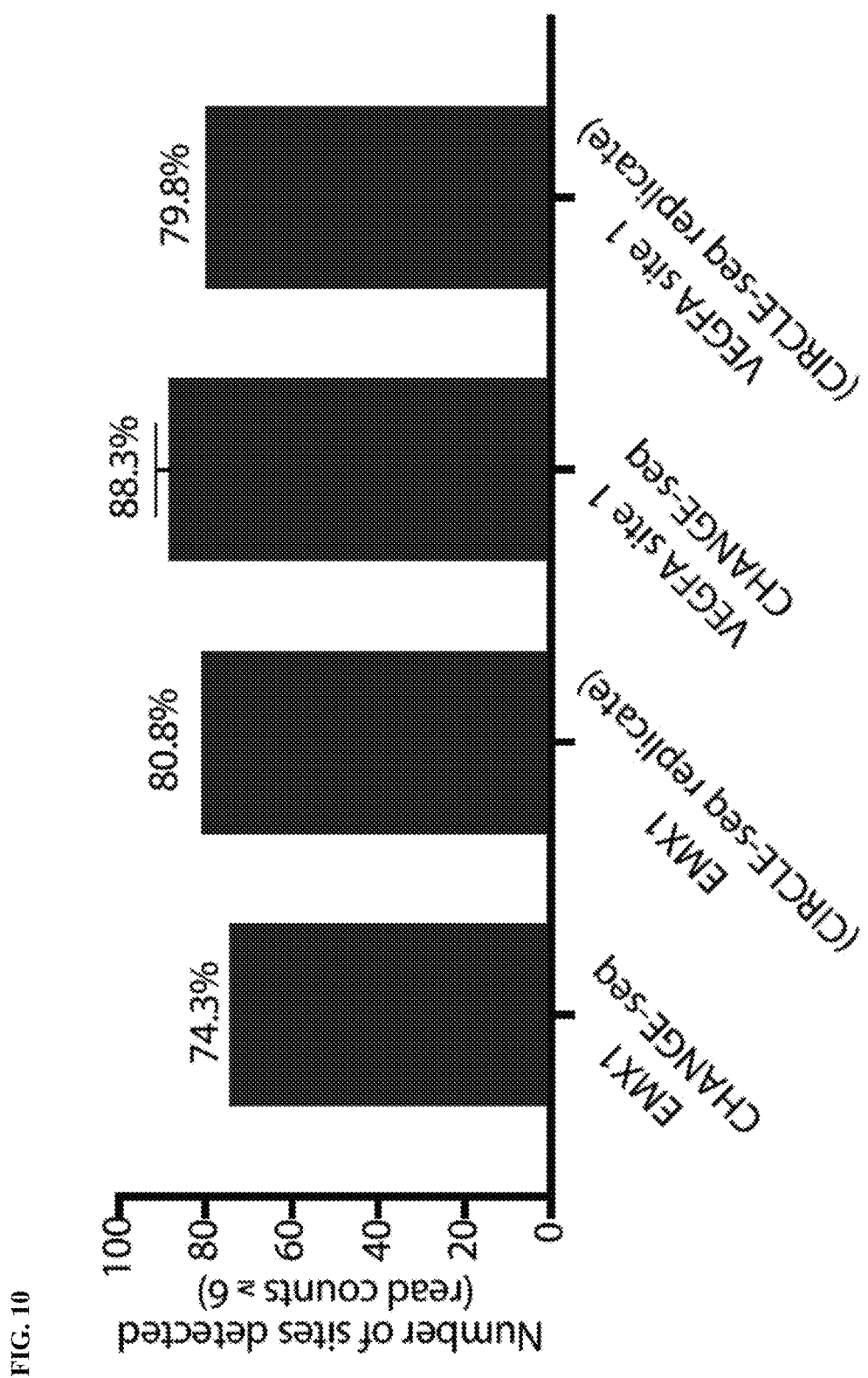
FIG. 10. Plot of percentage of CIRCLE-seq sites detected by CHANGE-seq using sgRNAs targeted towards EMX1 and VEGFA site 1.
Figure 12A:
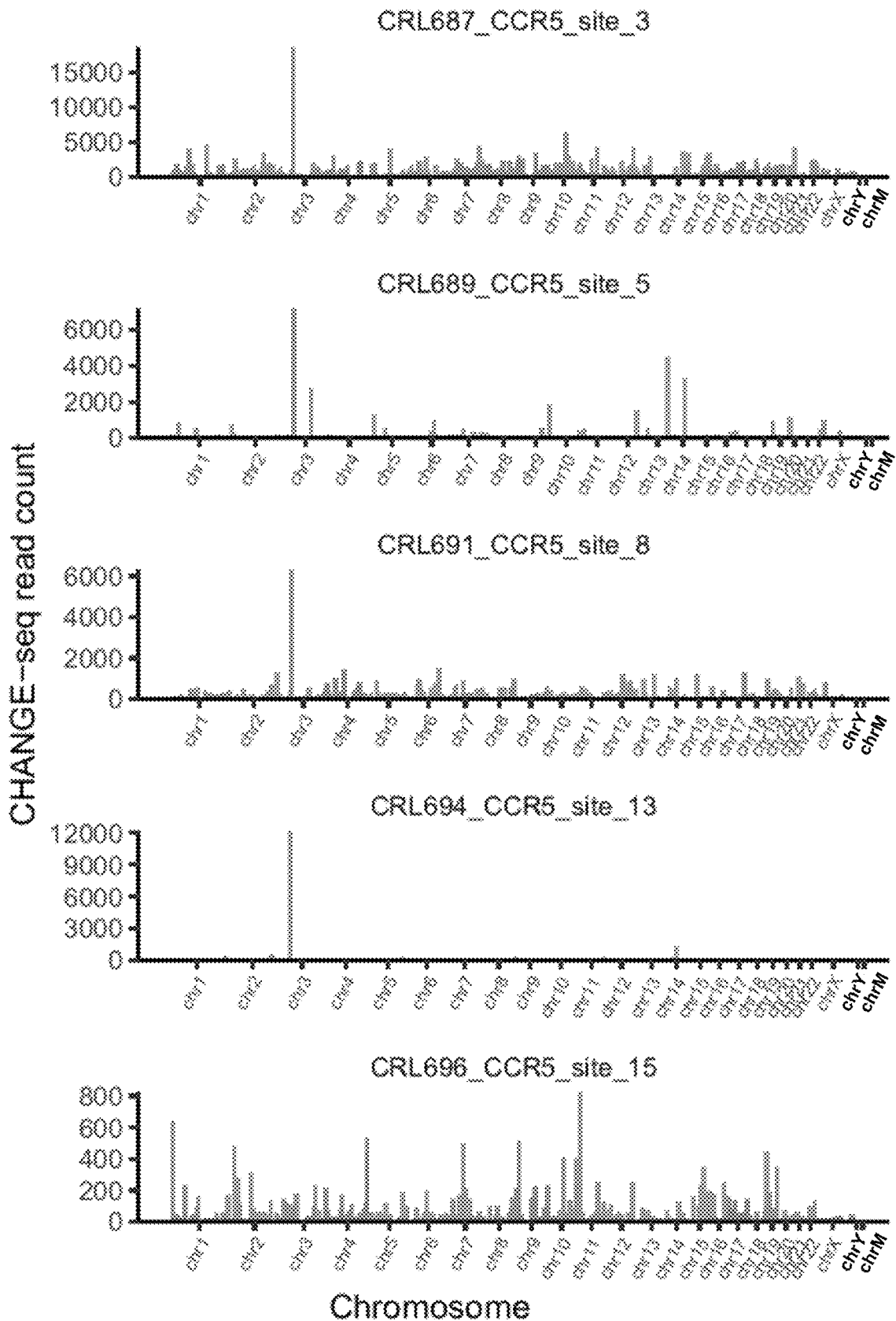
FIGS. 12A-12V. Manhattan plots of CHANGE-seq data for 110 Cas9 gRNAs targeted against 13 human genes. Data show raw CHANGE-seq read counts plotted by chromosomal position.
Figure 12B:
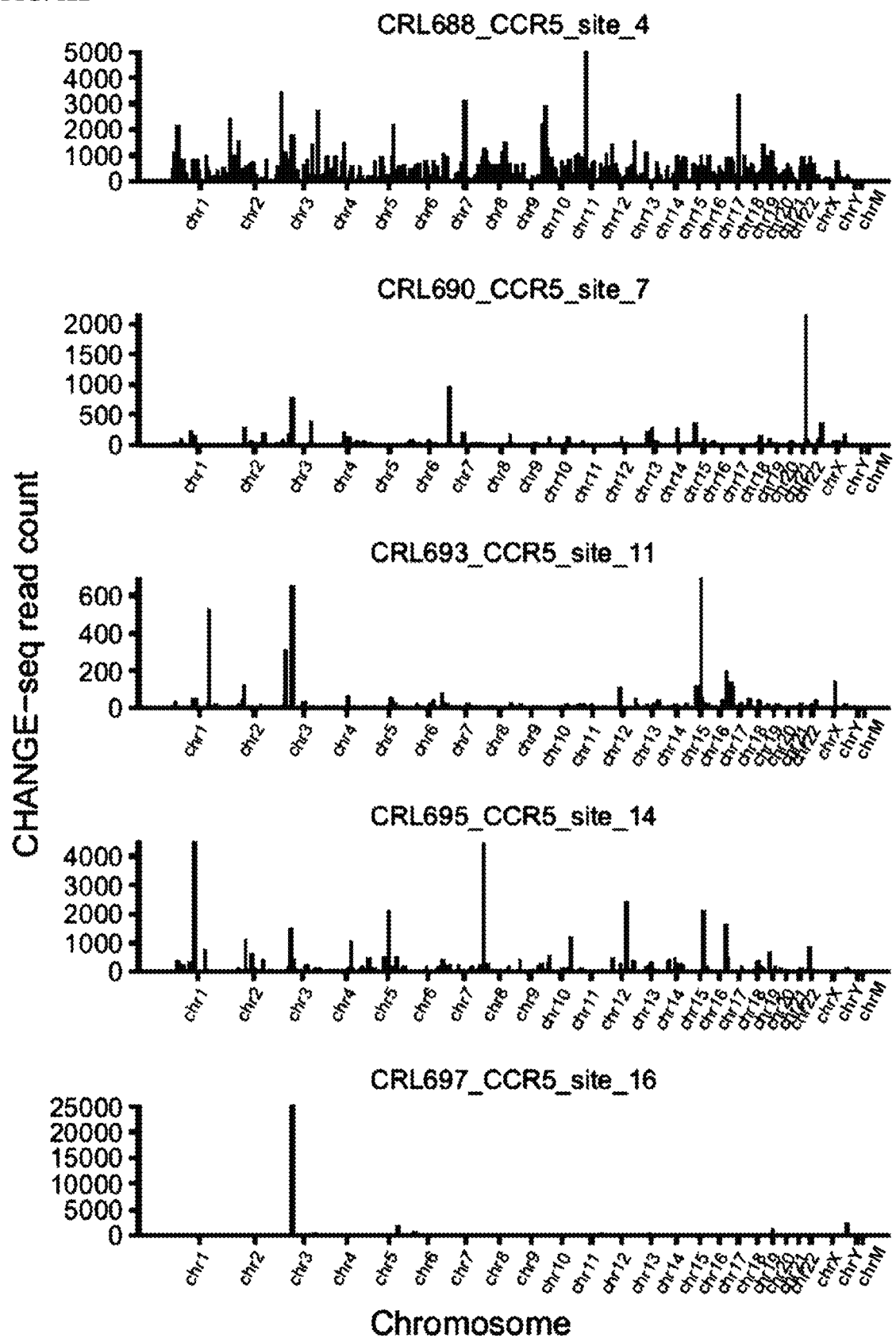
Figure 12C:
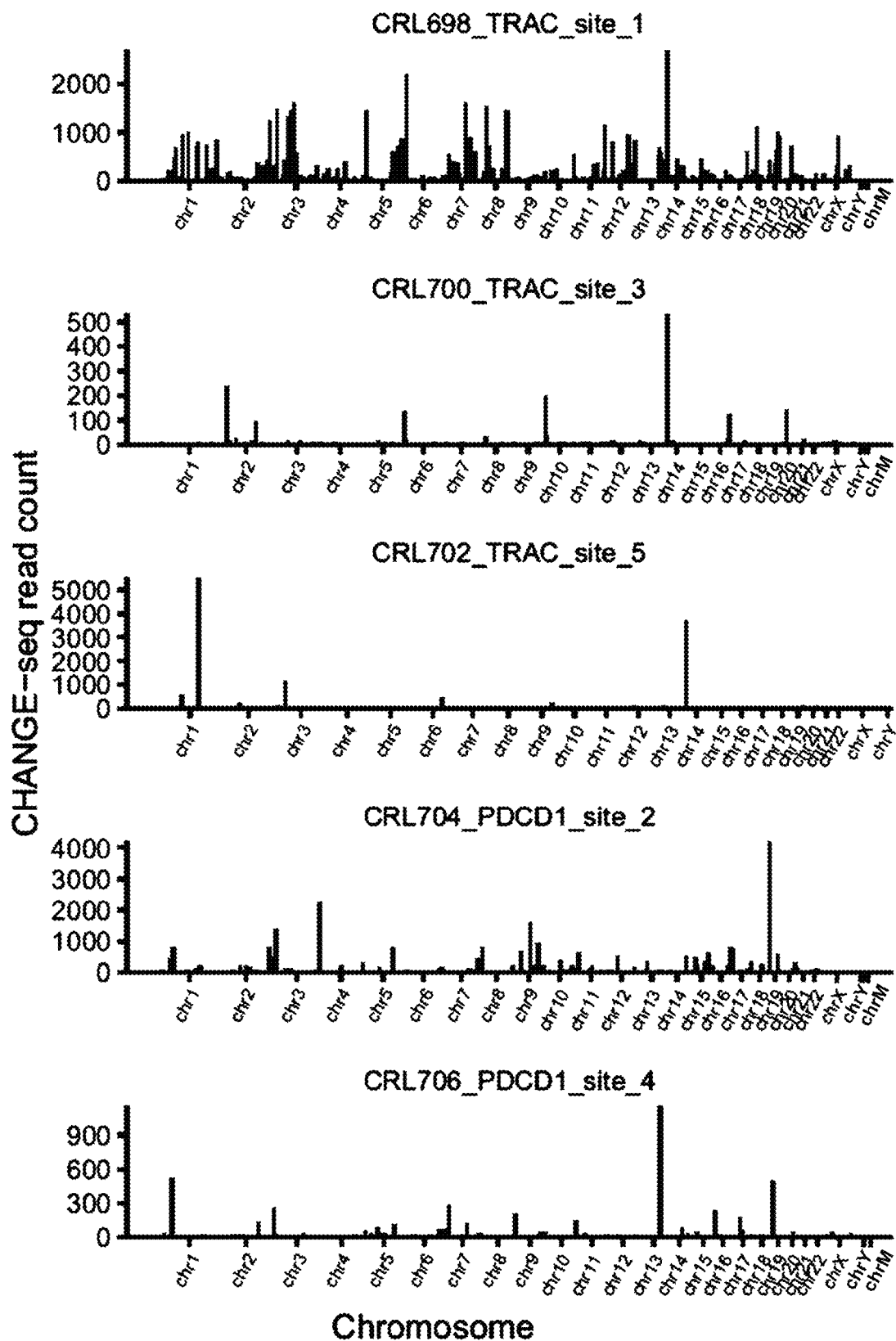
Figure 12D:
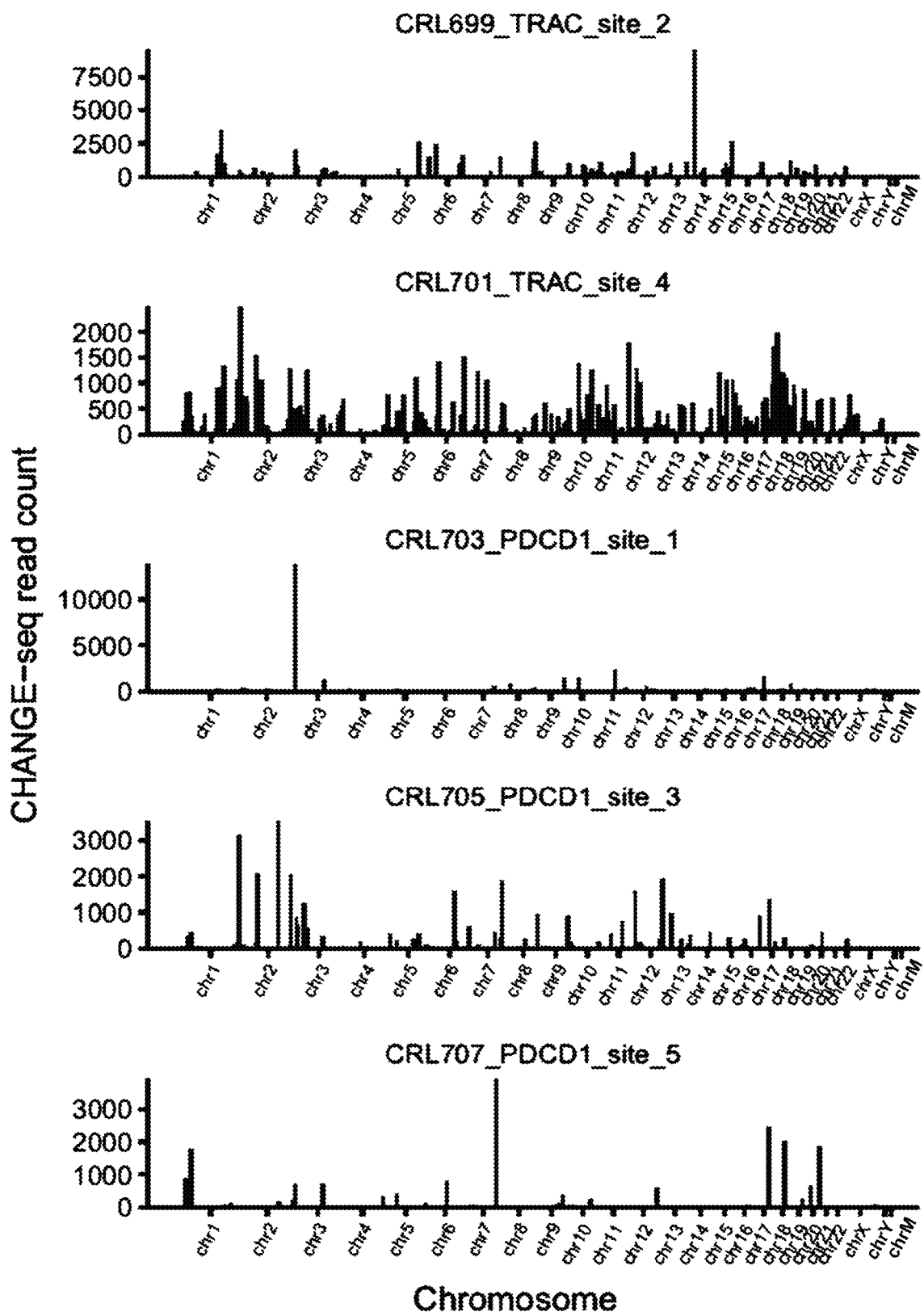
Figure 12E:
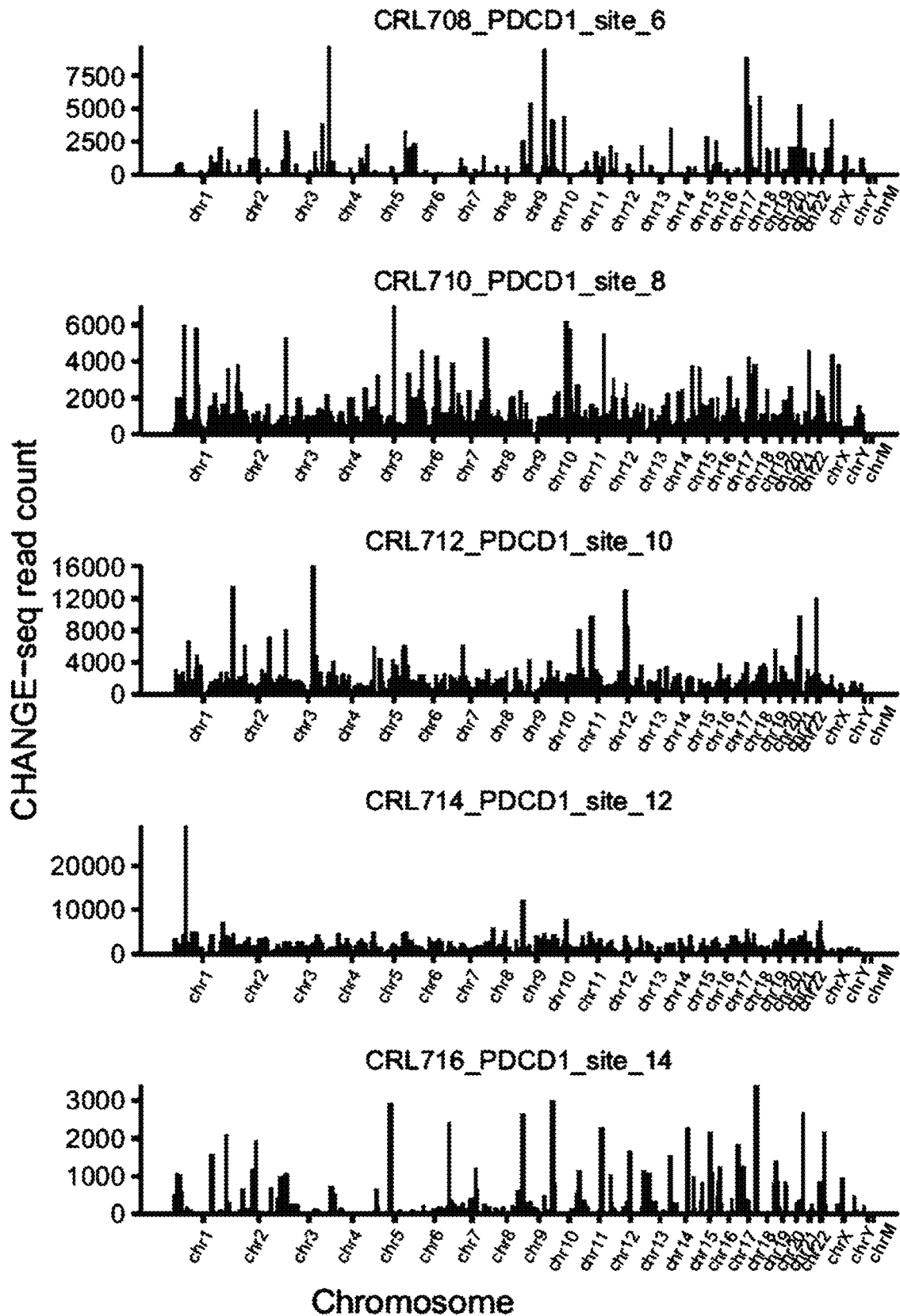
Figure 12F:
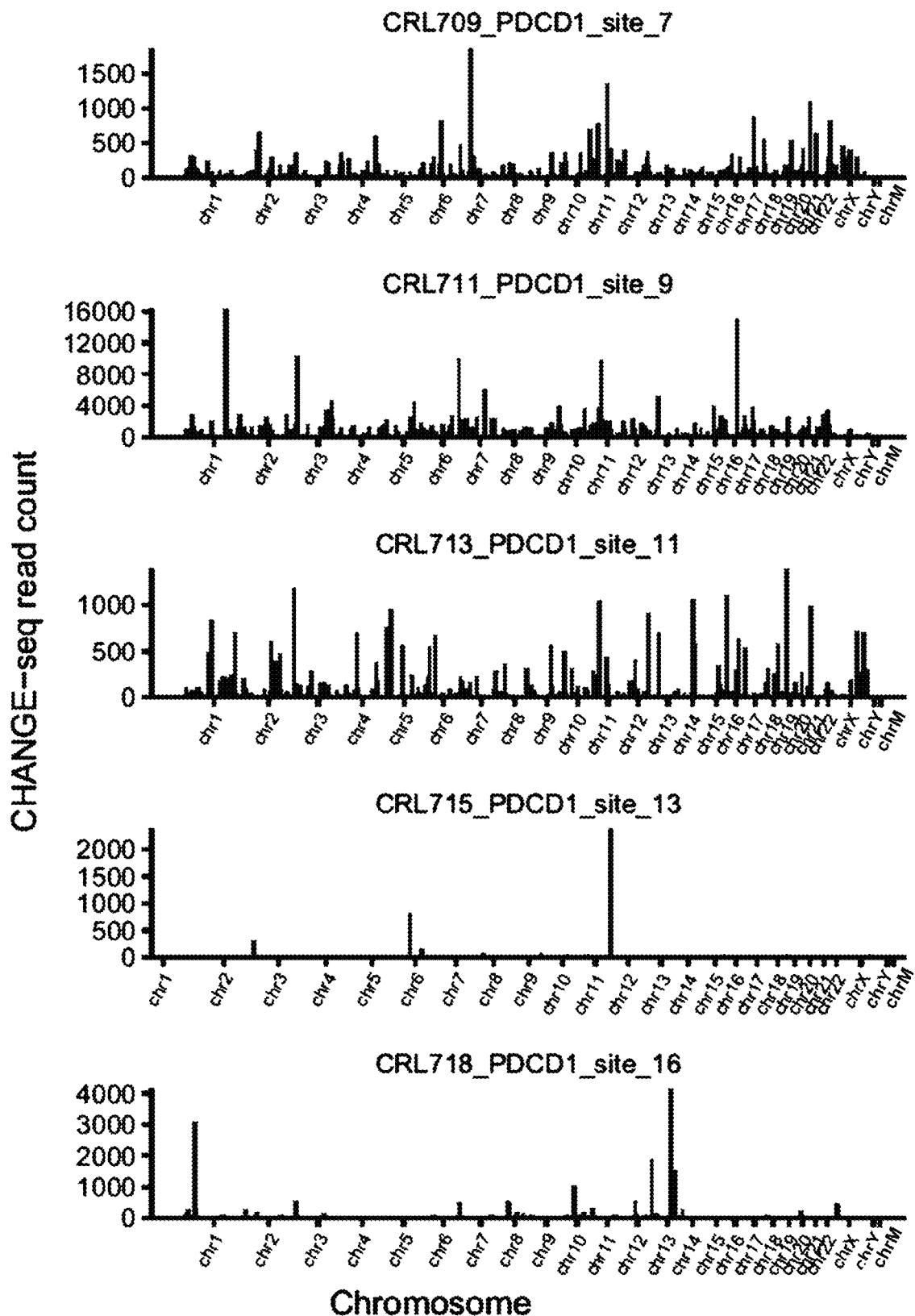
Figure 12G:
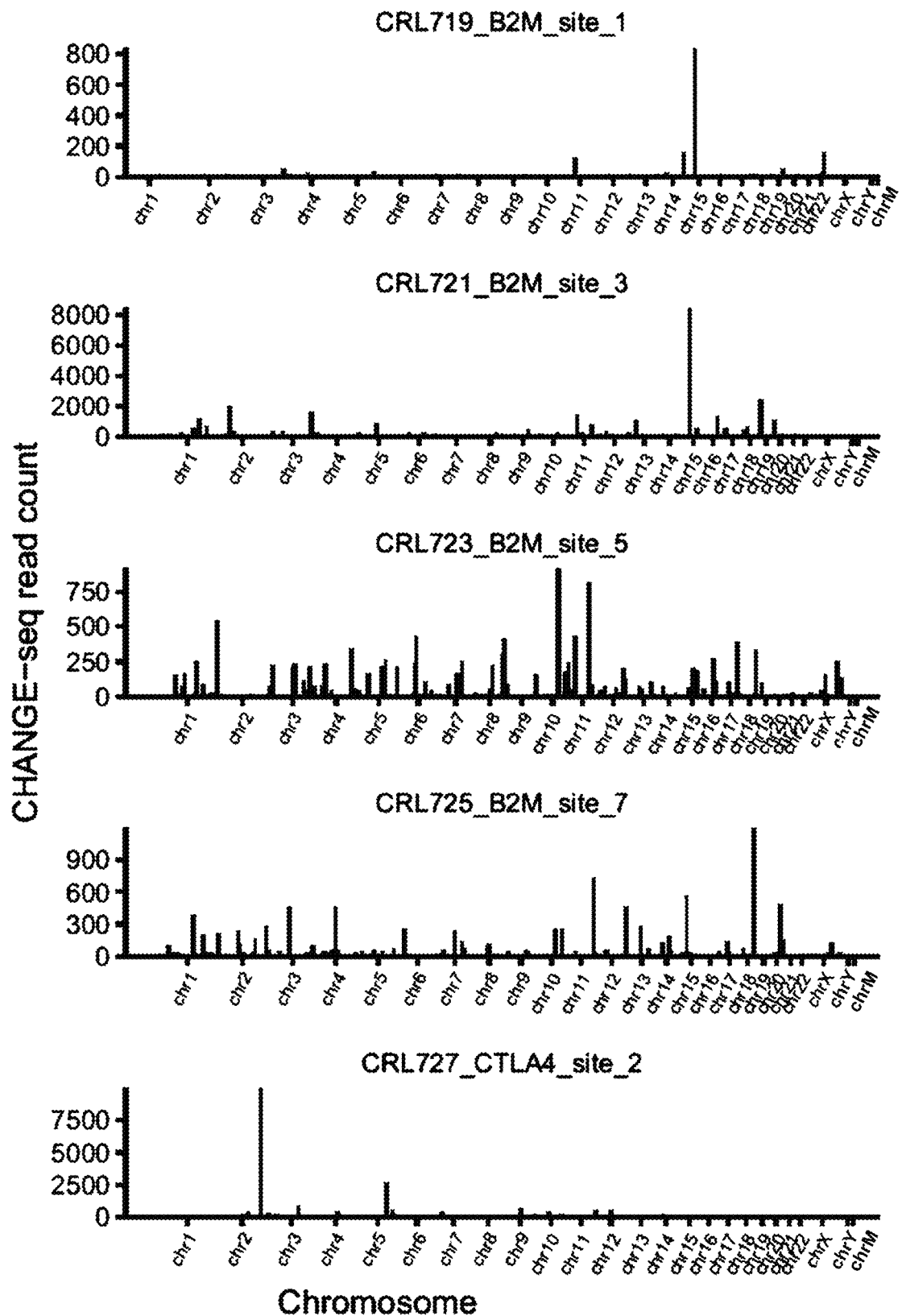
Figure 12H:
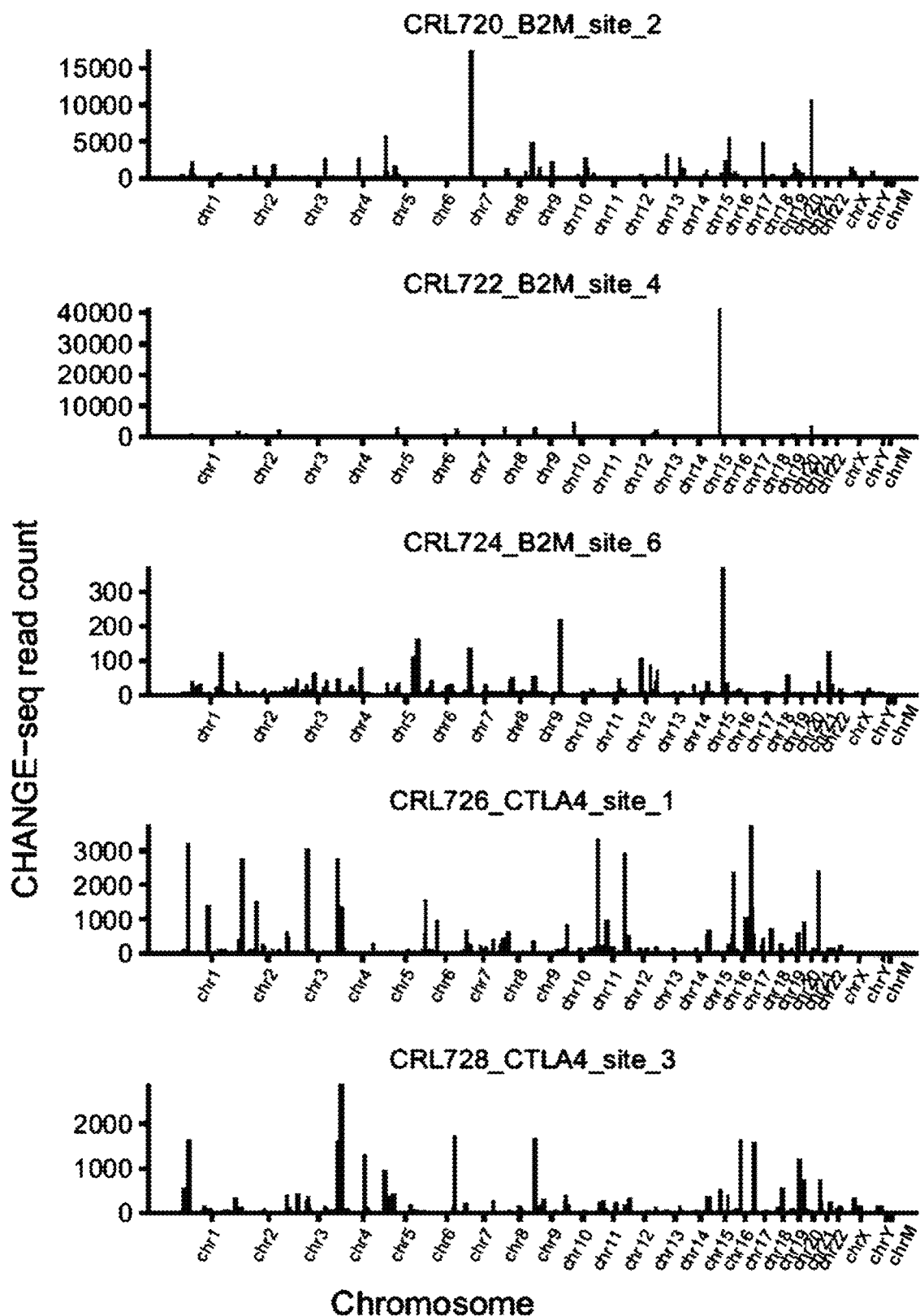
Figure 12I:
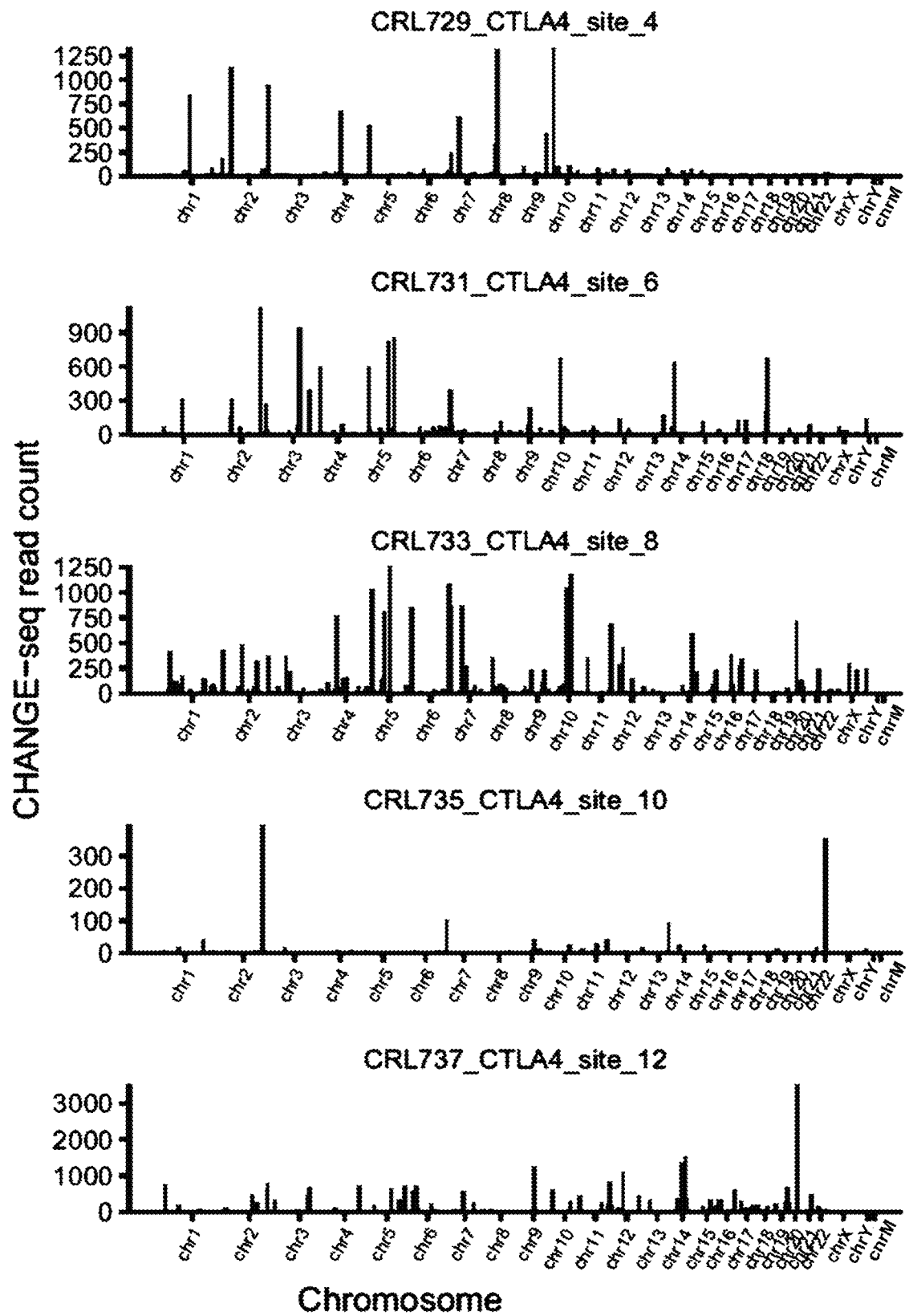
Figure 12J:
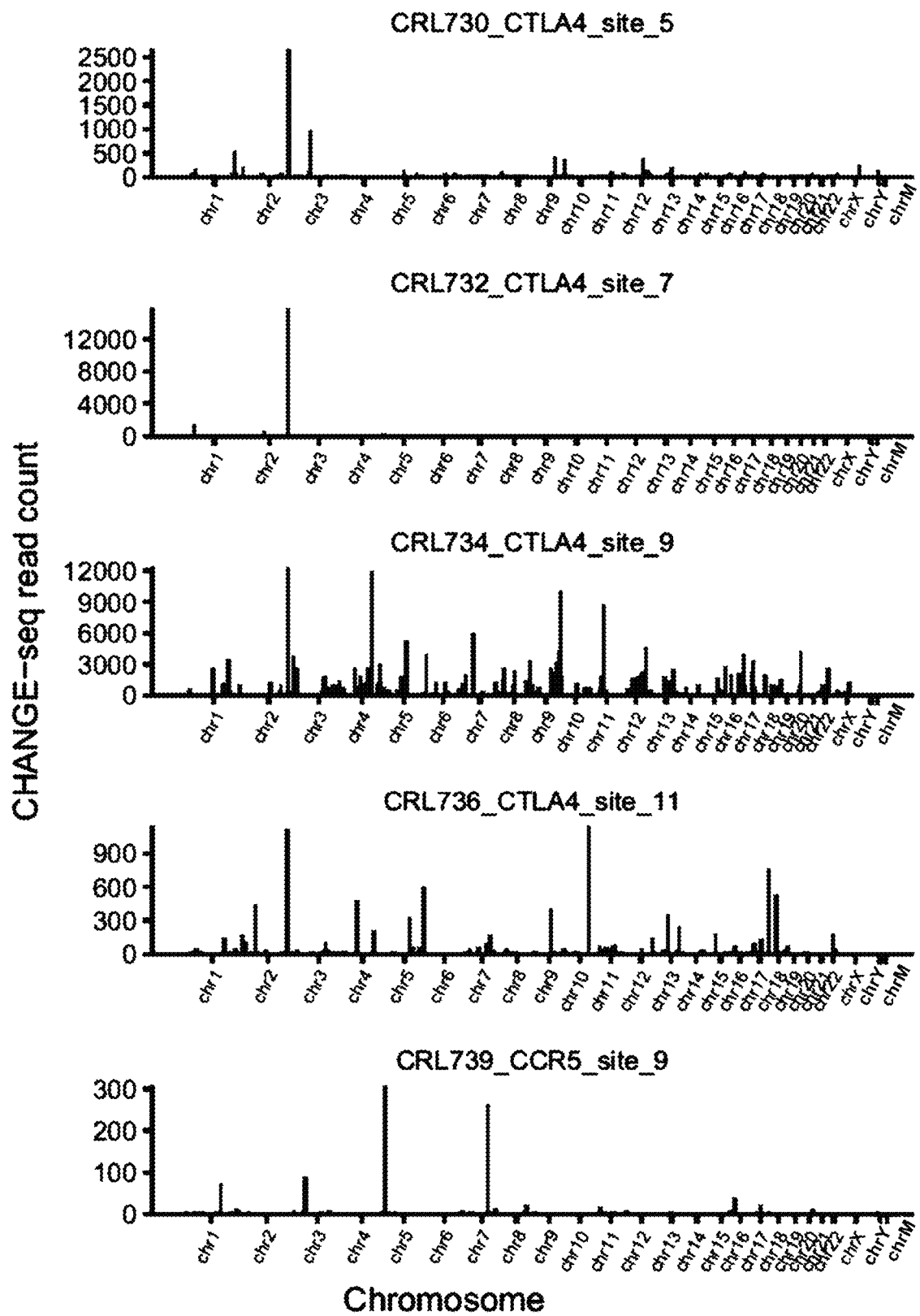
Figure 12K:
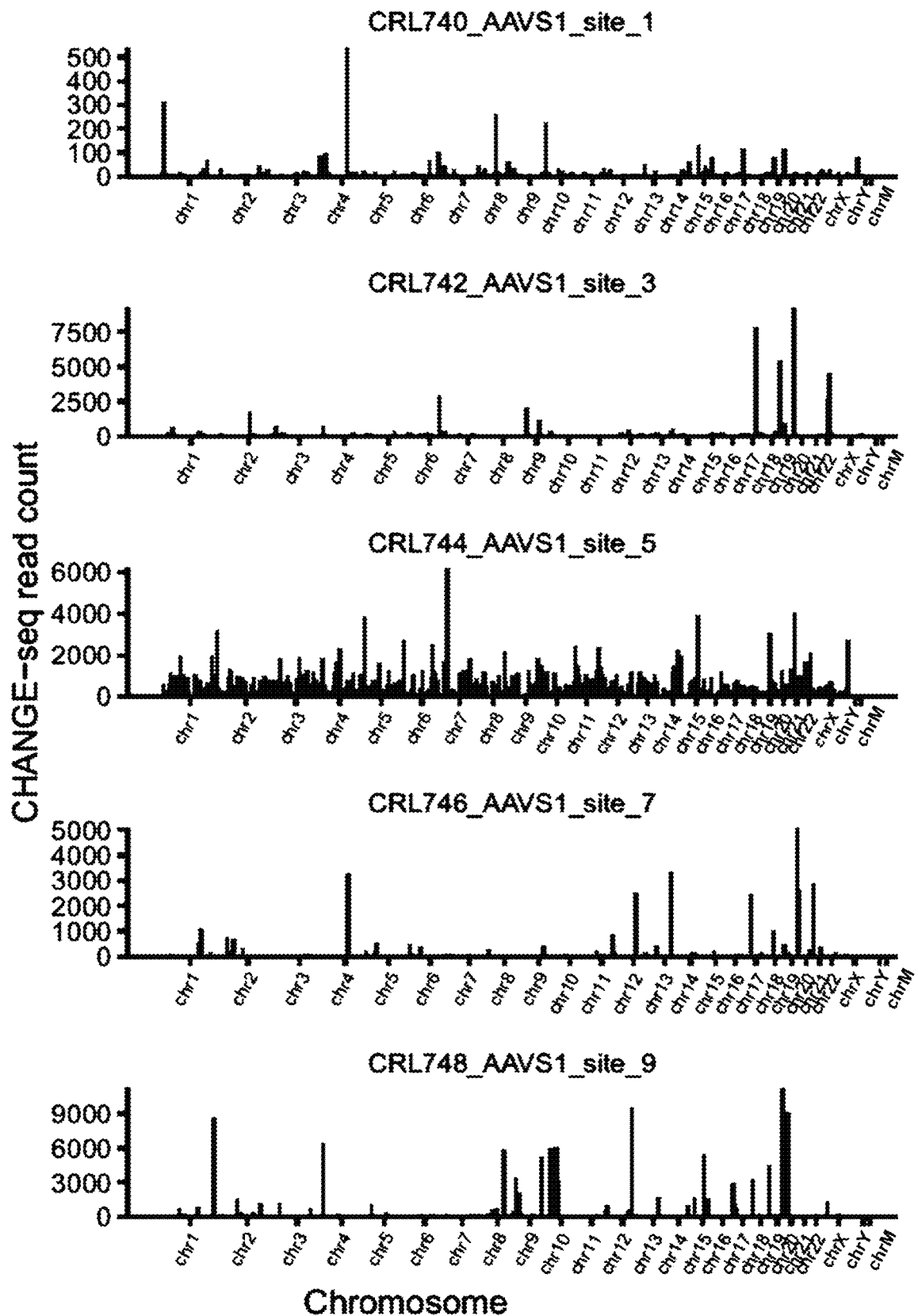
Figure 12L:
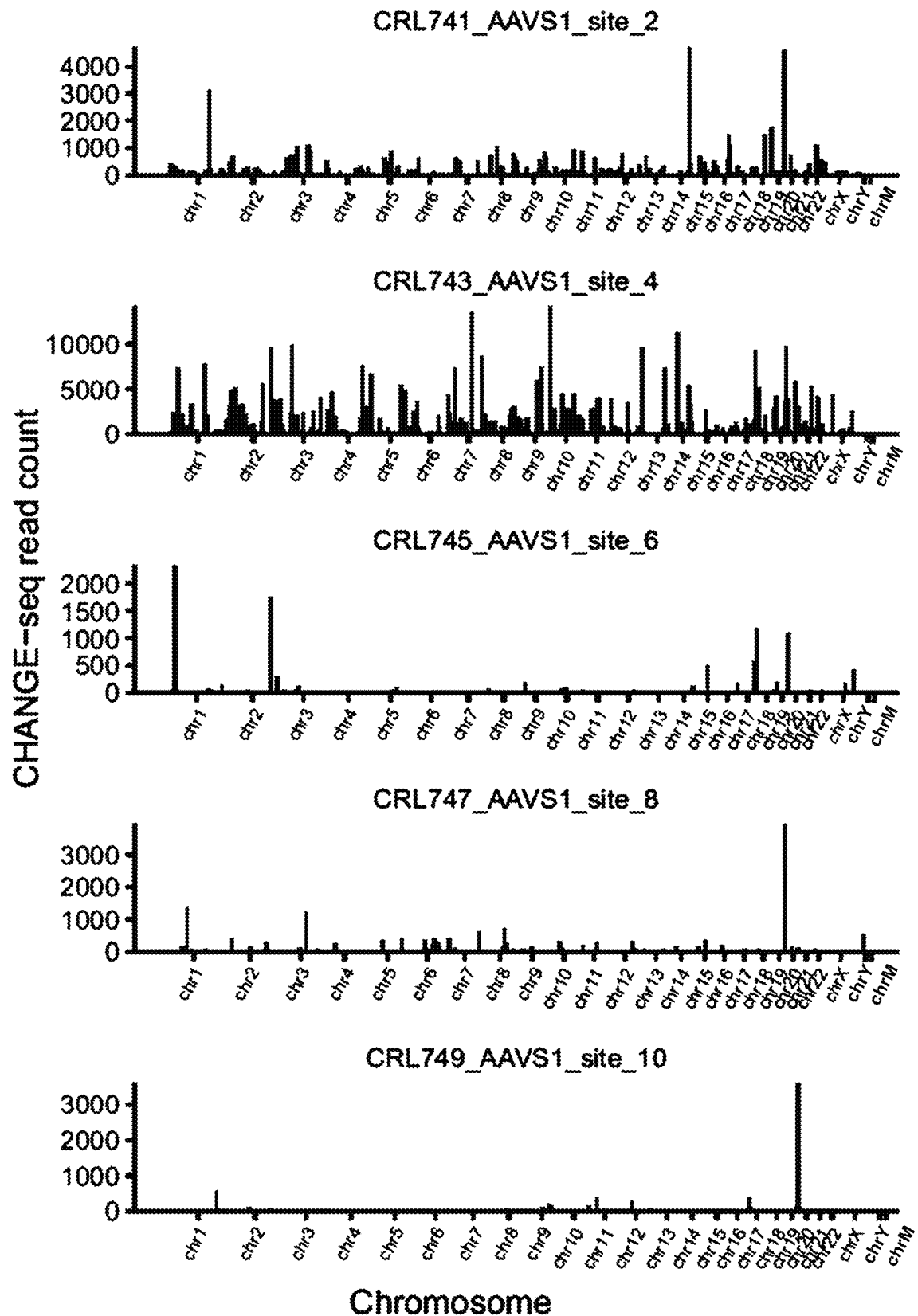
Figure 12M:
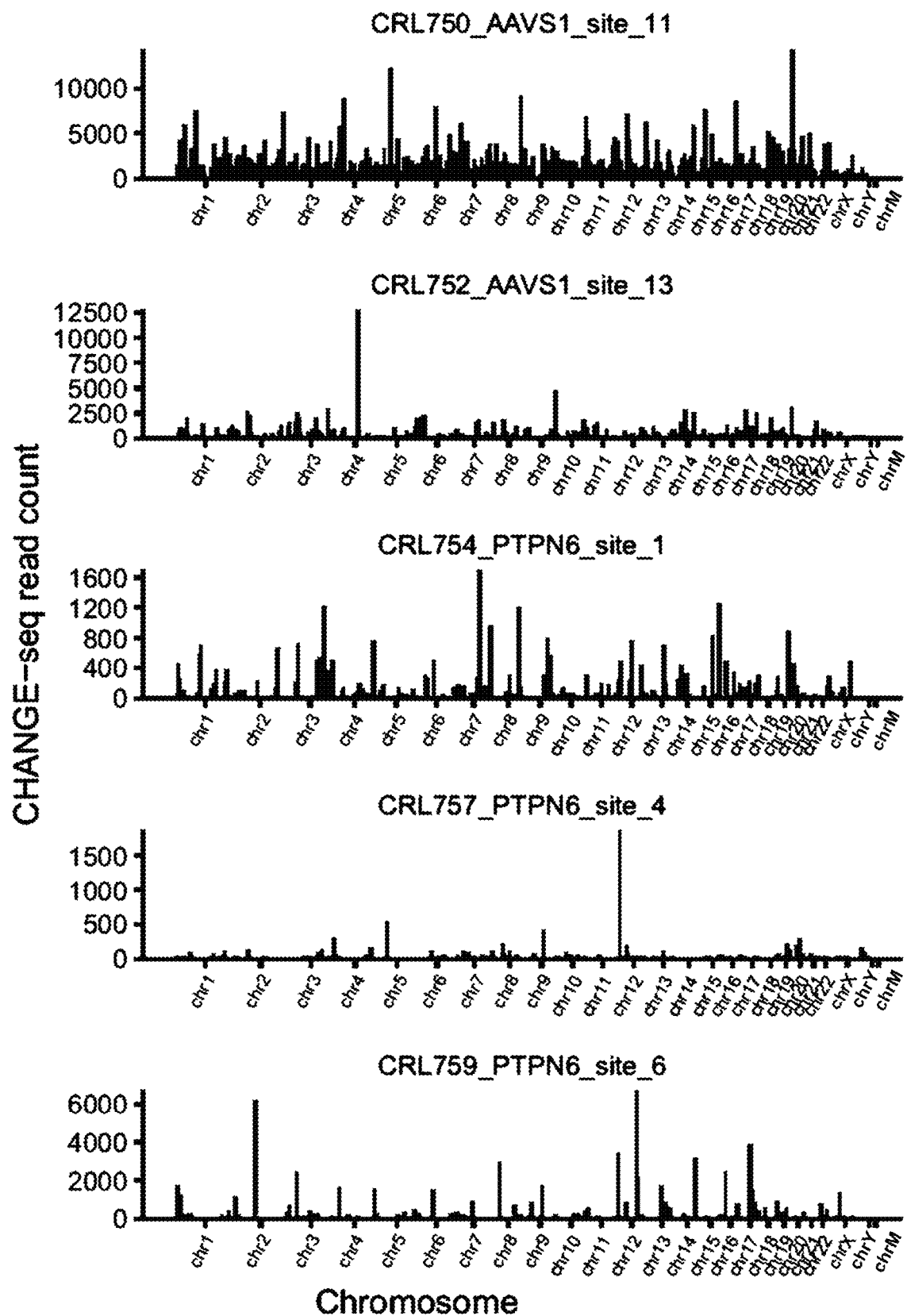
Figure 12N:
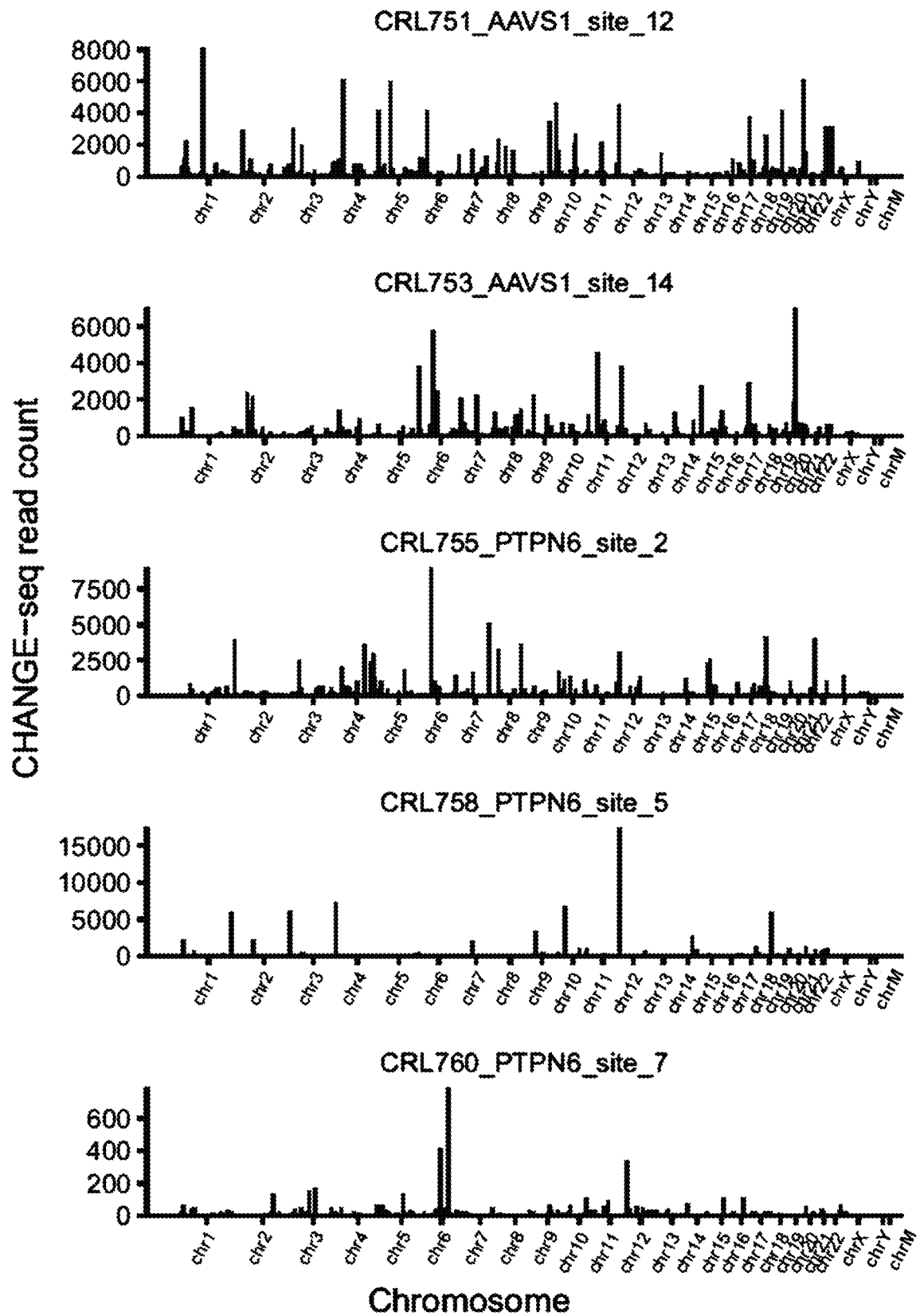
Figure 12O:
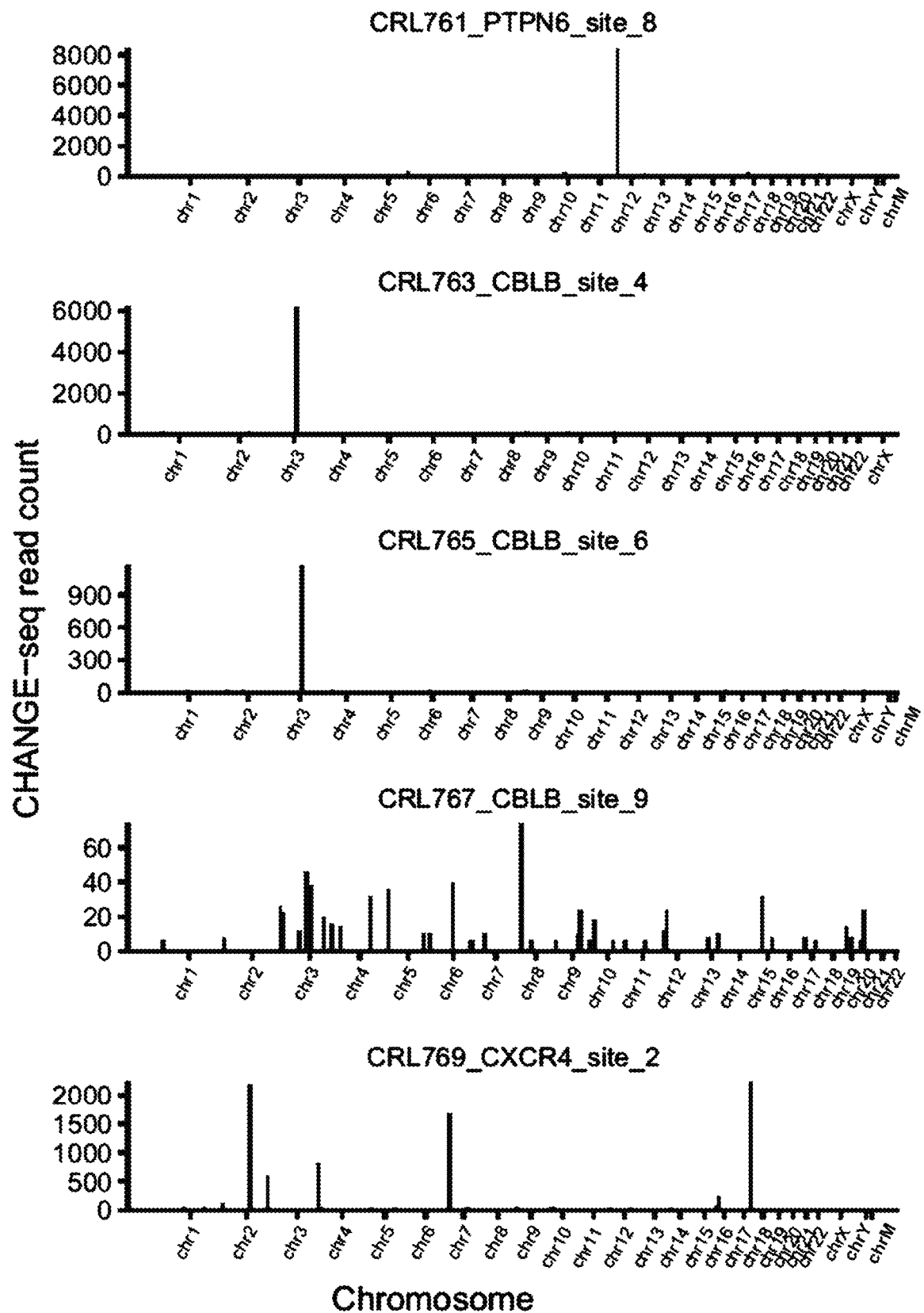
Figure 12P:
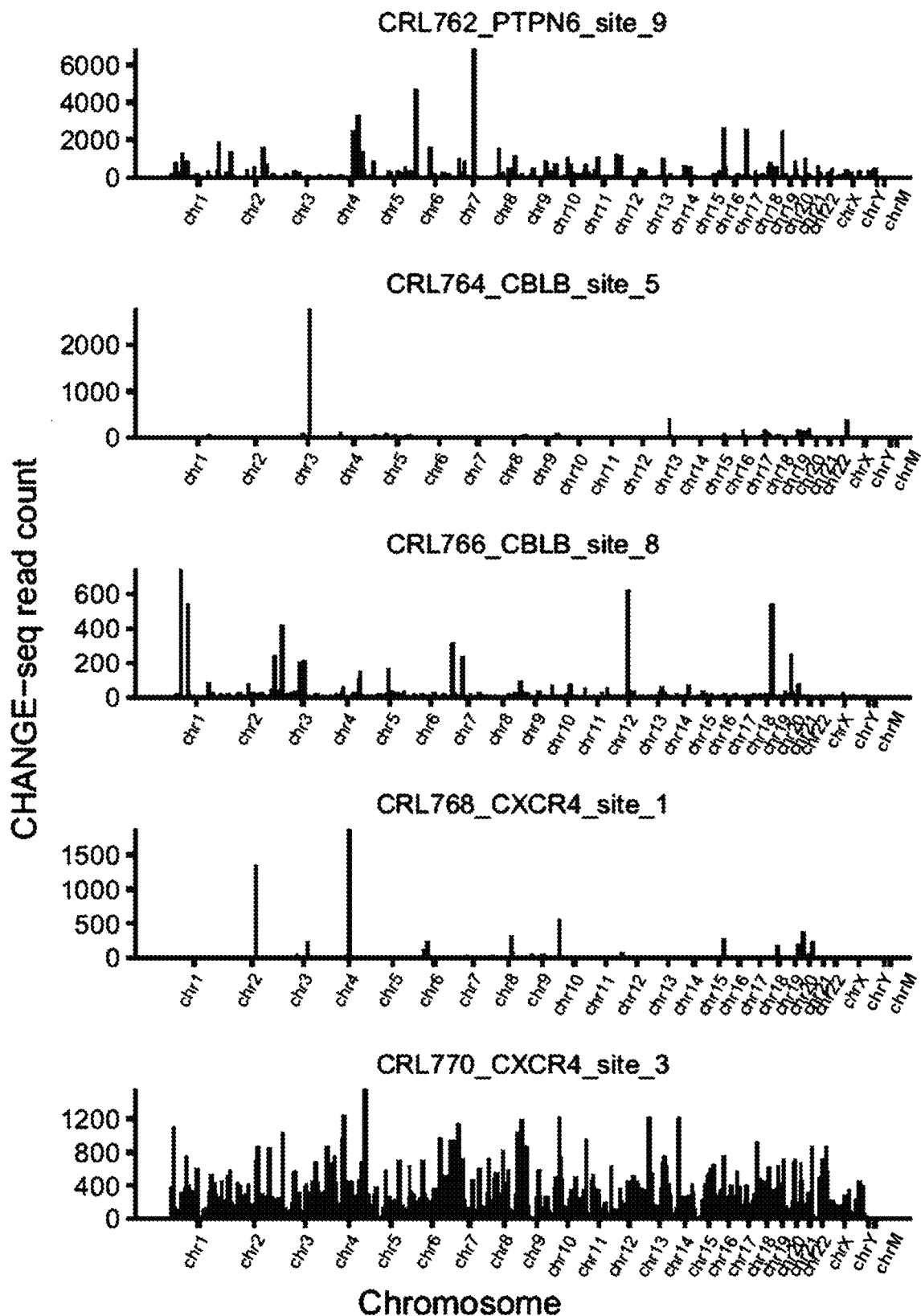
Figure 12Q:
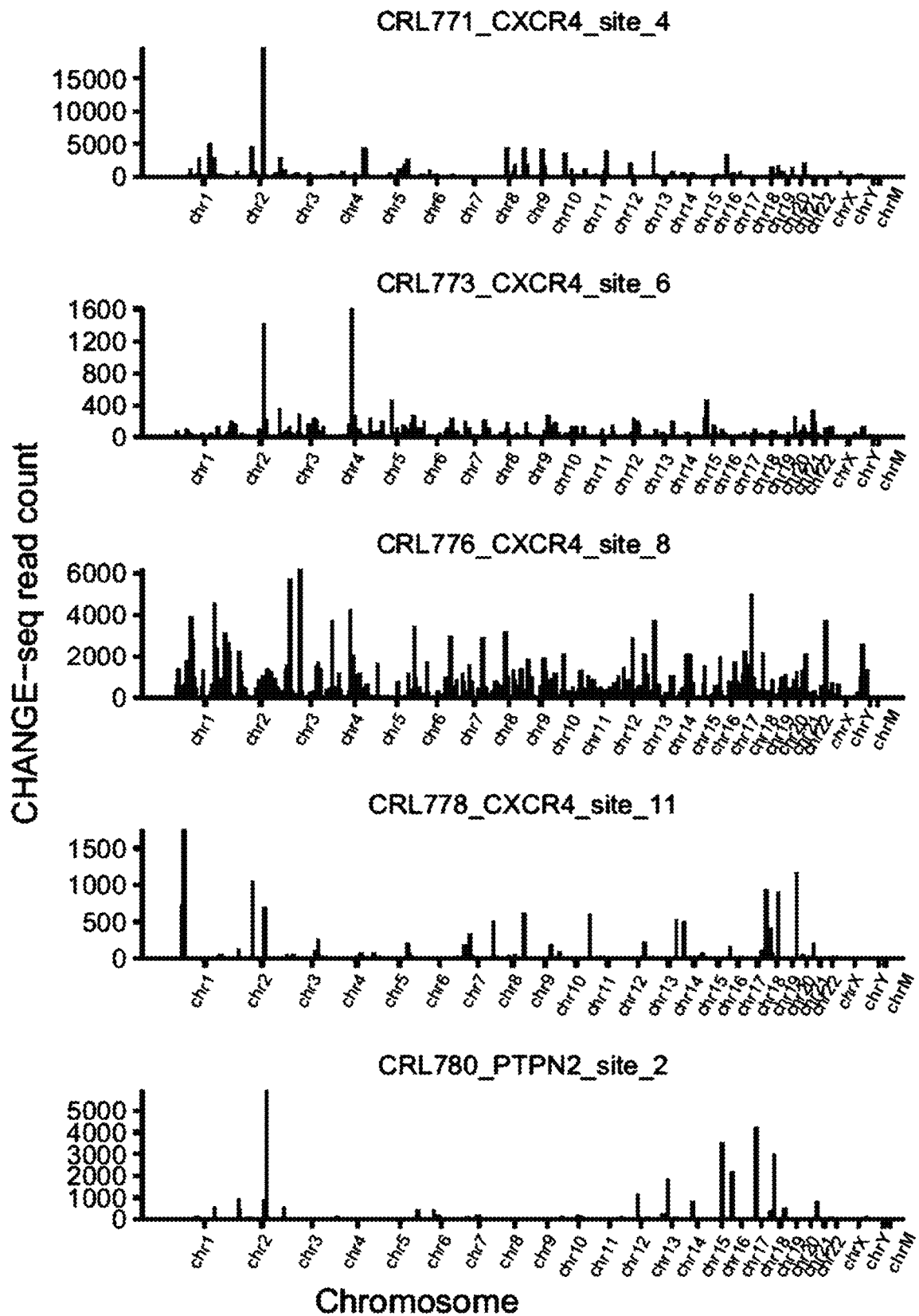
Figure 12R:
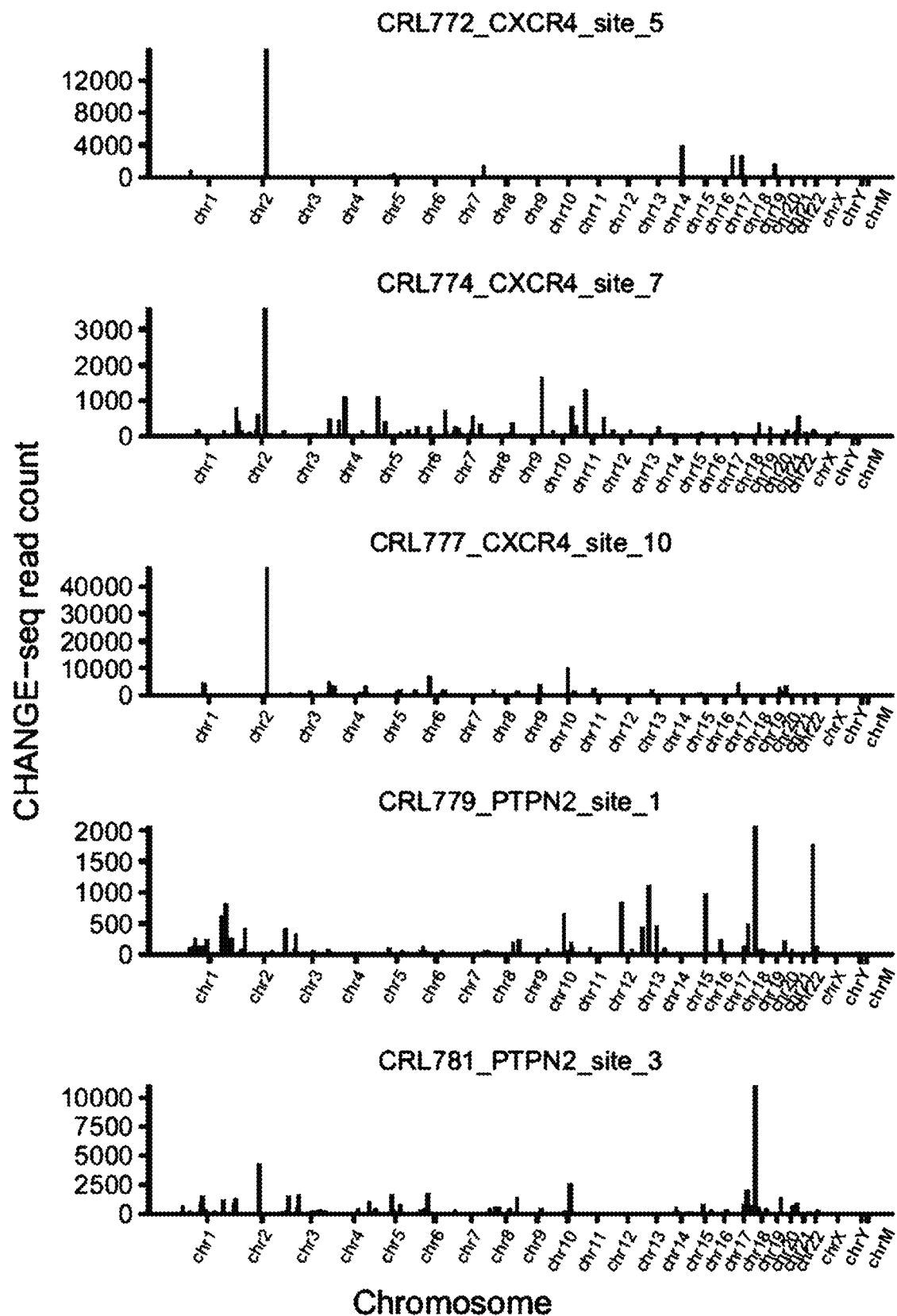
Figure 12S:
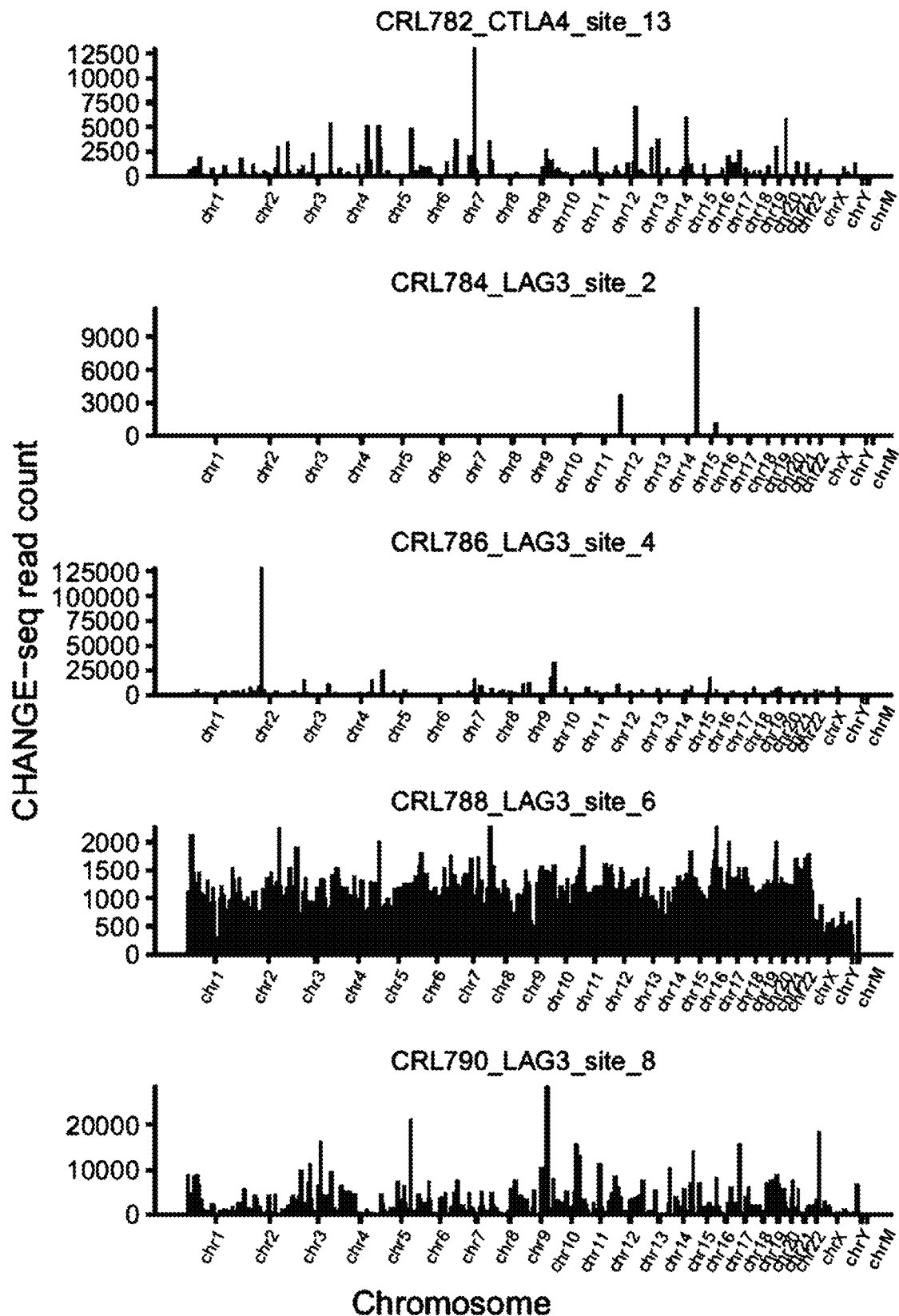
Figure 12T:
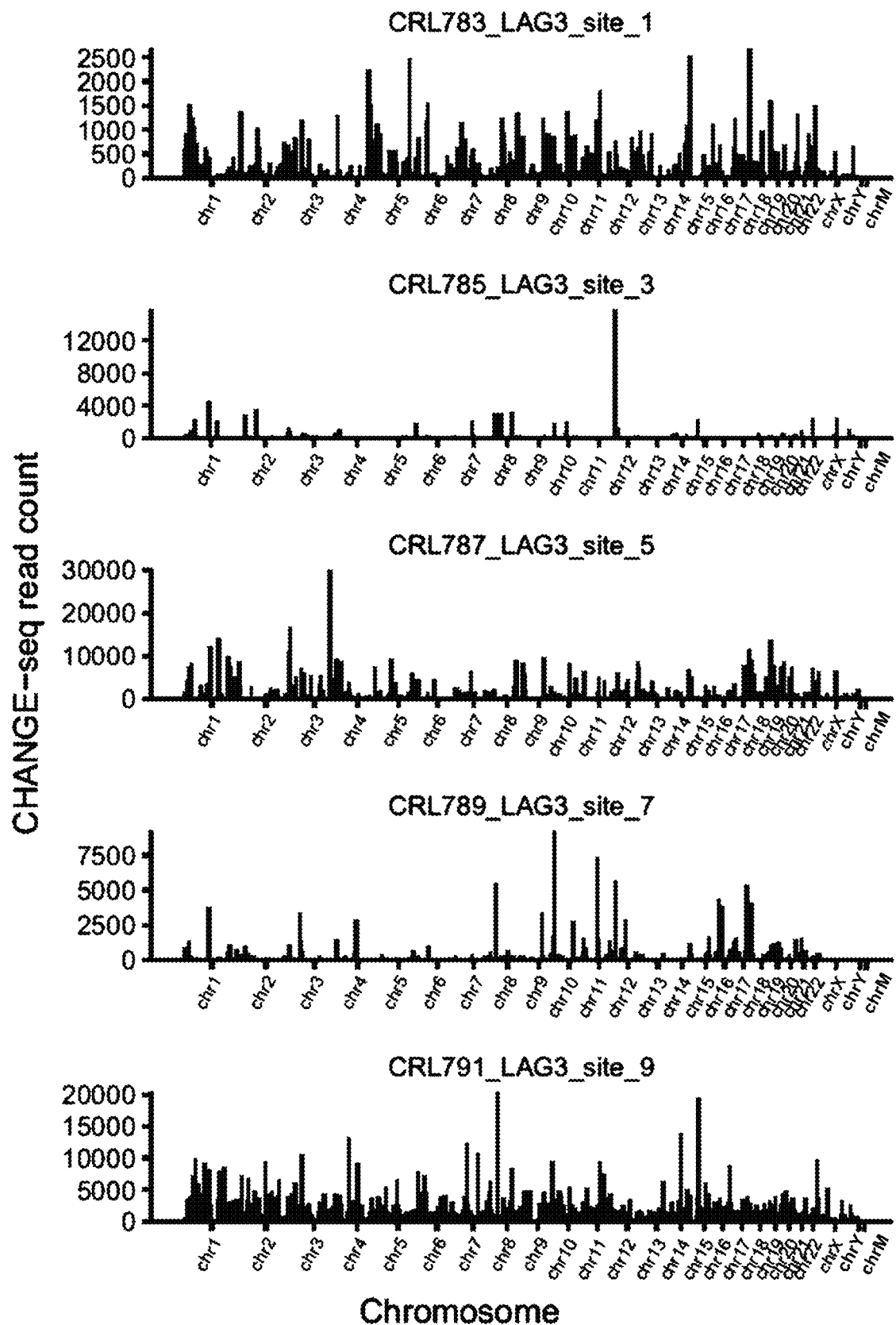
Figure 12U:
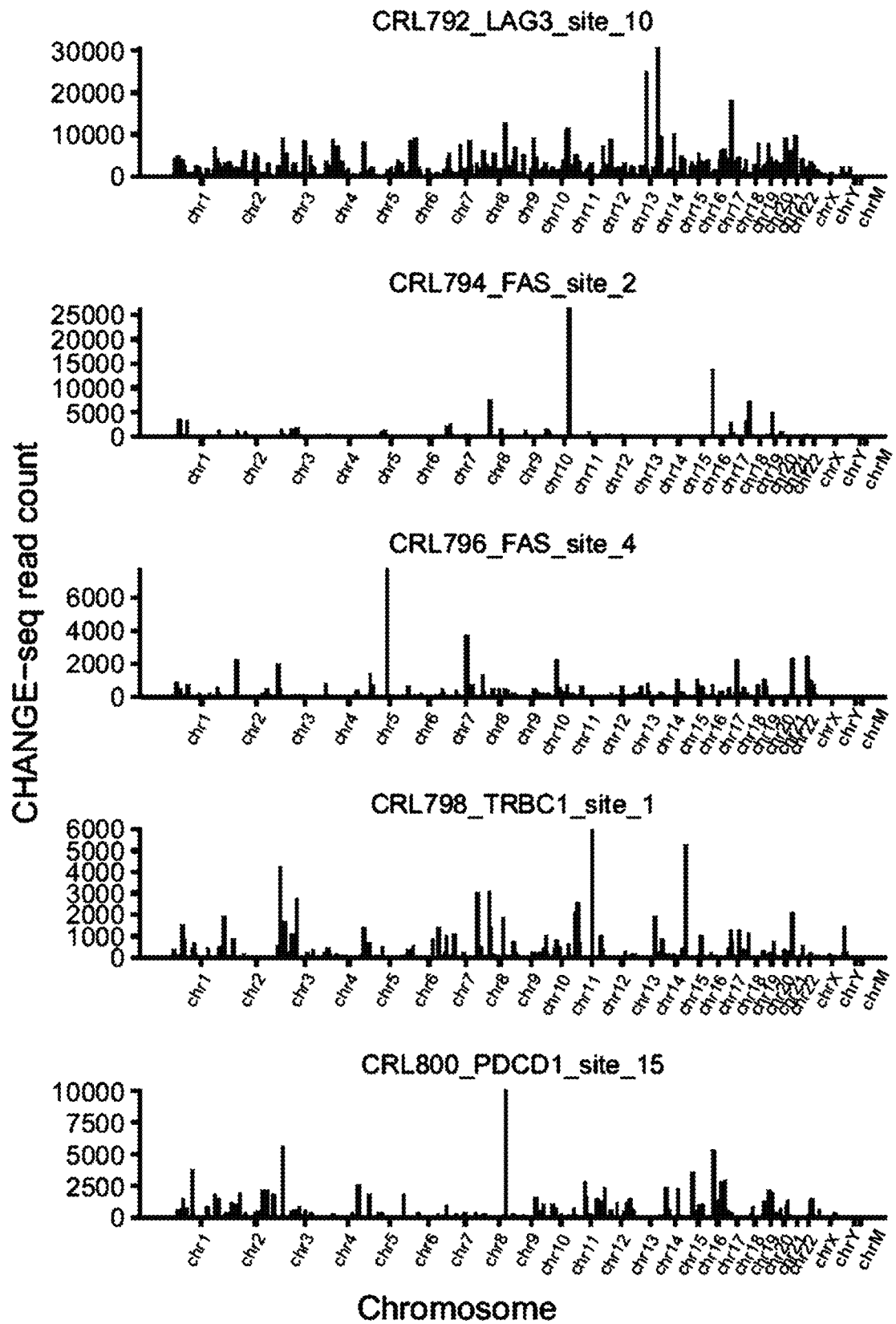
Figure 12V:
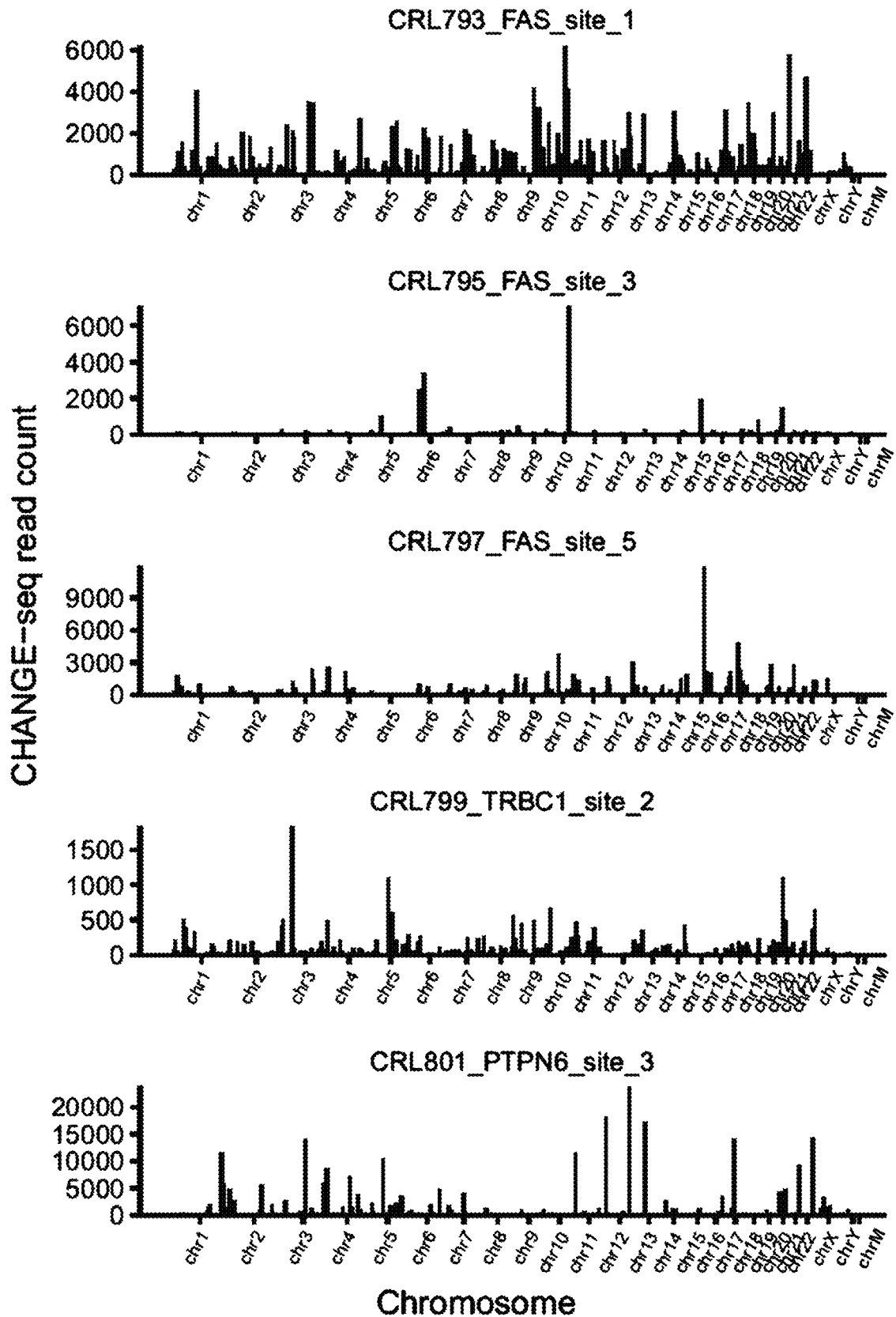
Figure 13A:
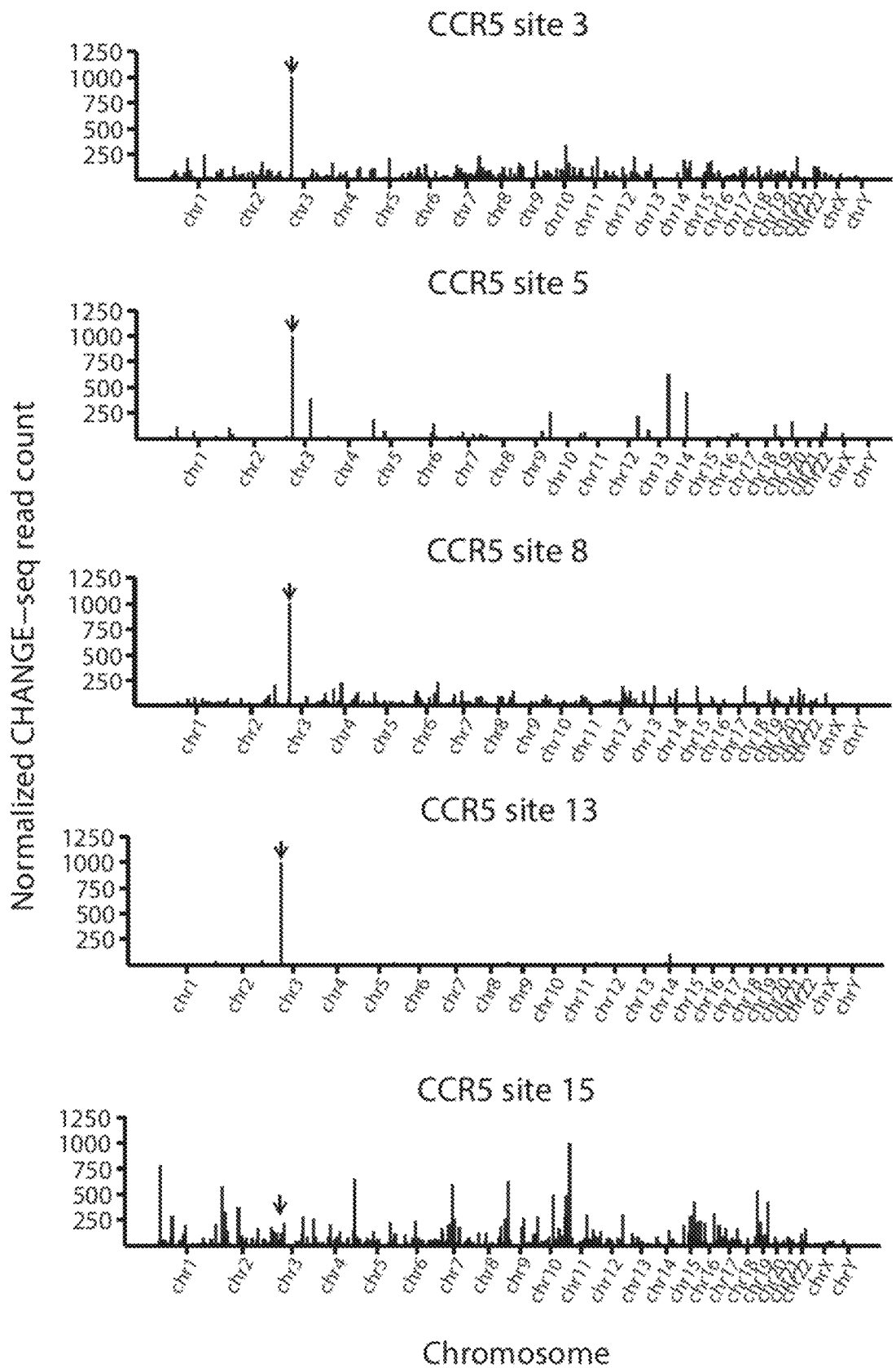
FIGS. 13A-13V. Manhattan plots of CHANGE-seq data for 110 Cas9 gRNAs targeted against 13 human genes. Data show normalized CHANGE-seq read counts plotted by chromosomal position. Arrow marks the intended on-target site.
Figure 13B:
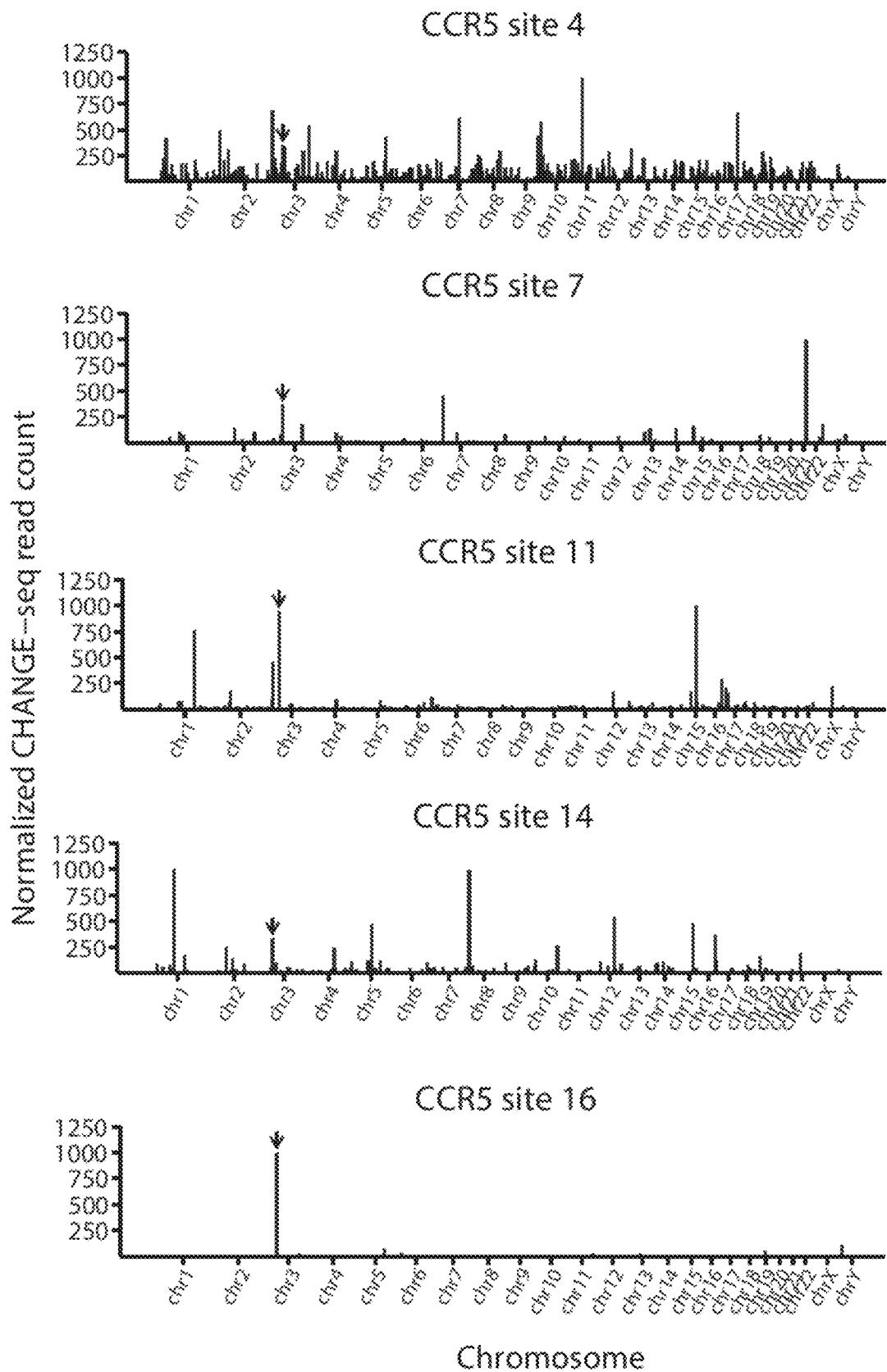
Figure 13C:
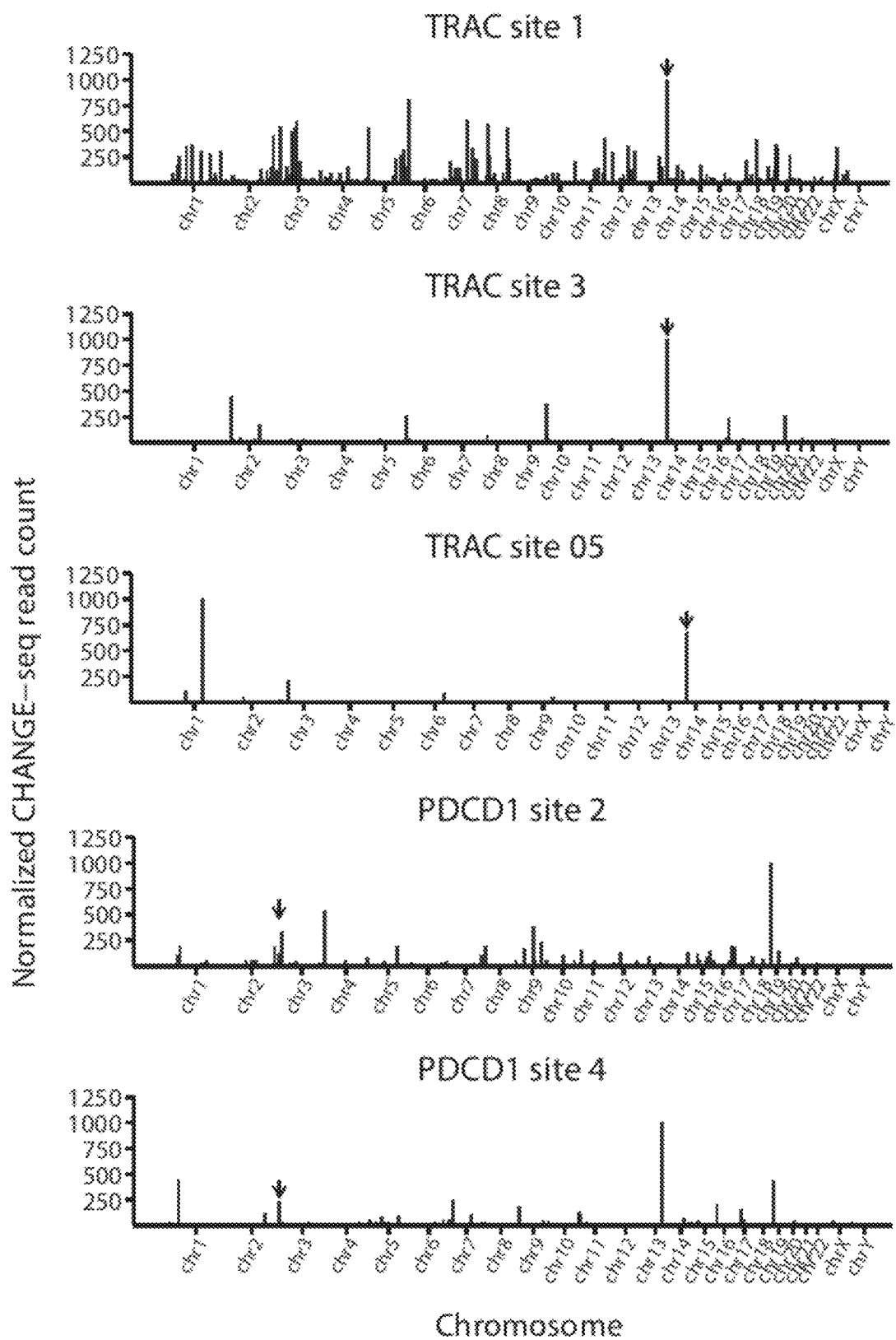
Figure 13D:
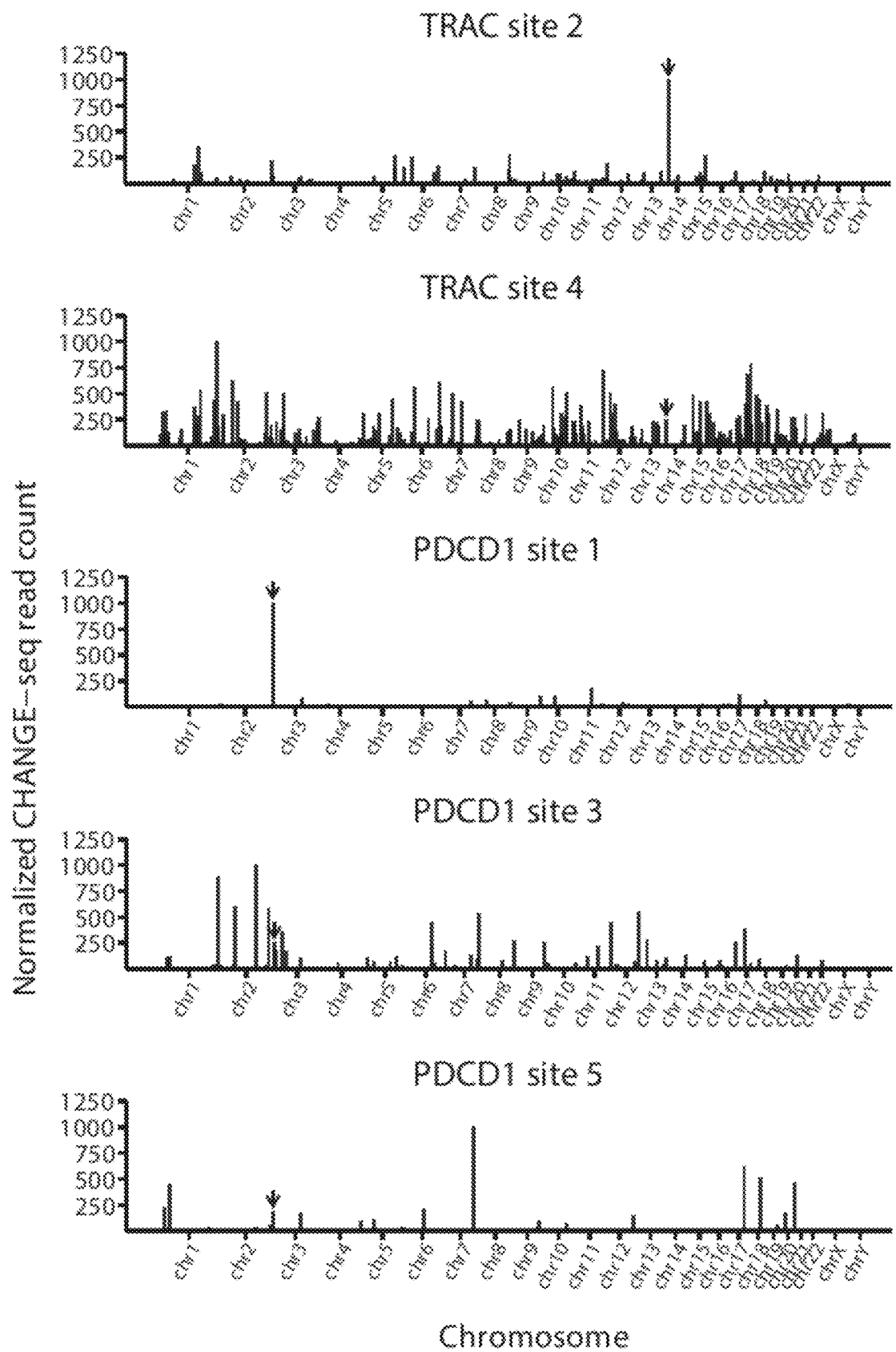
Figure 13E:
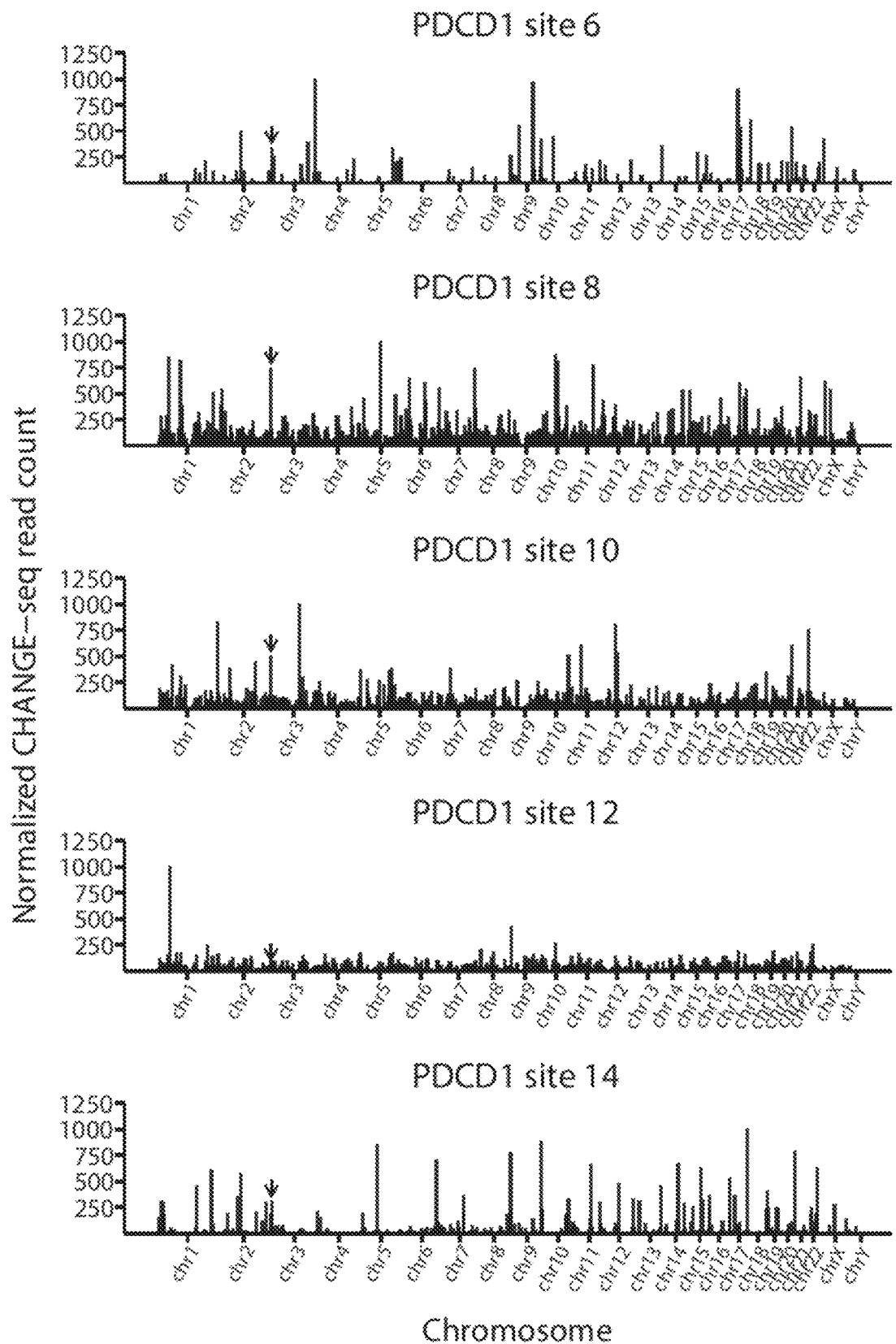
Figure 13F:
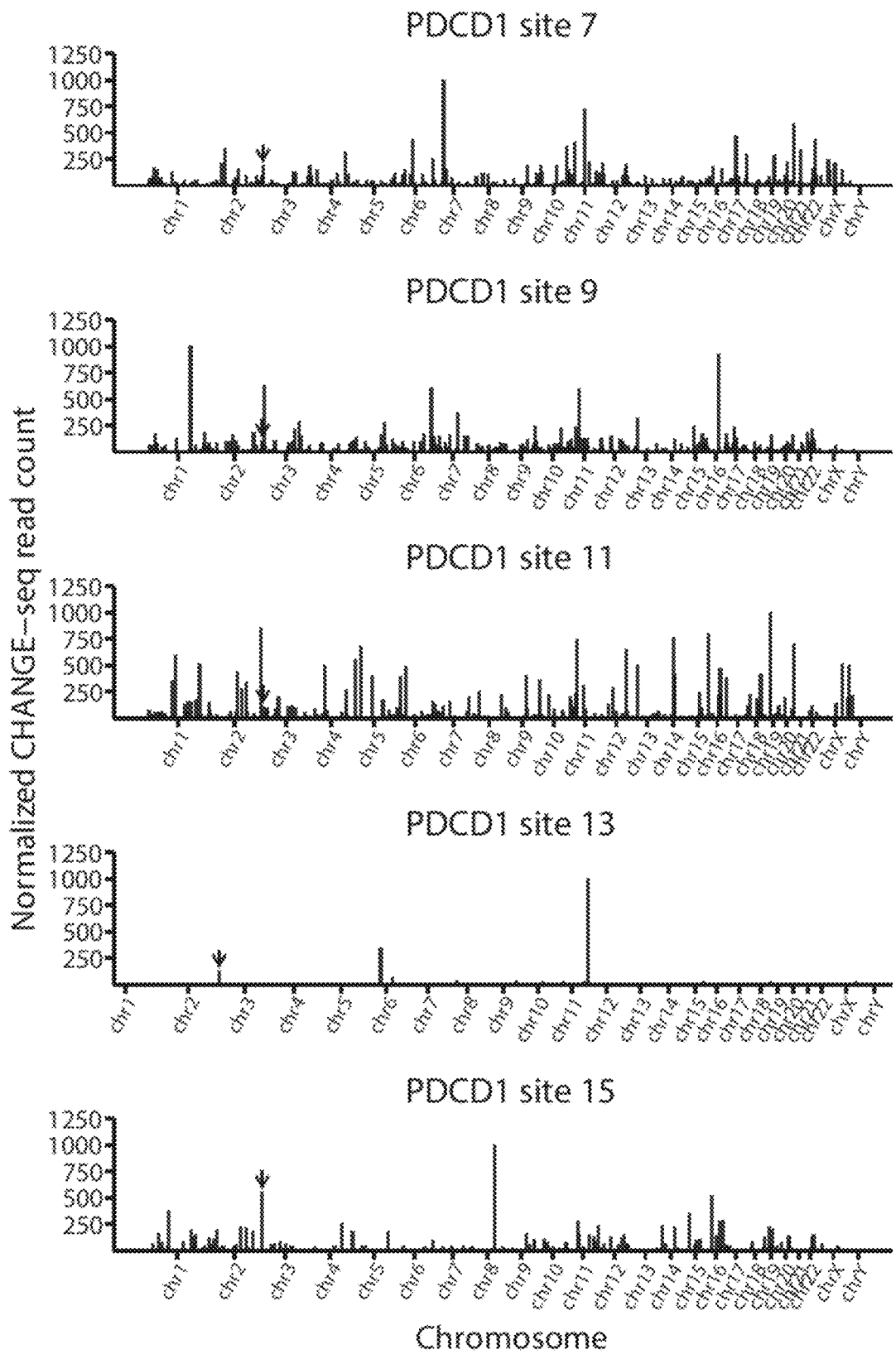
Figure 13G:
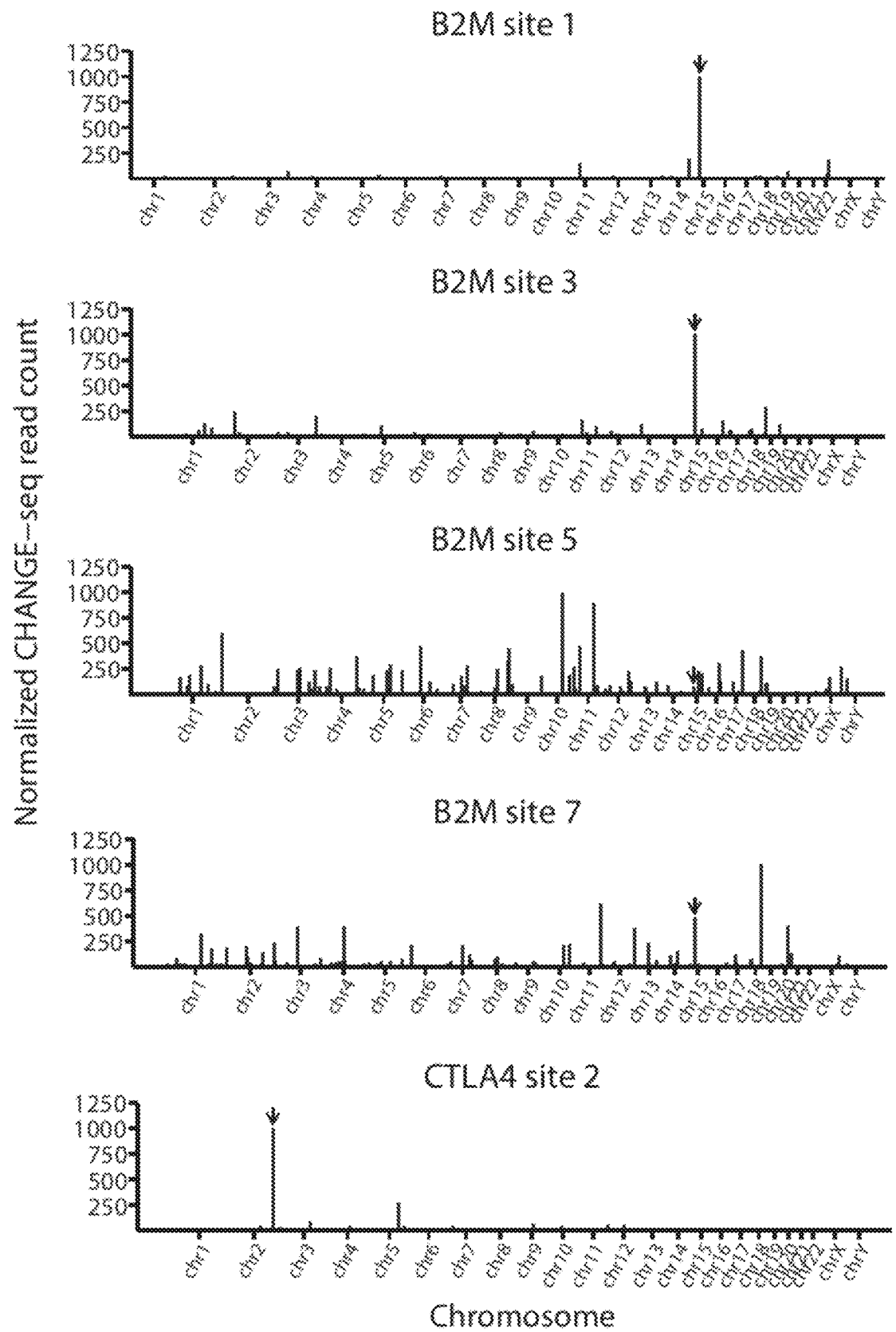
Figure 13H:
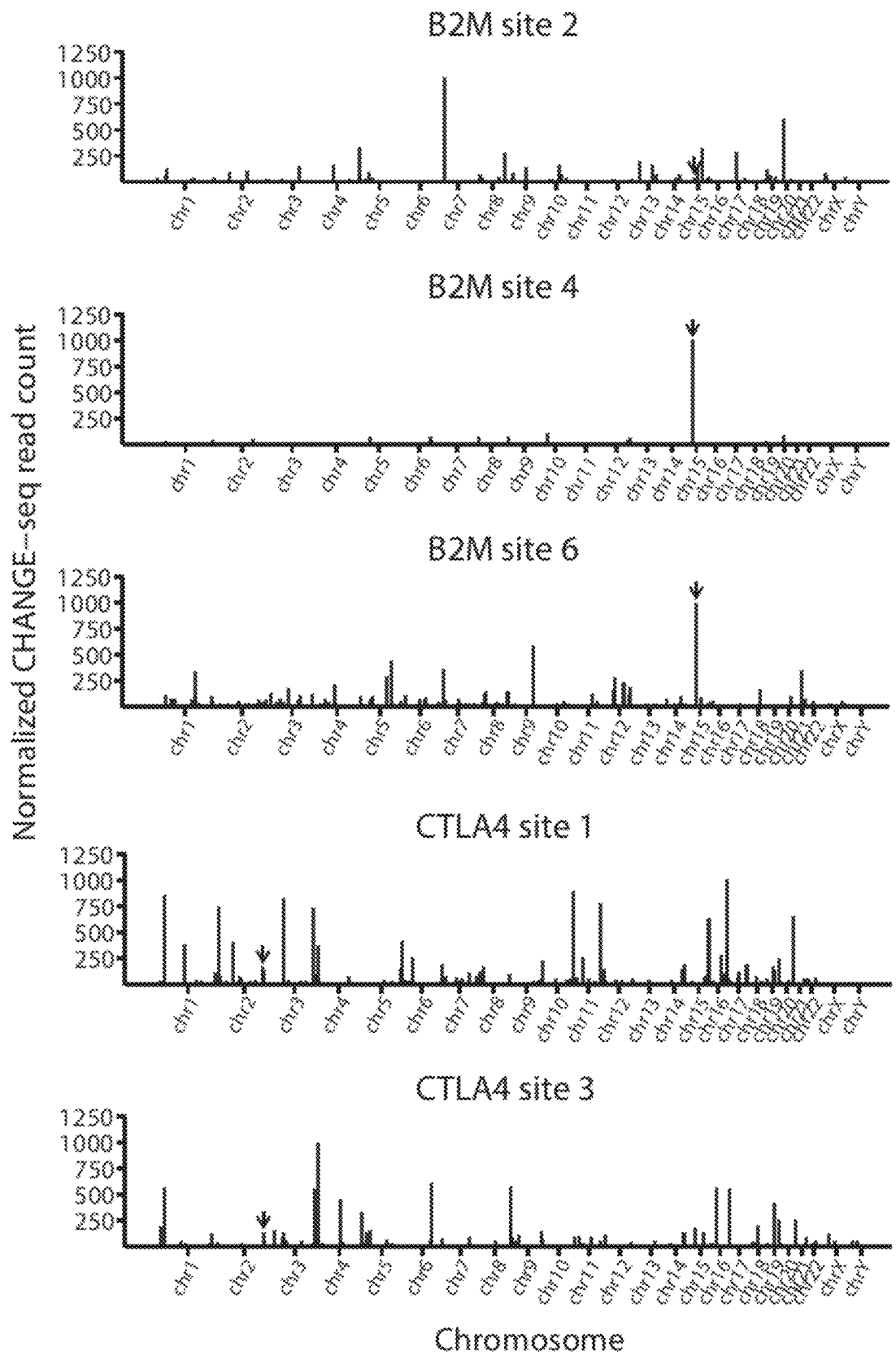
Figure 13I:
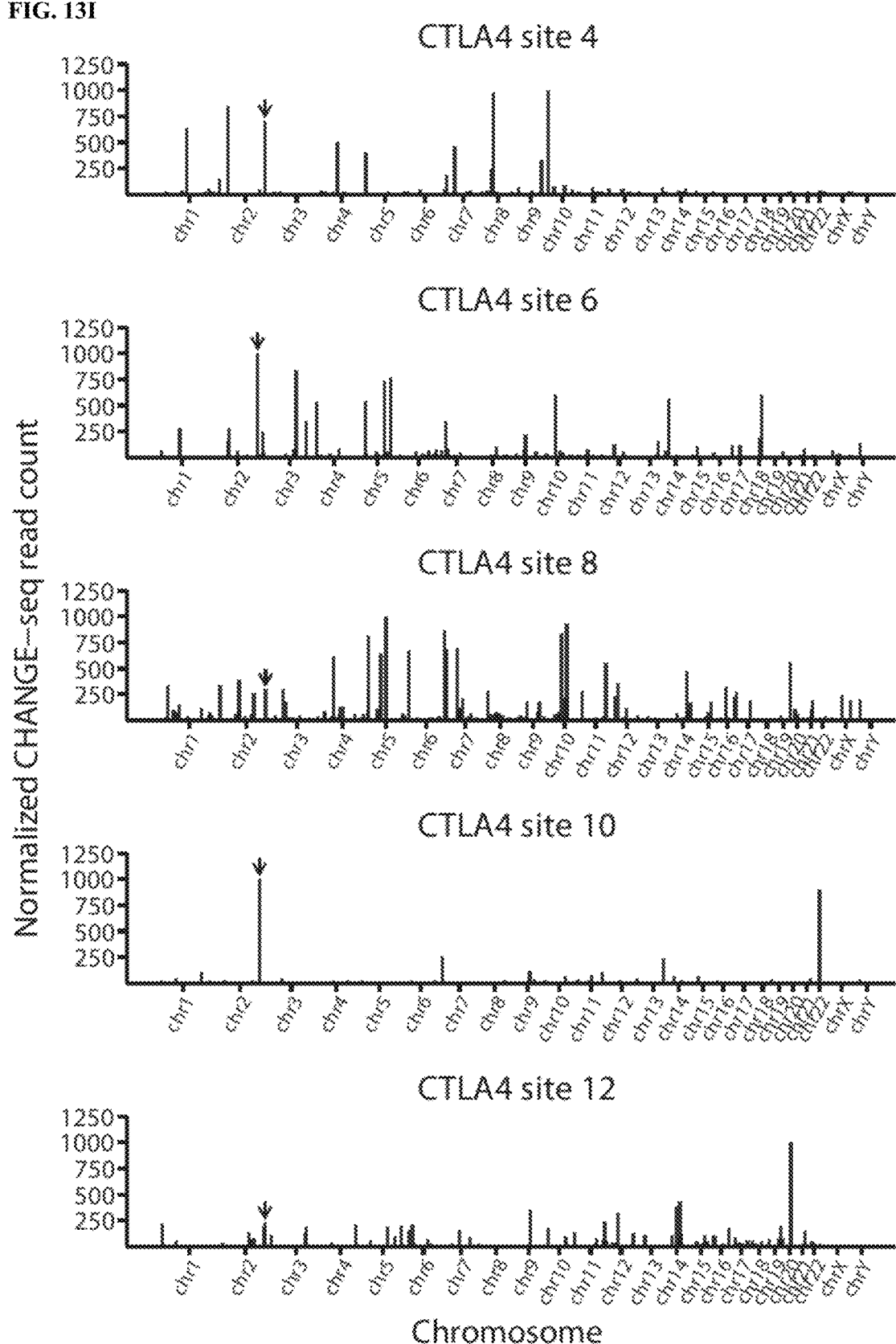
Figure 13J:
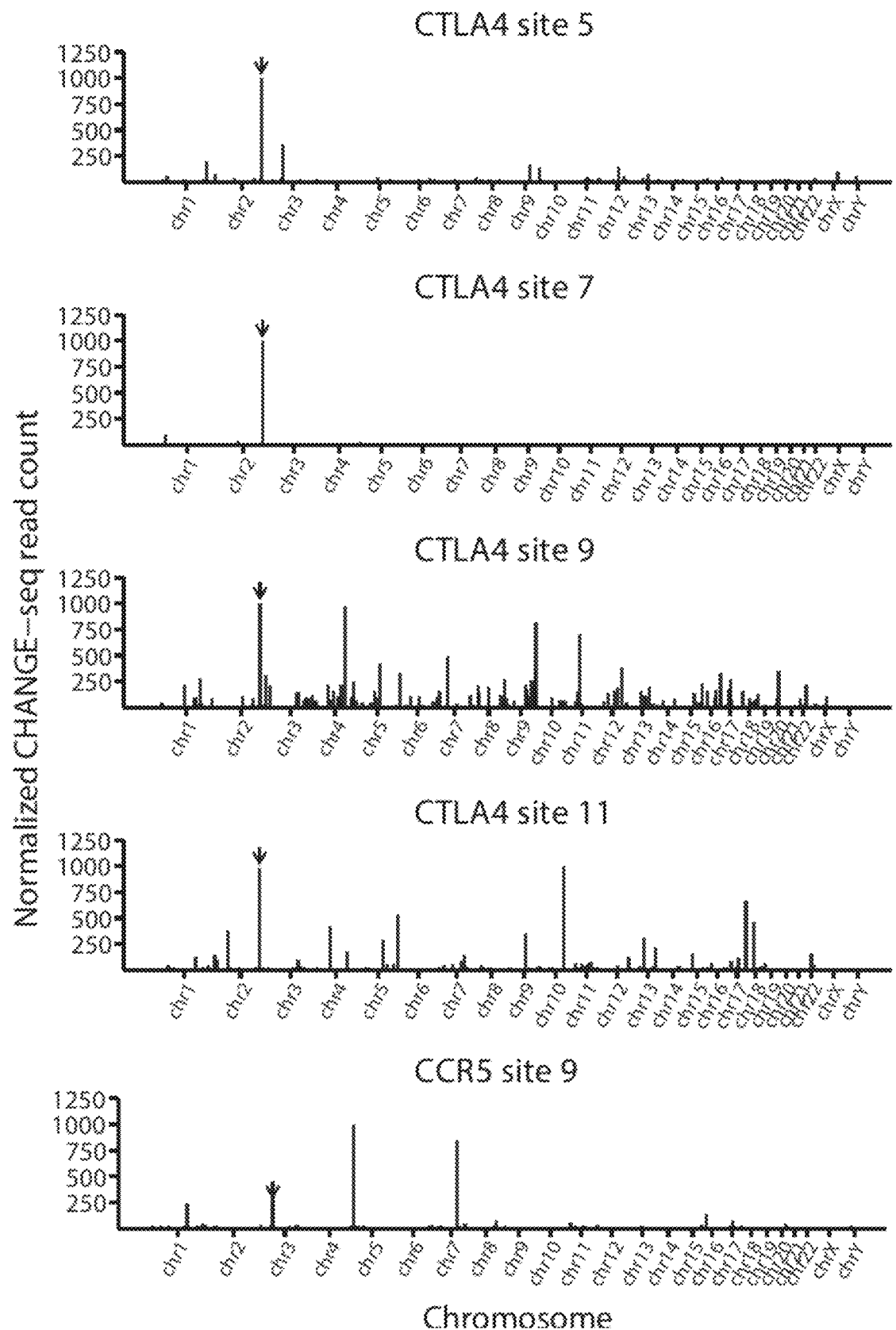
Figure 13K:
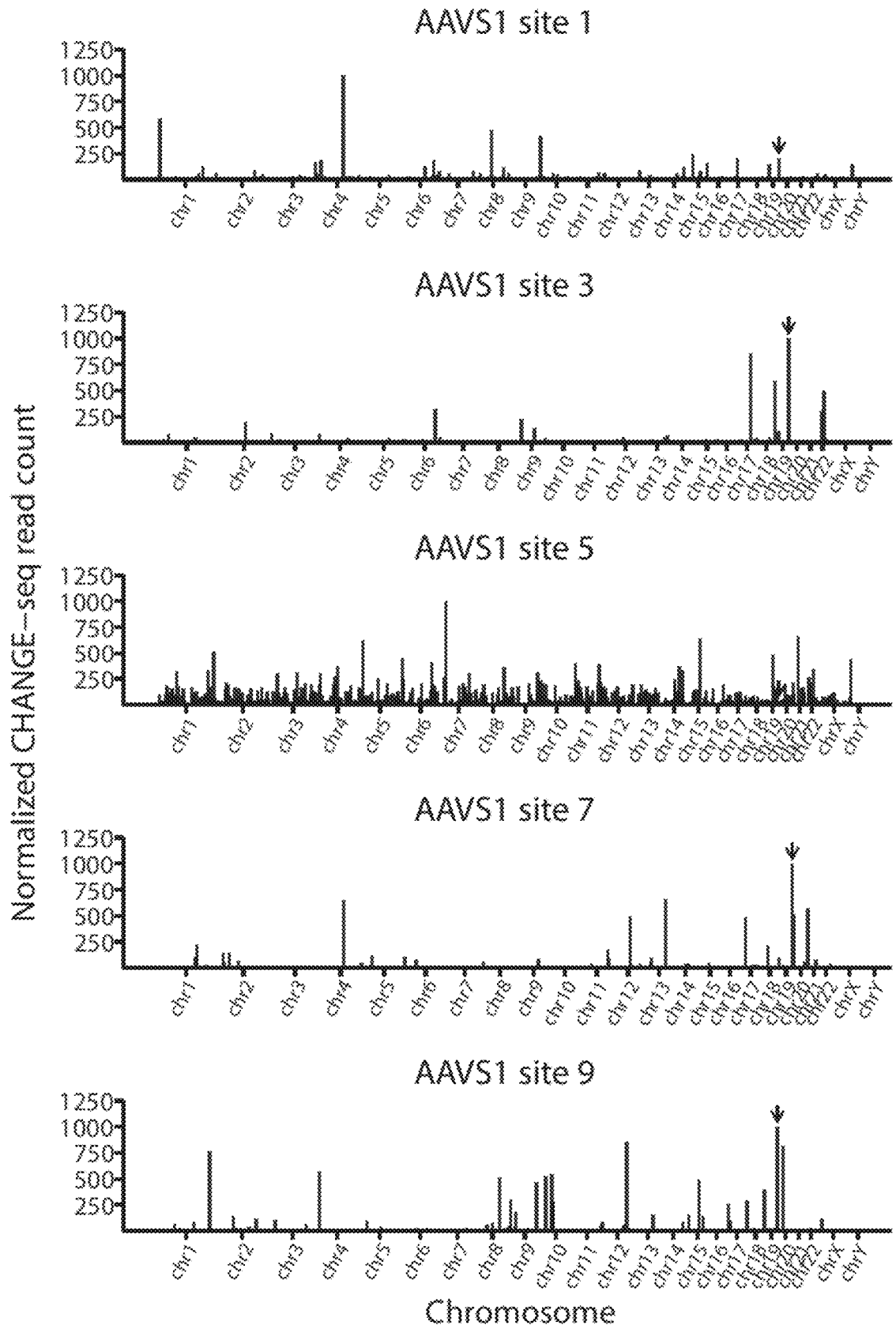
Figure 13L:
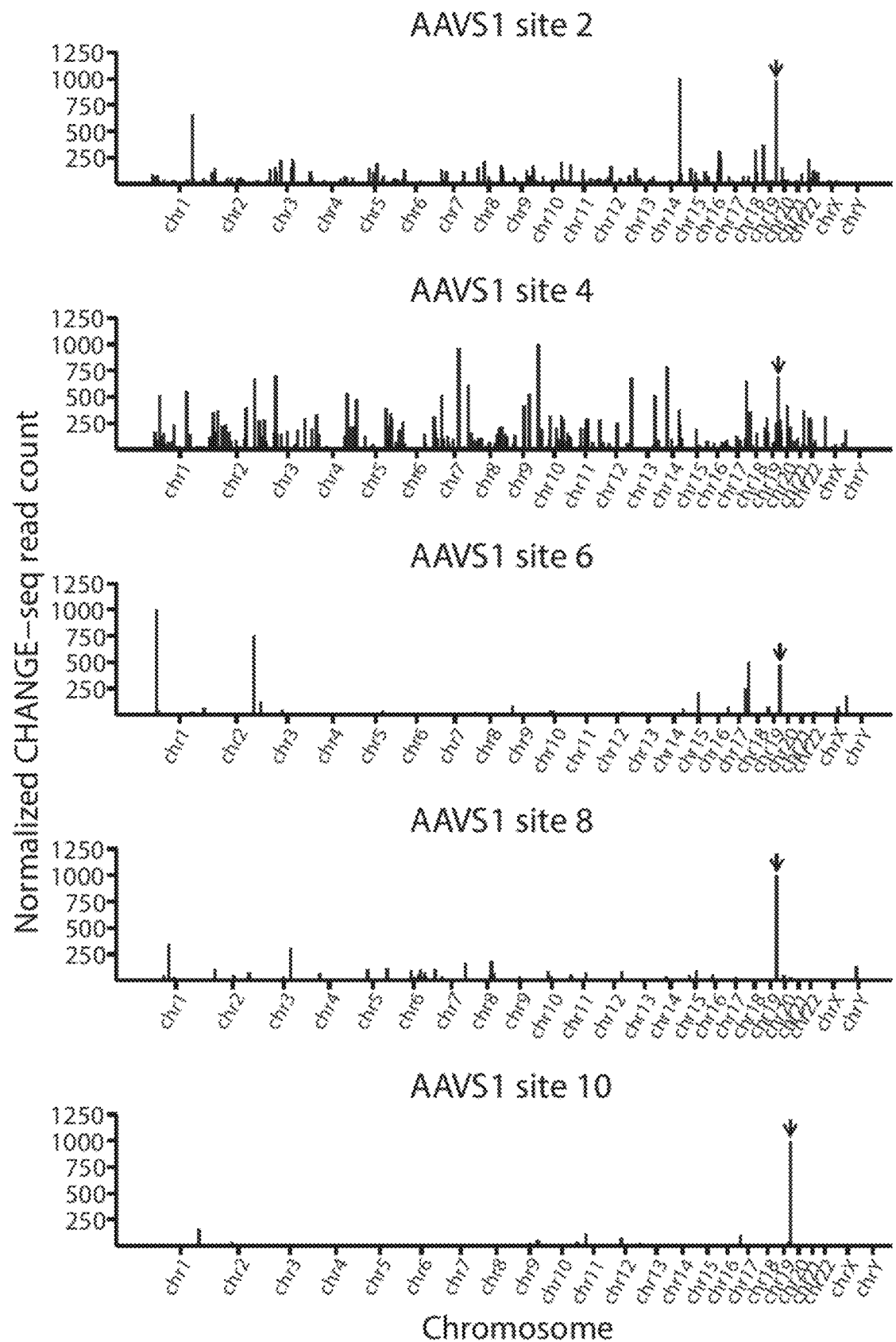
Figure 13M:
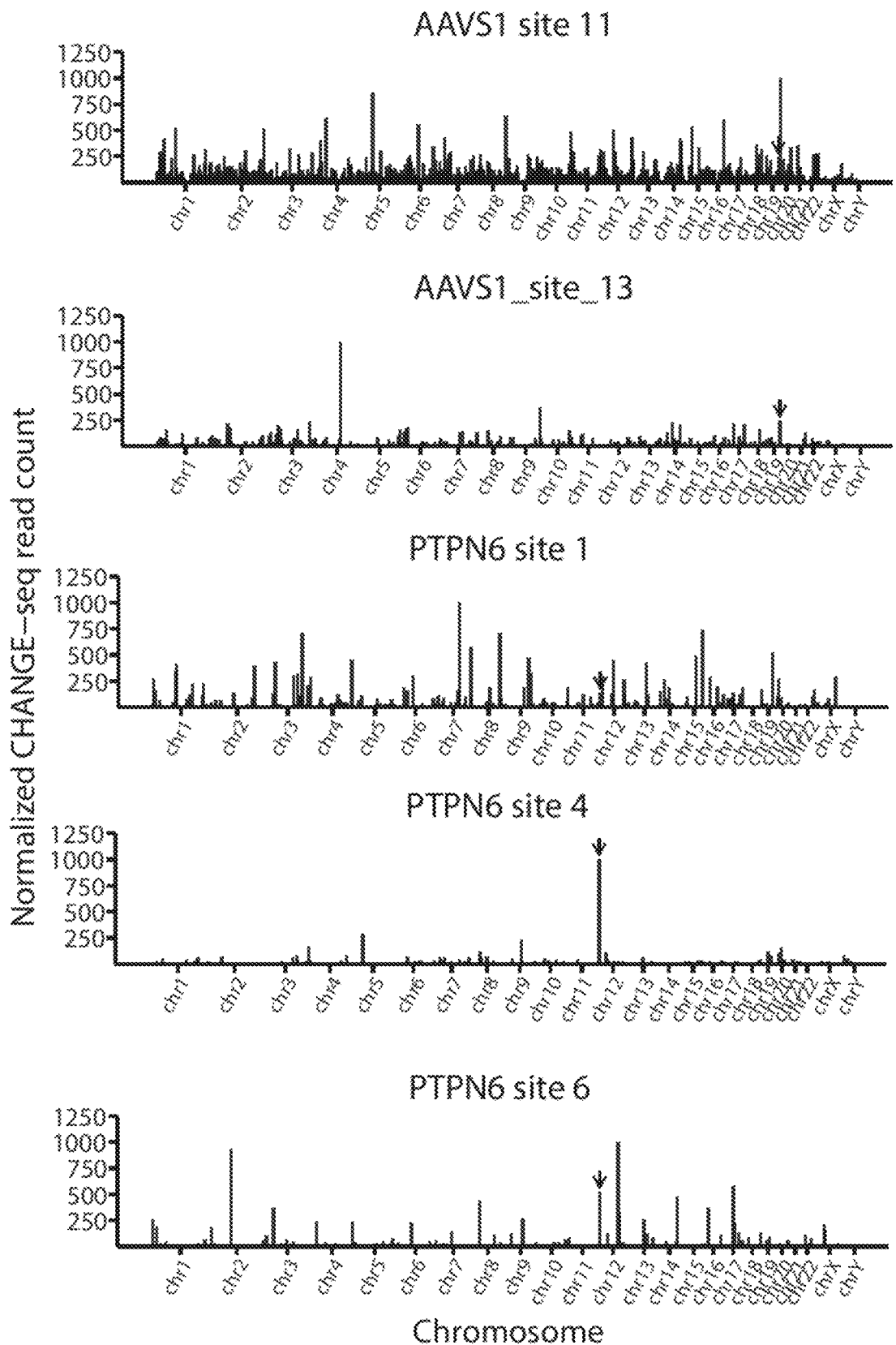
Figure 13N:
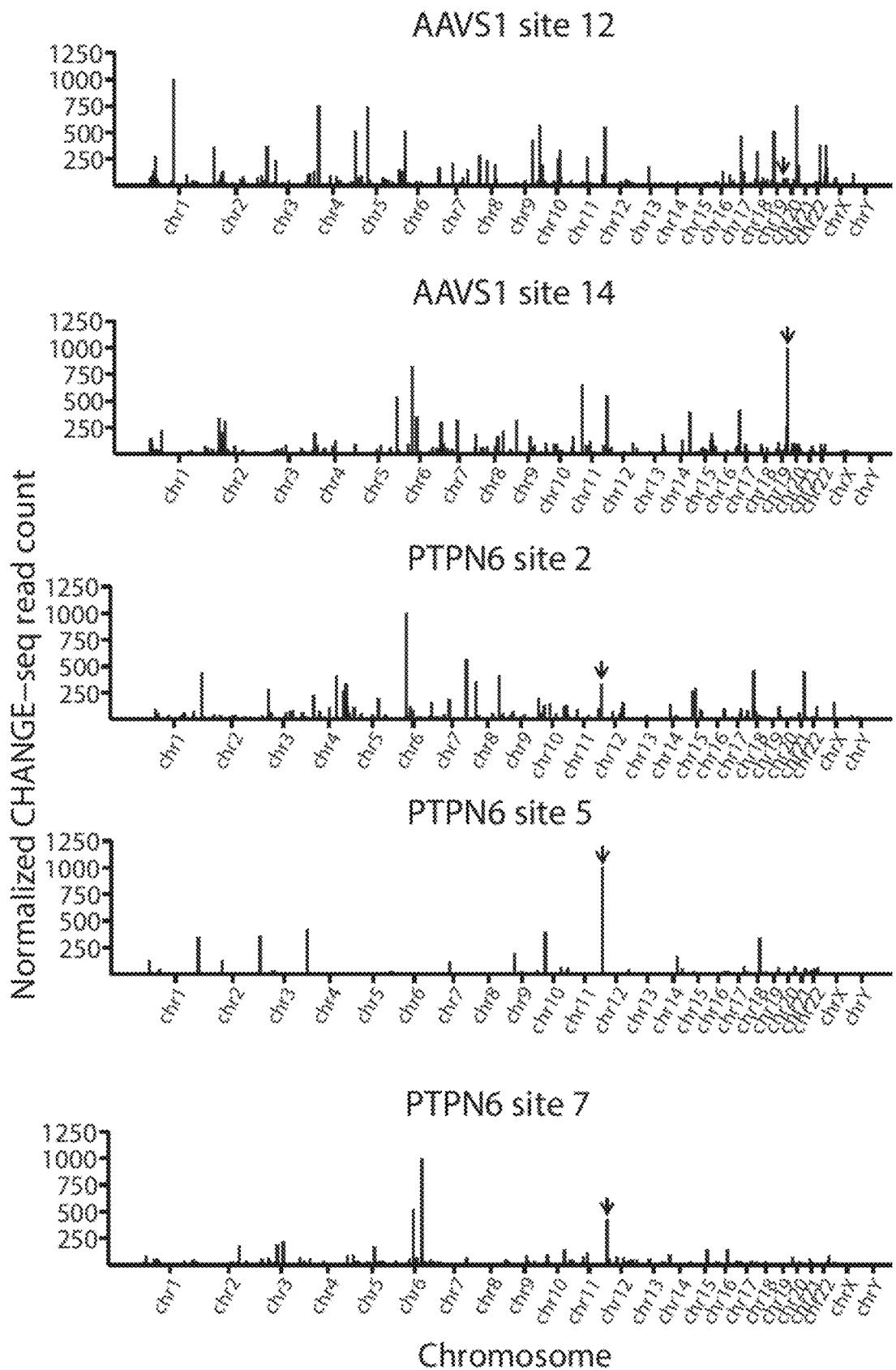
Figure 13O:
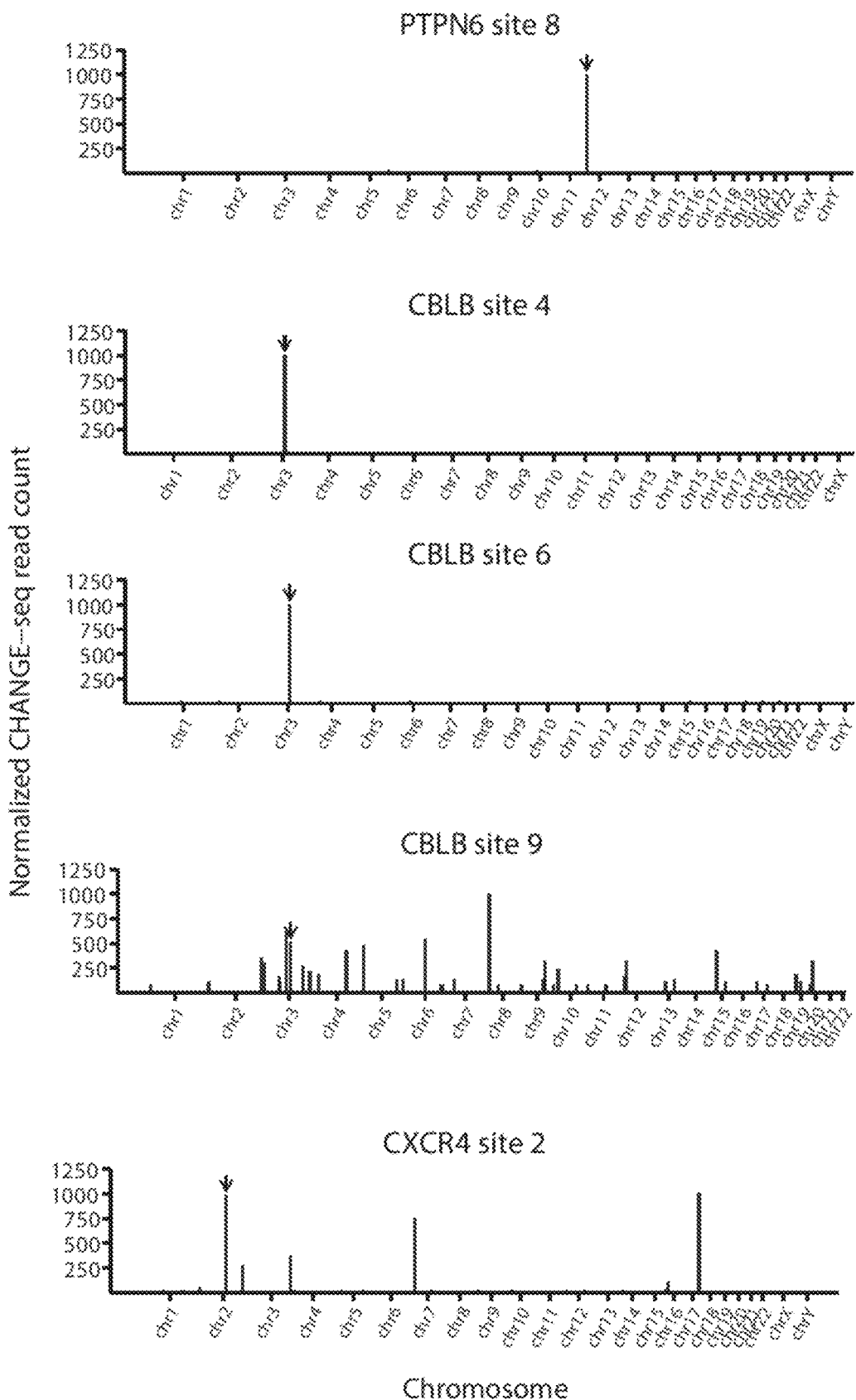
Figure 13P:
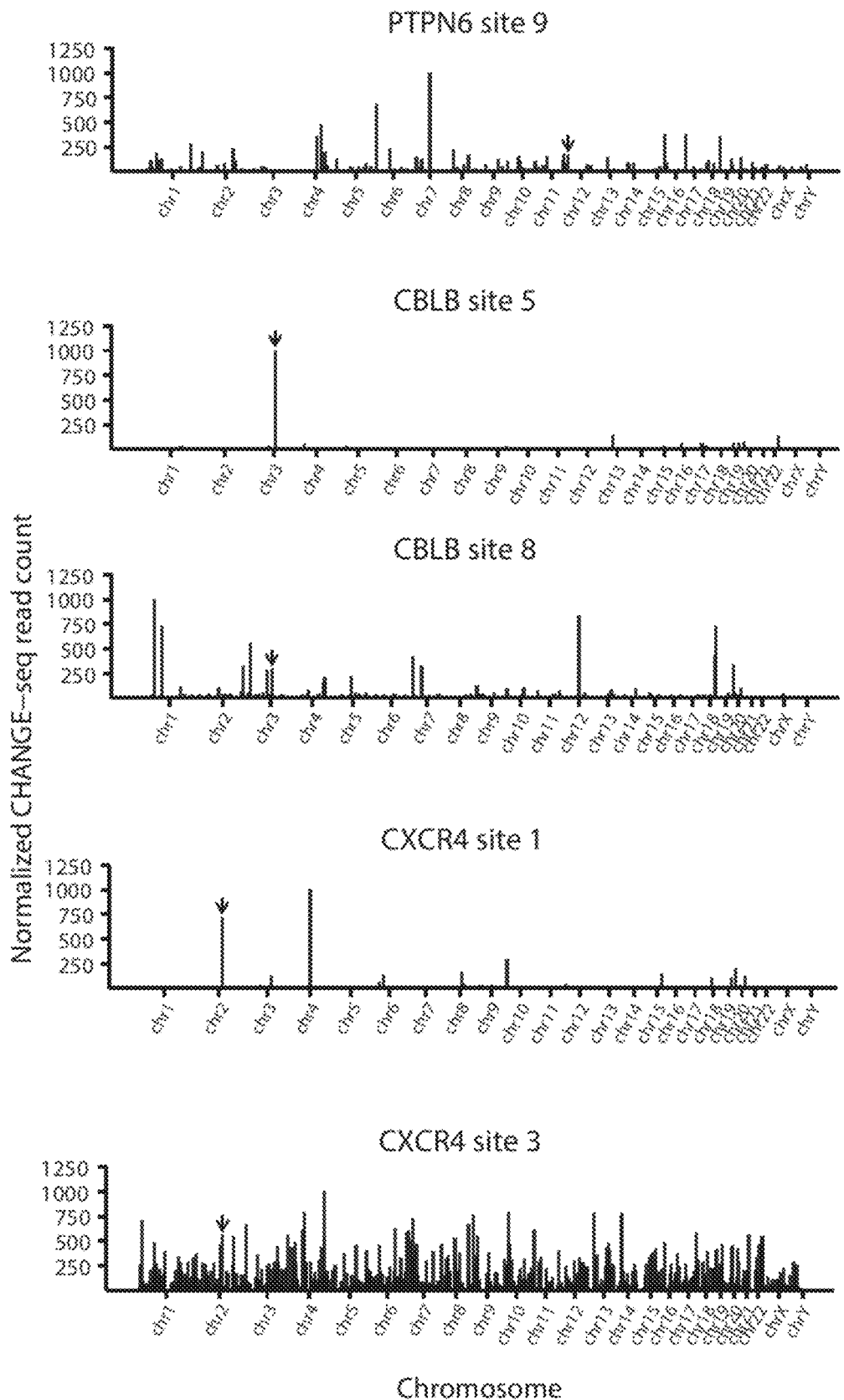
Figure 13Q:
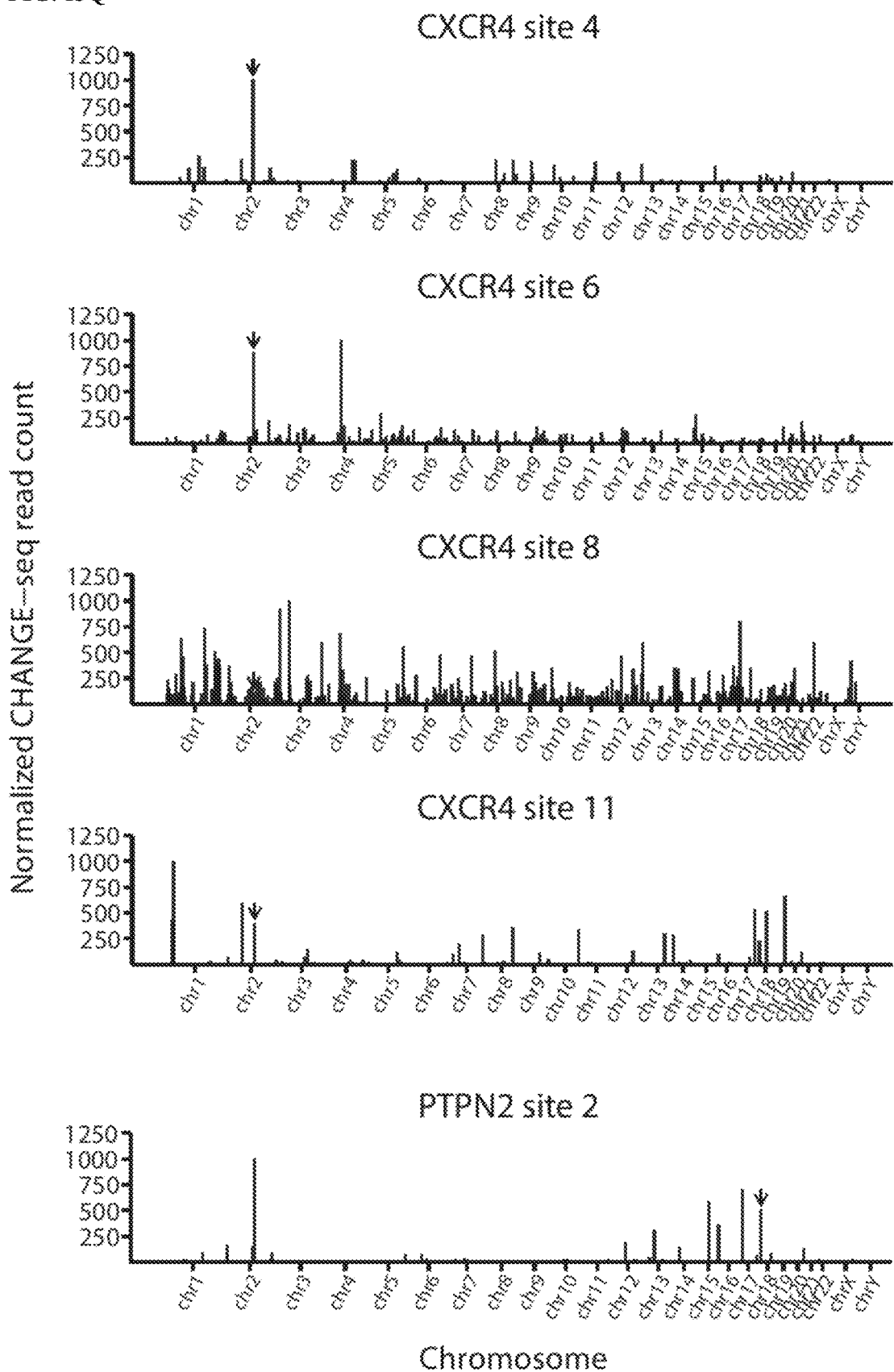
Figure 13R:
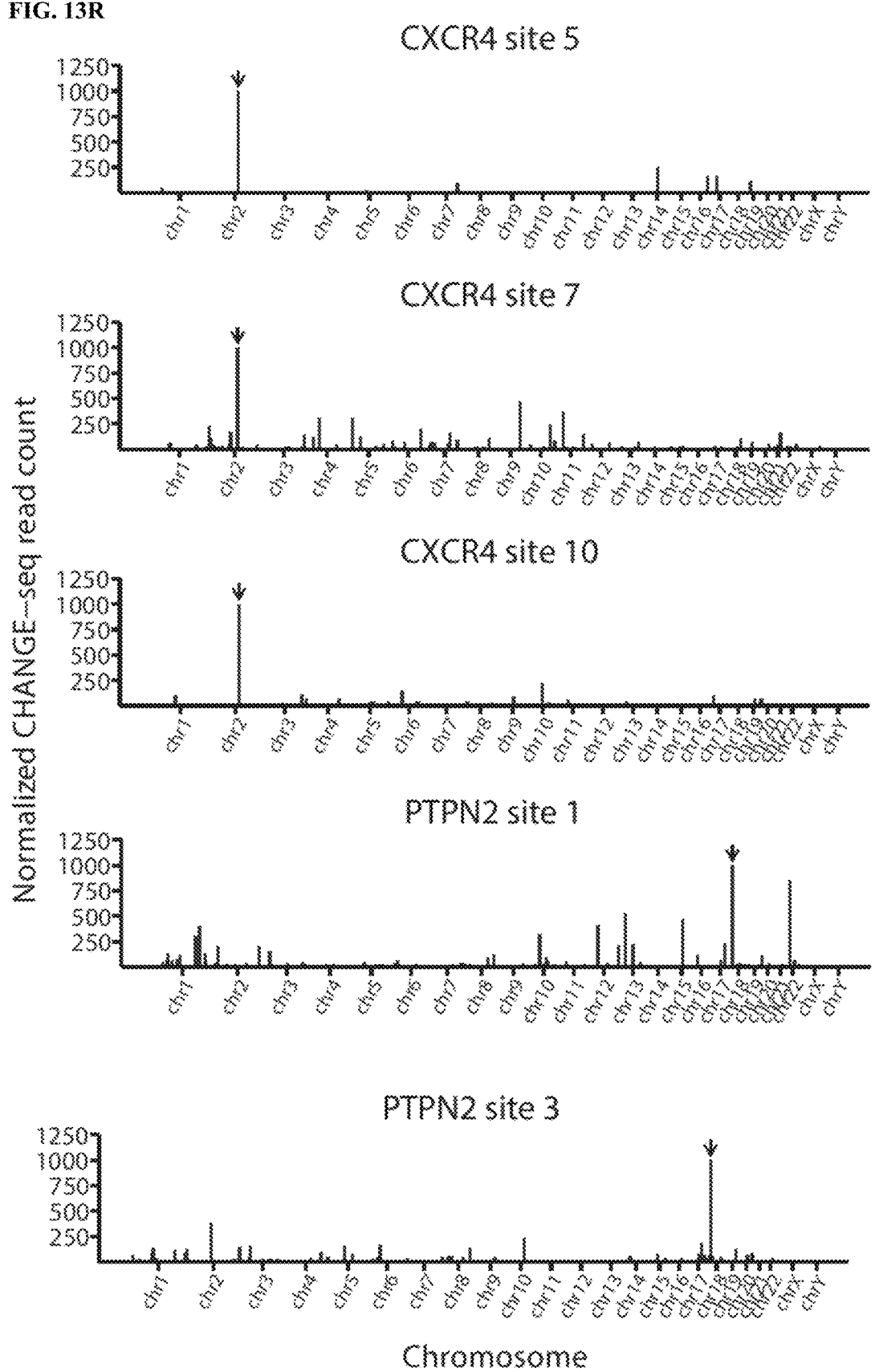
Figure 13S:
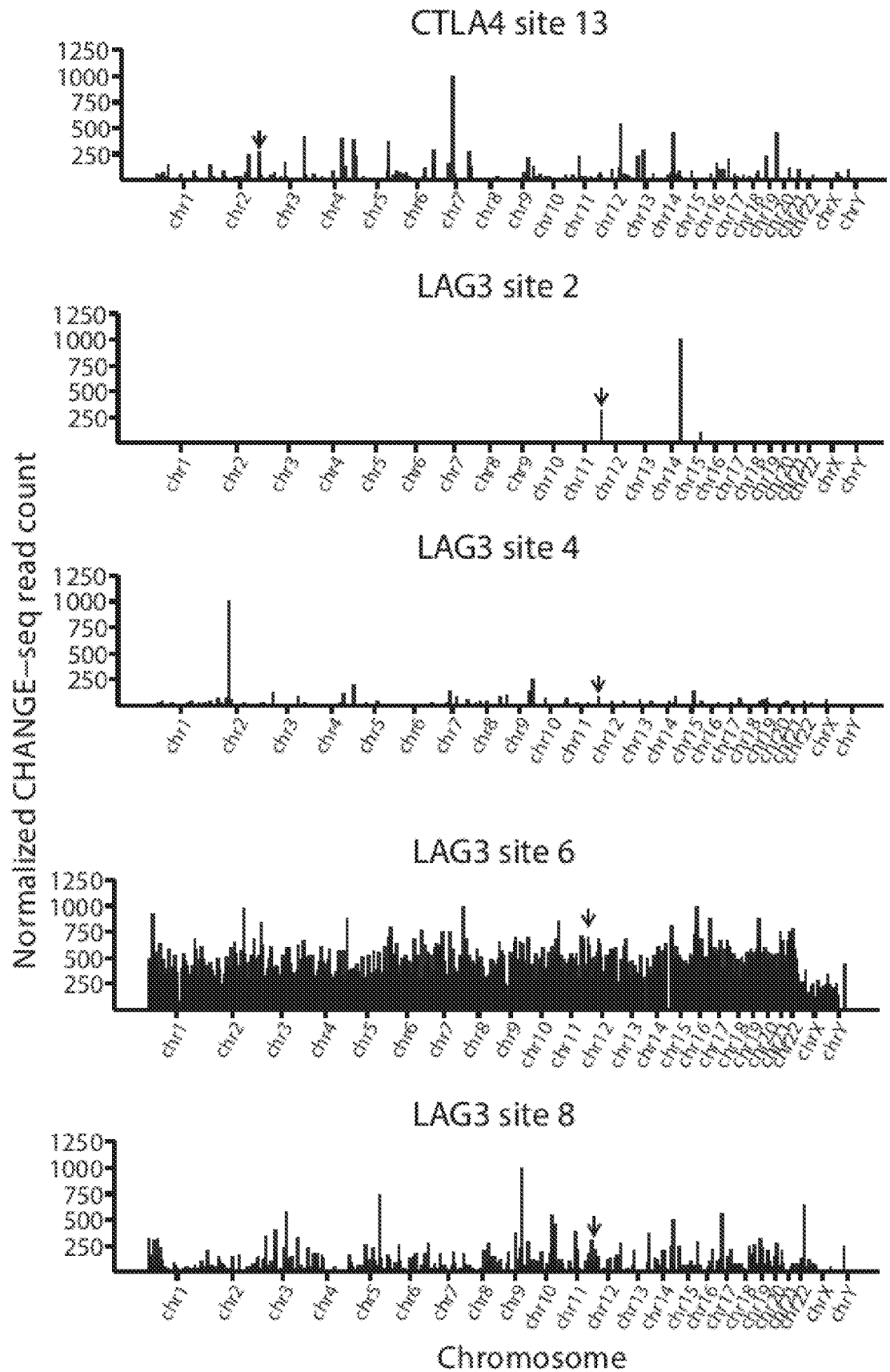
Figure 13T:
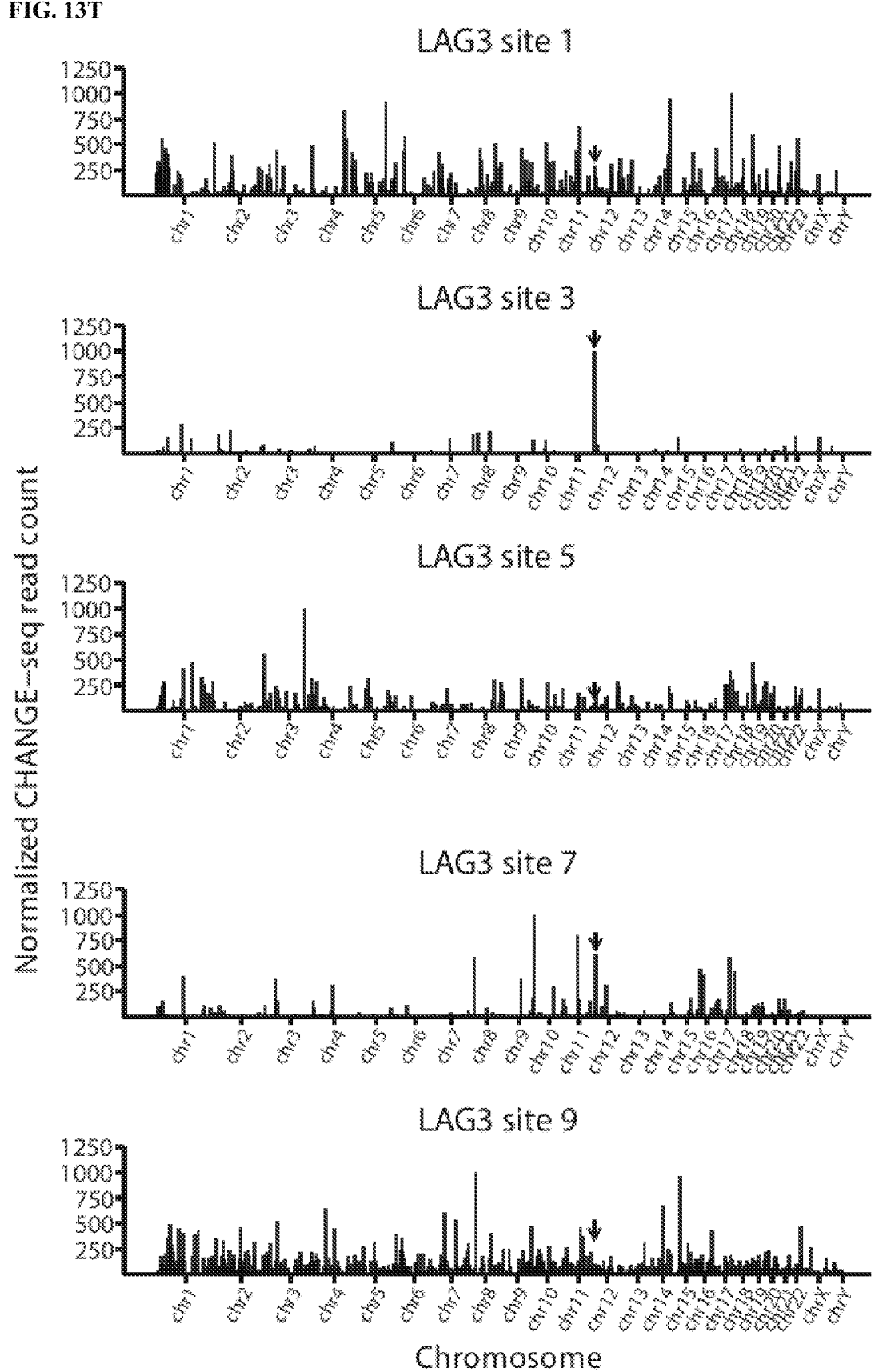
Figure 13U:
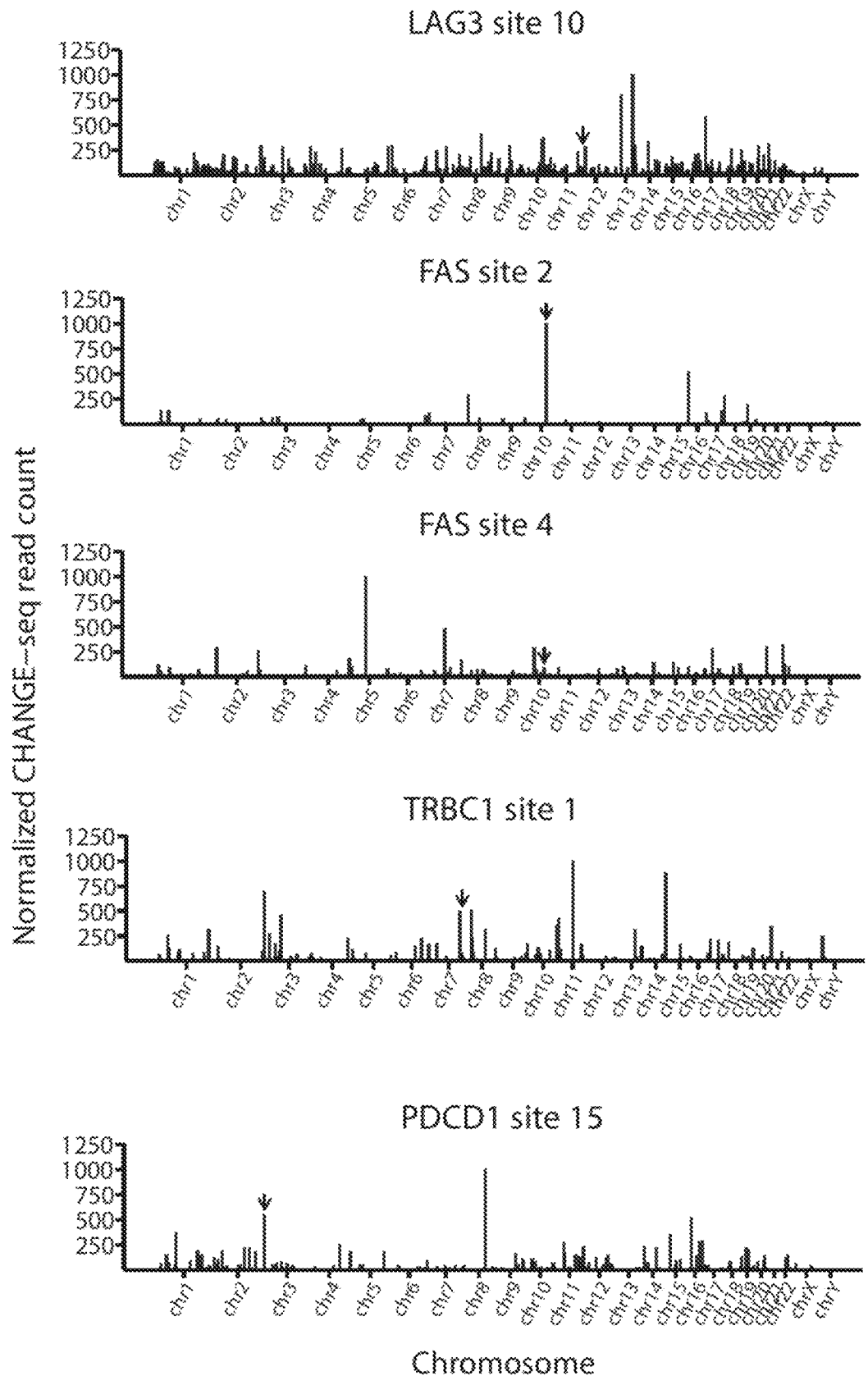
Figure 13V:
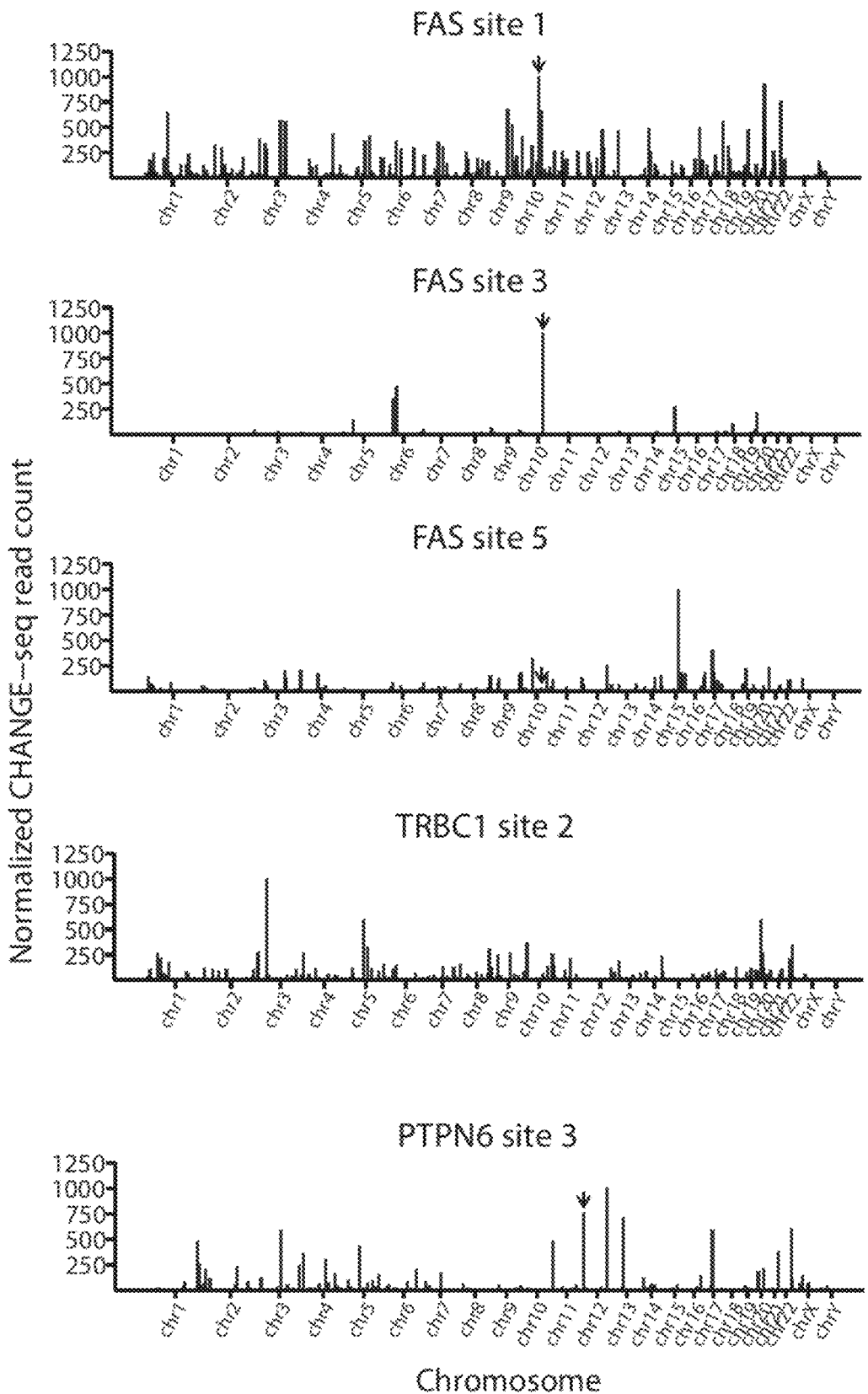

The inventors have generated data, CHANGE-seq profiles at 8 target sites in CCR5. PD-1, and the TRAC locus, that firmly established feasibility of the invented high-throughput approach. There was a wide range of detectable off-target activity detected across these 8 sites and interesting position-specific patterns of tolerance (see FIGS. 1A-1F). The number of sites detected by CHANGE-seq and the overlap between CHANGE-seq and CIRCLE-seq exceeds that of CIRCLE-seq technical replicates (see FIGS. 8-10).

Furthermore, the inventors have generated additional data, CHANGE-seq profiles at 110 target sites in 13 genes or loci (CCR5, PDCD1, B2M, CTLA4, AAVS1, PTPN6, CBLB, CXCR4, PTPN2, LAG3, FAS, TRBC1) that establishes the scalability and high-throughput capabilities of the method (see FIGS. 11A-11B, 12A-12V and 13A-13V).

Figure 5:
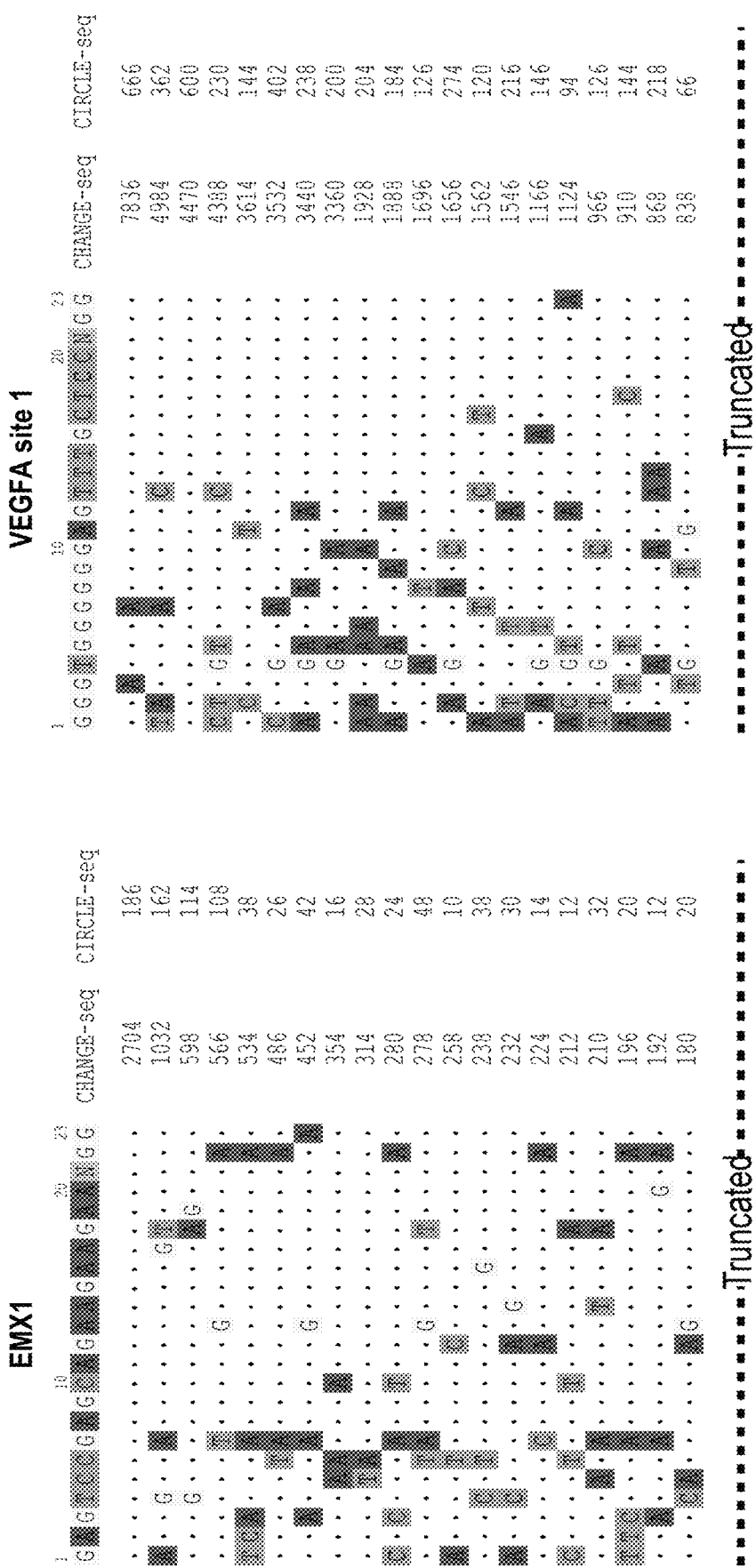
FIG. 5. Visualization of on-target and off-target sites detected by CHANGE-seq and CIRCLE-seq, respectively, targeting EMX1 (SEQ ID NOS 35-55, respectively, in order of appearance) and VEGFA site 1 (SEQ ID NOS 56-76, respectively, in order of appearance). CHANGE-seq shows higher enrichment level than CIRCLE-seq. The intended target site is listed at the top. Each row is a genomic site. Base positions that match the intended target site are indicated with a dot, mismatches are indicated by the nucleotide letter representation (A, C, G, or T). The plots are sorted by read count and truncated where indicated.
Figure 6:
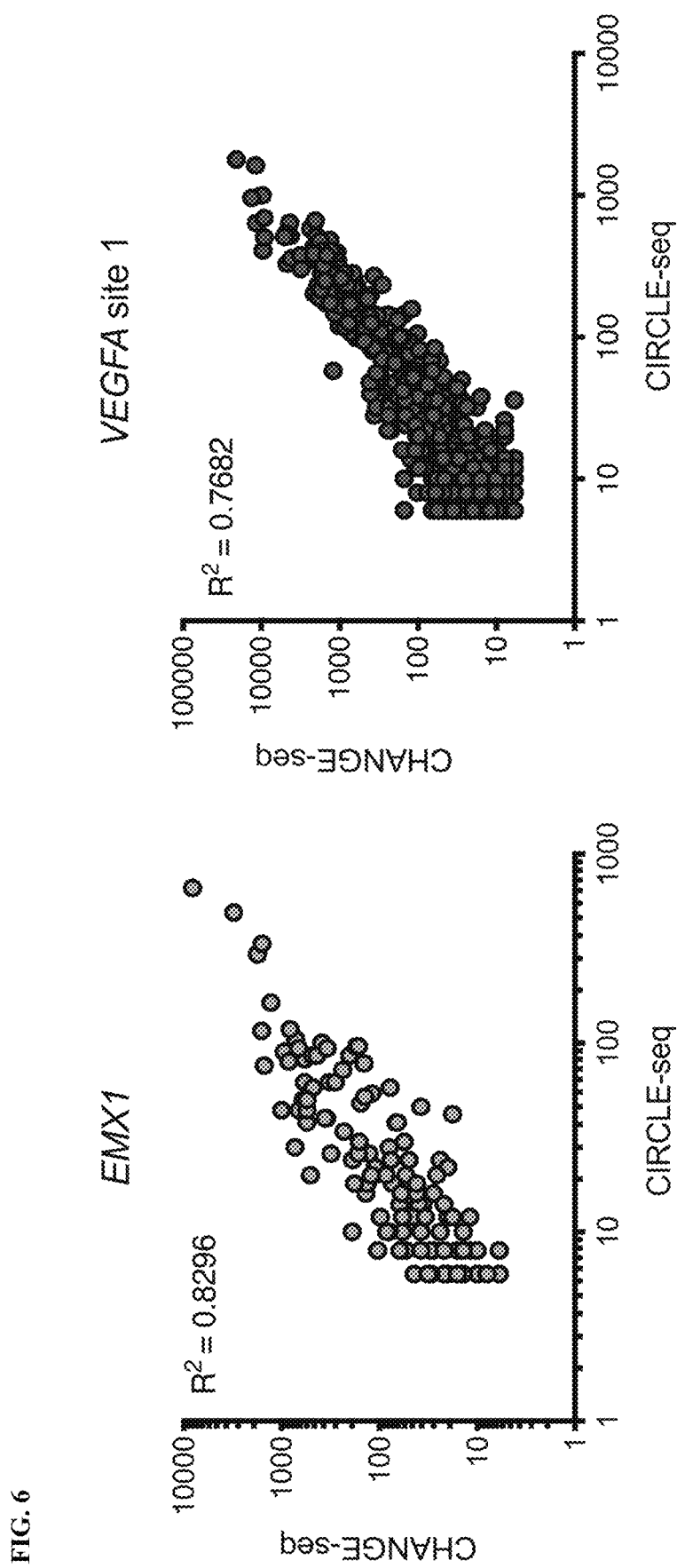
FIG. 6. CHANGE-seq read counts are strongly correlated with CIRCLE-seq read counts. Scatterplots of read counts for CHANGE-seq and CIRCLE-seq methods with libraries prepared from the same source of gDNA (U2OS cells), for sgRNAs targeted against EMX1 and VEGFA site 1.
Figure 7:
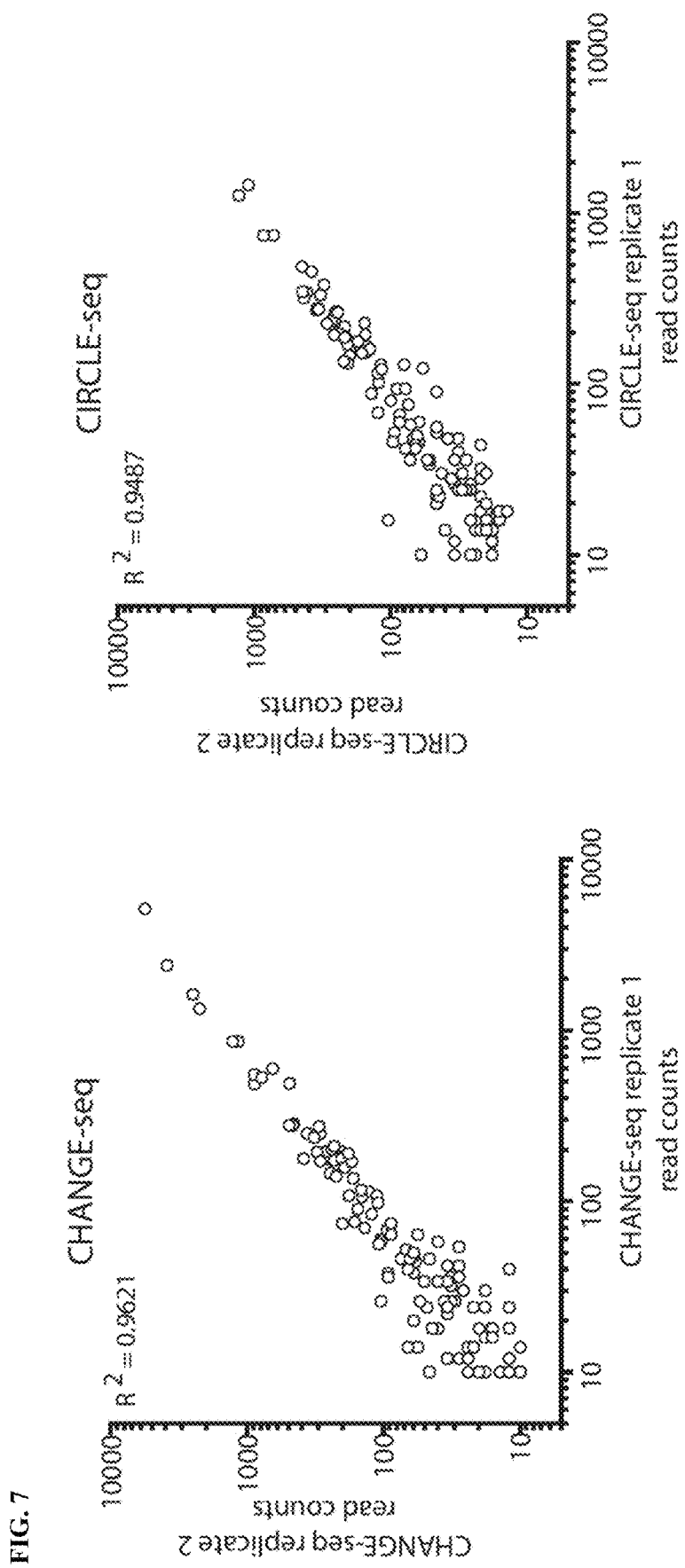
FIG. 7. CHANGE-seq is highly reproducible. Scatterplots of CHANGE-seq and CIRCLE-seq read counts between two CHANGE-seq and two CIRCLE-seq libraries prepared from the same source of gDNA (U2OS cells) for sgRNA targeting EMX1.

CHANGE-seq and CIRCLE-seq read counts are strongly correlated, and CHANGE-seq is highly reproducible (see FIGS. 5-7).

Importantly, the inventors' experimental workflow enables the selective sequencing of any gDNA cleaved by genome editors such as, e.g., Cas9.

Example 2. Extending Discovery Methods to New Genome Editors and Delivery Agents Rationale.

Genome editing technology is rapidly changing, e.g., through discovery of new CRISPR-Cas effectors, the engineering of variants with improved editing properties, and by novel fusions to other DNA-modifying domains. Methods that enable the rapid and systematic comparison of novel genome editors and delivery agents can enable the prioritization of therapeutic strategies that minimize the chance of unwanted adverse effects.

Experimental Studies.

The inventors have established a three-stage recombinant protein expression protocol to produce highly purified, functional S. pyogenes Cas9 protein. The inventors have cloned a series of recombinant protein expression vectors and have used the same system to produce a series of highly pure, active SaCas9-KKH engineered variant, AsCpf1, and LbCpf1 proteins for genome editing. The inventors' protein expression system can enable rapid adoption of new genome editors, by site-directed mutagenesis of the existing vectors or by de novo synthesis and cloning of bacterial codon-optimized coding sequences. By using a standardized protein expression framework, the inventors can ensure that variations in nuclease architecture are not likely to confound experimental comparisons.

Experimental Design.

Cas9 nucleases generally cleave DNA leaving blunt DNA ends; Cpf1 cleaves DNA leaving staggered ends, and base editors produce nicking and deamination. The inventors test various genome editors and delivery strategies.

For Cpf1, an end-repair step can be incorporated after cleavage of purified circularized gDNA by Cpf1 to remove blunt ends using end-repair enzymes such as, e.g., Mung Bean Nuclease or S1 Nuclease (after identifying conditions that can support end-repair without excessively increasing cleavage).

For base editors, enzymatically purified circular gDNA can be treated with base editor protein and an additional enzyme that can introduce a break at the site of deaminated bases. For C→T base editors, base edited gDNA can be treated with USER enzyme (a blend of uracil DNA glycosylase and endonuclease VIII, New England Biolabs, NEB) that is known to cleave DNA at uracil, the product of deaminated cytosine. For A→G base editors, base edited gDNA can be treated with endonuclease V, which cleaves at inosine, the product of deaminated adenosine.

The above methods can produce large-scale datasets that describe the genome-wide activity of various genome editors allowing to make generalizations about their relative specificities.

Example 3. CHANGE-seq Protocol

Reagent Setup

Anneal Mosaic End Double-Stranded (MEDS) Oligonucleotides

```
oCRL225
                                      (SEQ ID NO: 1)
/5Phos/ACG/ideoxyU/AGATGTGTATAAGAGACAG oCRL226
                                      (SEQ ID NO: 2)
/5Phos/CTGTCTCTTATACACATCTACGT
```

/5Phos/ indicates 5' phosphorylation and /ideoxyU/ indicates internal dexoyUridine.

| Component | Volume (µl) |
| --- | --- |
| oCRL225 100 µM | 50 |
| oCRL226 100 µM | 50 |
| Total | 100 |

Tn5 Expression and Purification

Tn5 is expressed and purified according to Picelli et al 2014 (Picelli et al., Genome Research, 2014, 24(12):2033-40), with modifications. Transform the pTXB1 plasmid (Addgene in Rosetta (DE3)pLysS competent cells (Novagen) and grow the culture at 37° C. to A600=0.9, chill to 10° C. and induce the Tn5 expression with IPTG at 0.25 mM final concentration, at 23° C. for 4 h. Lyse the cells by sonication in HEGX (20 mM HEPES-KOH at pH 7.2, 0.8M NaCl, 1 mM EDTA, 10% glycerol, 0.2% Triton X-100), with complete protease inhibitors (Roche). Pellet the lysate, neutralize the supernatant with 10% of PEI (Sigma) and remove the precipitate by centrifugation. Load the supernatant on a chitin column in HEGX with complete protease inhibitor. Wash the column with HEGX. Then, add HEGX with 100 mM DTT on the top of the column, and let 11 ml of buffer to drain out of the column. Leave the column closed for 36-48 h at 4° C. to effect cleavage of Tn5 from the intein. Dialyze the purified Tn5 against 2×Tn5 dialysis buffer (100 mM HEPES-KOH at pH 7.2, 0.2M NaCl, 0.2 mM EDTA, 2 mM DTT, 0.2% Triton X-100, 20% glycerol) and quantify by BCA. For preparing a 55% glycerol stock of unassembled Tn5, bring the dialyzed Tn5 concentration to 4.5 mg/ml, add 1.1 vol 100% glycerol and 0.33 vol of 2×Tn5 dialysis buffer to the dialyzed Tn5 preparation. Make 1 ml aliquots and store at −20° C.

2×Tn5 Dialysis Buffer 100 mM Hepes-KOH, pH 7.2, 0.2 M NaCl, 0.2 mM EDTA, 2 mM DTT, 0.2% Triton X-100, 20% glycerol Transposome Complex Assembly

| Component | Volume (µl) |
| --- | --- |
| Tn5 (1.85 mg/ml) | 360 |
| Annealed oCRL225/oCRL226-MEDS (25 µM) | 150 |
| 2X Tn5 dialysis buffer | 520 |
| Total | 1030 |

Incubate at room temperature for 1 hour and then store at −20° C.

5×TAPS-DMF Buffer 50 mM TAPS-NaOH pH 8.5, 25 mM $MgCl_2$, 50% v/v DMF.

SPRI-Guanidine Binding Buffer 4M guanidine thiocyanate, 40 mM TRIS, 17.6 mM EDTA, pH 8.0. TRIS 1M pH 8 and EDTA 0.5M pH 8 can be added to the 4M guanidine (after the guanidine is solubilized in water—add the proper volume for getting the right final concentration) and then the pH will be very close to 8. Bring the pH to 8 with HCl.

SPRI Beads Preparation

Add 1 ml of Sera-Mag SpeedBeads (GE) to a 1.5 ml Eppendorf tube. Place in a magnetic rack. Remove the liquid. Remove the tube from the rack. Add 1 ml of TE and homogenize. Place back in the magnetic rack and remove the liquid. Repeat this step for a total of two TE washes. Then, add 1 ml of TE.

SPRI-Guanidine Beads Preparation

Add SPRI-guanidine binding buffer to 9 g of PEG 8000 up to 39 ml and then add 10 ml of 5M NaCl. Homogenize during 3-5 min. Add 1 ml of Sera-Mag SpeedBeads in TE (as described in SPRI beads preparation) and homogenize. Keep at 4° C.

Procedure

1| Genomic DNA tagmentation. Tn5 reactions are assembled as follows:

| Component | Volume (µl) |
| --- | --- |
| 5x TAPS-DMF buffer | 20 |
| Tn5 preassembled with oCRL225/oCRL226-MEDS | 40 |
| Genomic DNA (50 ng/µl) | 20 |
| $H_2O$ | 20 |
| Total | 100 |

Incubate in a thermocycler at 55° C. for 7 minutes.

2| Dilute proteinase K 1:1 in water and add 5 µl of the diluted proteinase K to the tagmented DNA. Incubate at 55° C. for 15 minutes.

3| Add 1.8× volumes (189 µl) of SPRI-Guanidine beads to the tagmented DNA, mix thoroughly by pipetting 10 times. Incubate at room temperature for 10 minutes. Place the reaction plate onto a Magnum FLX magnetic rack (Alpaqua) for 5 minutes. Remove the cleared solution from the reaction plate and discard. Add 200 µl of 80% ethanol, incubate for 30 seconds and remove the supernatant. Repeat this step for a total of two ethanol washes. Remove ethanol completely and let the samples air dry for 3 minutes on the magnetic rack. Remove the plate from the magnetic rack and add 23 µl of TE pH 8.0, and pipette 10 times to mix. Incubate at room temperature for 2 minutes. Place the reaction plate back to the magnetic rack for 1 minute. Transfer the eluted DNA to a new plate.

4| Run 10 µl on a QIAxcel (Qiagen) capillary electrophoresis instrument, in a 0.2 ml thin-walled 12-well strip tube with a QIAxcel DNA High Resolution Kit (Qiagen), QX Alignment Marker 15 bp-10 kb (Qiagen) and QX Size Marker 250 bp-8 kb (Qiagen), following manufacturer's instruction. Quantify by Qubit HS.

5| Gap repair. Perform the gap repair reaction as follows:

| Component | Volume (µl) |
| --- | --- |
| 2X Kapa HiFi HotStart Uracil + Ready Mix (Kapa) | 25 |
| Taq DNA ligase (40 U/µl) (NEB) | 2 |
| Purified Tagmented DNA (150-250 ng) | 23 |
| Total | 50 |

Incubate in a thermocycler at 72° C. for 30 minutes.

6| Dilute proteinase K 1:1 in water and add 5 µl of the diluted proteinase K to the tagmented DNA. Incubate at 55° C. for 15 minutes.

7| Purify the gap repair reactions as described in step 3 by adding 1.8× volumes (99 µl) of SPRI-Guanidine beads to the gap repaired-DNA. Elute in 40 µl of TE pH 8.0. Transfer the eluted DNA to a new plate.

8| USER/PNK

| Component | Volume (µl) |
| --- | --- |
| T4 DNA Ligase Buffer (10X) | 5 |
| USER Enzyme (1 U/µl) (NEB) | 3 |
| T4 Polynucleotide Kinase (10 U/µl) (NEB) | 2 |
| Gap-repaired DNA | 40 |
| Total | 50 |

Incubate in a thermocycler at 37° C. for 1 hour.

9| Add 1.8× volumes (90 µl) of SPRI beads to the USER/T4 PNK treated DNA, mix thoroughly by pipetting 10 times. Incubate at room temperature for 10 minutes. Place the reaction plate onto a Magnum FLX magnetic rack for 3 minutes. Remove the cleared solution from the reaction plate and discard. Add 200 µl of 80% ethanol, incubate for 30 seconds and remove the supernatant. Repeat this step for a total of two ethanol washes. Remove ethanol completely and let the samples air dry for 3 minutes on the magnetic rack. Remove the plate from the magnetic rack and add 35 µl of TE pH 8.0, and pipette 10 times to mix. Incubate at room temperature for 2 minutes. Place the reaction plate back to the magnetic rack for 1 minute. Transfer the supernatant to a new plate. Transfer the supernatant to a new plate. Pool and quantify by Qubit dsDNA HS assay (Thermo Fisher Scientific).

10| Intramolecular circularization

| Component | Volume (µl) |
| --- | --- |
| T4 DNA Ligase Buffer (10X) (NEB) | 10 |
| T4 DNA Ligase (400 U/µl) (NEB) | 2 |
| USER/PNK treated DNA (500 ng) | variable |
| $H_2O$ | variable |
| Total | 100 |

Incubate in a thermocycler at 16° C. for 16 hours.

11| Add 1× volumes (100 µl) of SPRI beads to the circularized DNA, mix thoroughly by pipetting 10 times. Incubate at room temperature for 10 minutes. Place the reaction plate onto a Magnum FLX magnetic rack for 3 minutes. Remove the cleared solution from the reaction plate and discard. Add 200 µl of 80% ethanol, incubate for 30 seconds and remove the supernatant. Repeat this step for a total of two ethanol washes. Remove ethanol completely and let the samples air dry for 3 minutes on the magnetic rack. Remove the plate from the magnetic rack and add 38 µl of TE pH 8.0, and pipette 10 times to mix. Incubate at room temperature for 2 minutes. Place the reaction plate back to the magnetic rack for 1 minute. Transfer the supernatant to a new plate.

12| Plasmid-Safe ATP-dependent DNase+Lambda exo/ExoI treatment

| Component | Volume (µl) |
| --- | --- |
| Exonuclease I Reaction Buffer (10×) (NEB) | 5 |
| ATP (25 mM) | 2 |
| Plasmid-Safe ATP-Dependent DNase (10 U/µl) (NEB) | 2 |
| Lambda Exonuclease (5 U/µl) (NEB) | 2 |
| Exonuclease I (*E. coli*) (20 U/µl) (NEB) | 1 |
| Circularized DNA | 38 |
| Total | 50 |

Incubate in a thermocycler at 37° C. for 1 h, 70° C. for 30 min, hold at 4° C.

13| Add 1× volumes (50 µl) of SPRI beads to the circularized DNA, mix thoroughly by pipetting 10 times. Incubate at room temperature for 10 minutes. Place the reaction plate onto a Magnum FLX magnetic rack for 3 minutes. Remove the cleared solution from the reaction plate and discard. Add 200 µl of 80% ethanol, incubate for 30 seconds and remove the supernatant. Repeat this step for a total of two ethanol washes. Remove ethanol completely and let the samples air dry for 3 minutes on the magnetic rack. Remove the plate from the magnetic rack and add 15 µl of TE pH 8.0, and pipette 10 times to mix. Incubate at room temperature for 2 minutes. Place the reaction plate back to the magnetic rack for 1 minute. Transfer the supernatant to a new plate, pool and quantify by Qubit HS (Thermo Fisher Scientific).

14| In vitro cleavage with Cas9 and sgRNA. Setup in vitro cleavage master-mix:

| Component | Volume (µl) |
| --- | --- |
| Cas9 Nuclease Reaction Buffer (10×) (NEB) | 5 |
| Cas9 Nuclease, S. pyogenes (1 µM) (NEB) | 4.5 |
| In vitro transcribed sgRNA (3 µM) | 1.5 |
| Total cleavage master-mix | 11 |

Incubate at room temperature for 10 min.
Add circularized DNA, diluted to a total volume of 39 µl:

| | |
| --- | --- |
| Cleavage master-mix (as described immediately above) | 11 |
| Plasmid-Safe DNase Treated DNA (125 ng) | 39 |
| Total | 50 |

Incubate in a thermocycler at 37° C. for 1 h, hold at 4° C.

15| Dilute proteinase K (NEB) 1:5 and then add 5 µl of the diluted proteinase K to the in vitro-cleaved DNA and incubate in a thermocycler at 37° C. for 15 min.

16| Add 1× volumes (55 µl) of SPRI beads to the circularized DNA, mix thoroughly by pipetting 10 times. Incubate at room temperature for 10 minutes. Place the reaction plate onto a Magnum FLX magnetic rack for 3 minutes. Remove the cleared solution from the reaction plate and discard. Add 200 µl of 80% ethanol, incubate for 30 seconds and remove the supernatant. Repeat this step for a total of two ethanol washes. Remove ethanol completely and let the samples air dry for 3 minutes on the magnetic rack. Remove the plate from the magnetic rack and add 42 µl of TE pH 8.0, and pipette 10 times to mix. Incubate at room temperature for 2 minutes. Place the reaction plate back to the magnetic rack for 1 minute. Keep the beads.

17| A-tailing. Setup the A-tailing master mix:

| Component | Volume (µl) |
| --- | --- |
| Kapa A-tailing Buffer (10×) (provided with Kapa HTP Library Preparation Kit PCR-free (96rxn), Kapa Biosystems) | 5 |
| Kapa A-tailing Enzyme (provided with Kapa HTP Library Preparation Kit PCR-free (96rxn), Kapa Biosystems) | 3 |
| Total A-tailing master-mix | 8 |

Add 8 µl of A-tailing master-mix to each eluted DNA sample with beads.

| | |
| --- | --- |
| A-tailing master-mix (prepared directly above) | 8 |
| Cleaved DNA/beads (from the previous step) | 42 |
| Total | 50 |

Incubate on a thermocycler at 30° C. for 30 min, hold at 4° C.

18| Add 1.8× volumes (90 µl) of PEG/NaCl SPRI solution (provided with Kapa HTP Library Preparation Kit PCR-free (96rxn), Kapa Biosystems) to the circularized DNA, mix thoroughly by pipetting 10 times. Incubate at room temperature for 10 minutes. Place the reaction plate onto a Magnum FLX magnetic rack for 3 minutes. Remove the cleared solution from the reaction plate and discard. Add 200 µl of 80% ethanol, incubate for 30 seconds and remove the supernatant. Repeat this step for a total of two ethanol washes. Remove ethanol completely and let the samples air dry for 3 minutes on the magnetic rack. Remove the plate from the magnetic rack and add 25 µl of TE pH 8.0, and pipette 10 times to mix. Incubate at room temperature for 2 minutes. Place the reaction plate back to the magnetic rack for 1 minute. Keep the beads.

19| Adapter ligation. Setup the adapter ligation master-mix:

| Component | Volume (µl) |
| --- | --- |
| Kapa Ligation Buffer (5×) (provided with Kapa HTP Library Preparation Kit PCR-free (96rxn), Kapa Biosystems) | 10 |
| Kapa DNA Ligase (provided with Kapa HTP Library Preparation Kit PCR-free (96rxn), Kapa Biosystems) | 5 |
| NEBNext Adapter for Illumina (15 µM) (provided with NEBNext ® Multiplex Oligos for Illumina ®, (Dual Index Primers Set 1), NEB)) | 2.5 |
| H$_2$O | 7.5 |
| Total master-mix | 25 |

Add 25 µl of adapter ligation master-mix to each A-tailed DNA sample with beads.

| | |
| --- | --- |
| Adapter ligation master-mix (described immediately above) | 25 |
| A-tailed DNA/beads (from the previous step) | 25 |
| Total | 50 |

Incubate on a thermocycler at 20° C. for 1 h, hold at 4° C.

20| Add 1× volumes (50 µl) of PEG/NaCl SPRI solution (provided with Kapa HTP Library Preparation Kit PCR-free (96rxn), Kapa Biosystems) to the adapter-ligated DNA and purify DNA as described in step 12. Elute in 47 µl of TE pH 8.0 and keep the beads.

21| USER enzyme. Add 3 µl of USER enzyme, provided with NEBNext® Multiplex Oligos for Illumina® (Dual Index Primers Set 1) (NEB) to the adapter ligated DNA with beads. Incubate at 37° C. for 15 min.

22| Add 0.7× volumes (35 µl) of PEG/NaCl SPRI (provided with Kapa HTP Library Preparation Kit PCR-free (96rxn), Kapa Biosystems) solution to the USER Enzyme treated DNA and purify as previously described in step 12. Elute in 20 µl of TE pH 8.0. Transfer the supernatant to a new semi-skirted PCR plate and quantify by Qubit dsDNA HS assay and proper Qubit assay tubes (usually about 2-5 ng/µl).

23| PCR. Setup a PCR master-mix for adding dual-index barcodes:

| Component | Volume (µl) | Final concentration |
|---|---|---|
| Nuclease-free water | 5 | |
| 2X Kapa HiFi HotStart Ready Mix (Kapa Biosystems) | 25 | 1X |
| Total master-mix | 30 | |
| Diluted PCR master-mix | 30 | |
| NEBNext i5 Primer (10 µM) (provided with NEBNext ® Multiplex Oligos for Illumina ®, (Dual Index Primers Set 1), NEB)) | 5 | 1 µM |
| NEBNext i7 Primer (10 µM) (provided with NEBNext ® Multiplex Oligos for Illumina ®, (Dual Index Primers Set 1), NEB)) | 5 | 1 µM |
| Total PCR mix | 40 | |

24| Add 40 µl of PCR master-mix to each sample of purified, USER enzyme treated DNA (~20 ng).

| Component | Volume (µl) | Final concentration |
|---|---|---|
| PCR mix | 40 | |
| USER enzyme treated DNA (~20 ng) | 10 | ~0.4 ng/µl |
| Total | 50 | |

25| Perform the PCR using the following thermocycling conditions.

| Step | Temperature | Time | Cycles |
|---|---|---|---|
| Denaturation | 98° C. | 45 s | 1 |
| Denaturation | 98° C. | 15 s | 20 |
| Annealing | 65° C. | 30 s | 20 |
| Extension | 72° C. | 30 s | 20 |
| Extension | 72° C. | 1 min | 1 |
| Hold | 4° C. | | 1 |

26| Purification Add 0.7× volumes (35 µl) of SPRI beads to the PCR and purify as previously described in step 12. Elute in 30 µl of TE pH 8.0. Transfer the supernatant to a new semi-skirted PCR plate and run 3 µl in QIAxcel (Qiagen).

27| Make 1:10 serial dilutions of 50 µl from $10^{-1}$ to $10^{-5}$ dilution of each sample from the library (PCR), starting with 5 µl of DNA and 45 µl of nuclease-free TE, and mix well.

28| Make qPCR master-mix solution as follows:

| Component | 1 reaction (µl) | Final Concentration |
|---|---|---|
| KAPA SYBR FAST qPCR Master Mix (2X) + Primer Premix (10X) (provided with Kapa Library Quantification Kit, Kapa Biosystems) | 12 | 1X |
| Nuclease-free water | 4 | |
| Total qPCR mix | 16 | |

29| Assay 2 different dilution factors (4 µl) for each sample ($10^{-4}$, and $10^{-5}$ from the library) in duplicate (in an appropriate 96-well plate). A standard curve (provided with Kapa Library Quantification Kit, Kapa Biosystems) and a non-template control (NTC) are required. Add 4 µl of each standard in duplicate, and nuclease-free water in the NTC. Add 16 µl of qPCR master-mix to each sample.

| Component | Volume (µl) | Final concentration |
|---|---|---|
| qPCR mix | 16 | |
| Sample (add nuclease-free water into the NTC well) | 4 | variable |
| Total | 20 | |

30| Seal the plate and spin down.

31| Run qPCR in appropriate thermocycler with the following program:

| Cycling step | Temperature | Time | Cycles |
|---|---|---|---|
| Initial denaturation | 95° C. | 5 min | 1 |
| Denaturation | 95° C. | 30 s | 35 |
| Annealing/extension/data acquisition | 60° C. | 45 sec | 35 |
| Melt curve analysis | 60-95° C. | | |

32| Add the appropriate DNA copies for each standard when setting up the qPCR plate in the qPCR program, as follows:

| Standard | dsDNA molecules/µl |
|---|---|
| Standard 1 | $1.2 \times 10^7$ |
| Standard 2 | $1.2 \times 10^6$ |
| Standard 3 | $1.2 \times 10^5$ |
| Standard 4 | $1.2 \times 10^4$ |
| Standard 5 | $1.2 \times 10^3$ |
| Standard 6 | $1.2 \times 10^2$ |

33| Analyze qPCR results. Multiply the average of duplicate values by the dilution factor and by the five-fold dilution factor of the qPCR reaction, as follows: Total copies/µl=#*dilution factor.

34| Pool library for MiSeq. Pool all the samples in one library at equimolar concentrations. 1× pooled library should be in a total volume of 5 µl, ~$1.2 \times 10^{10}$ molecules.

35| Denature the pooled library (~1.2×10¹⁰ molecules) by adding 5 µl of NaOH 0.2N and incubate at room temperature for 5 min. Then, add 940 µl of Hyb buffer (supplied with MiSeq® Reagent Kit v3 (600 cycle)) (Illumina).

36| Prepare the Phix control V3 (PhiX Control V3 KIT) (Illumina) as follows: mix 2 µl of 10 nM PhiX control with 3 µl of Tris-HCl 10 mM+0.1% Tween-20, denature with 5 µl of NaOH 0.2N and incubate at room temperature for 5 min. Add 990 µl of Hyb buffer, to generate 20 pM PhiX. Then, make a 12.5 pM PhiX dilution, by mixing 375 µl of the 20 pM PhiX with 225 µl of Hyb buffer. Add 100 µl of the 12.5 pM Phix to the denatured library.

37| Clean the Flow Cell (supplied with MiSeq® Reagent Kit v3 (600 cycle)) (Illumina) with ultra-pure water, dry with lens tissues, followed by cleaning with alcohol wipes and lens tissue.

38| Load and sequence library using a MiSeq 600-cycle v3 kit according to manufacturer's instructions using MiSeq system. Sequencing is performed with 150 bp paired-end reads and 8 bp dual-index reads.

39| After sequencing, copy the demultiplexed output FASTQ files to a location accessible to CIRCLE-seq/CHANGE-seq analysis pipeline.

Example 4. Individual-Specific CHANGE-seq Profiles

Figure 14A:
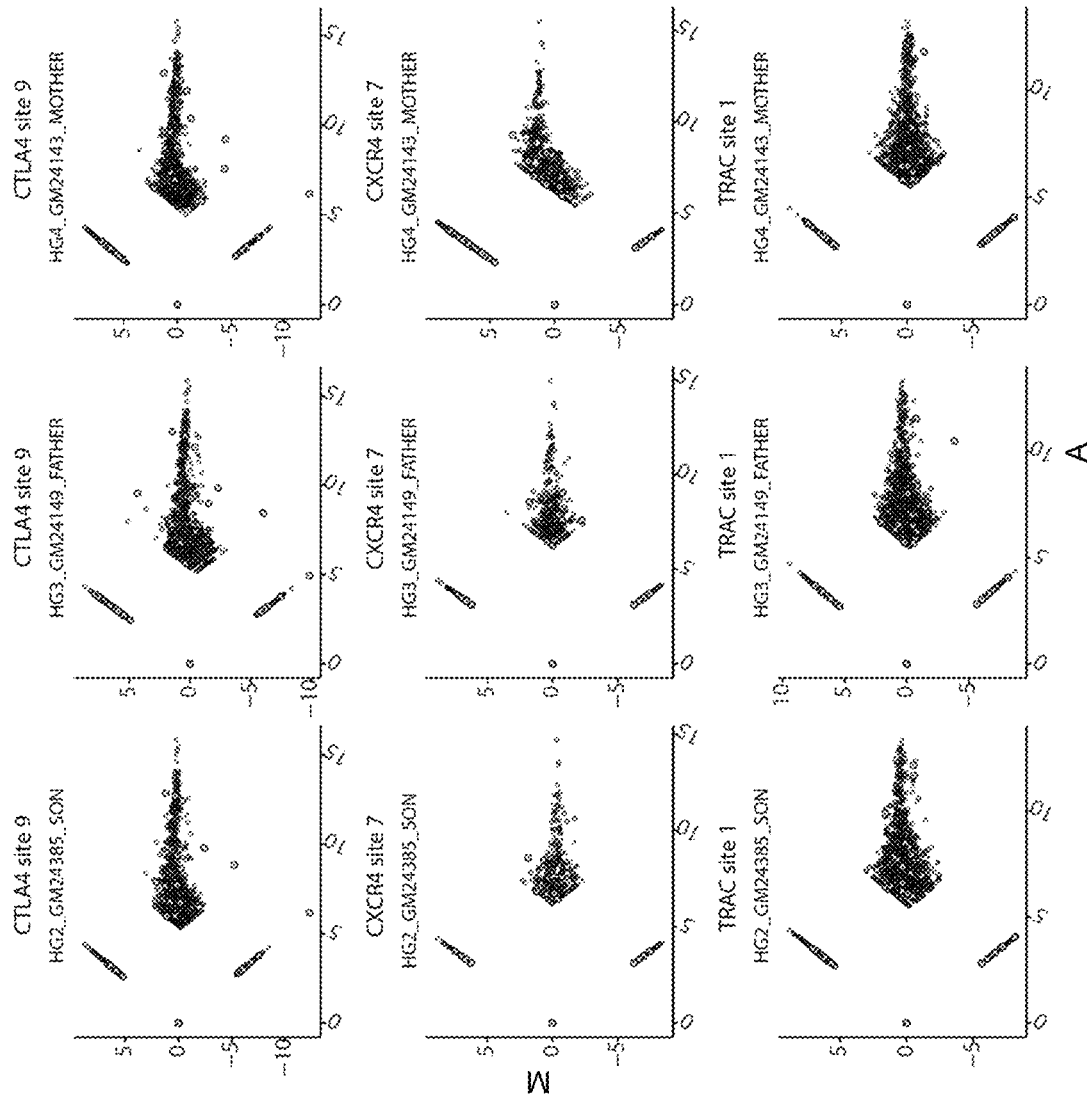
FIGS. 14A-14B. MA plot (ratio versus average) show pairwise comparisons of CHANGE-seq activity between 6 individuals and a reference. Each point represents an off-target site and those that contain a known single-nucleotide variant (SNV) that differs between the individual and reference are shown in bigger circles MA plots show clear outliers that indicate the effect of genetic variation on CHANGE-seq detected genome-wide activity.
Figure 14B:
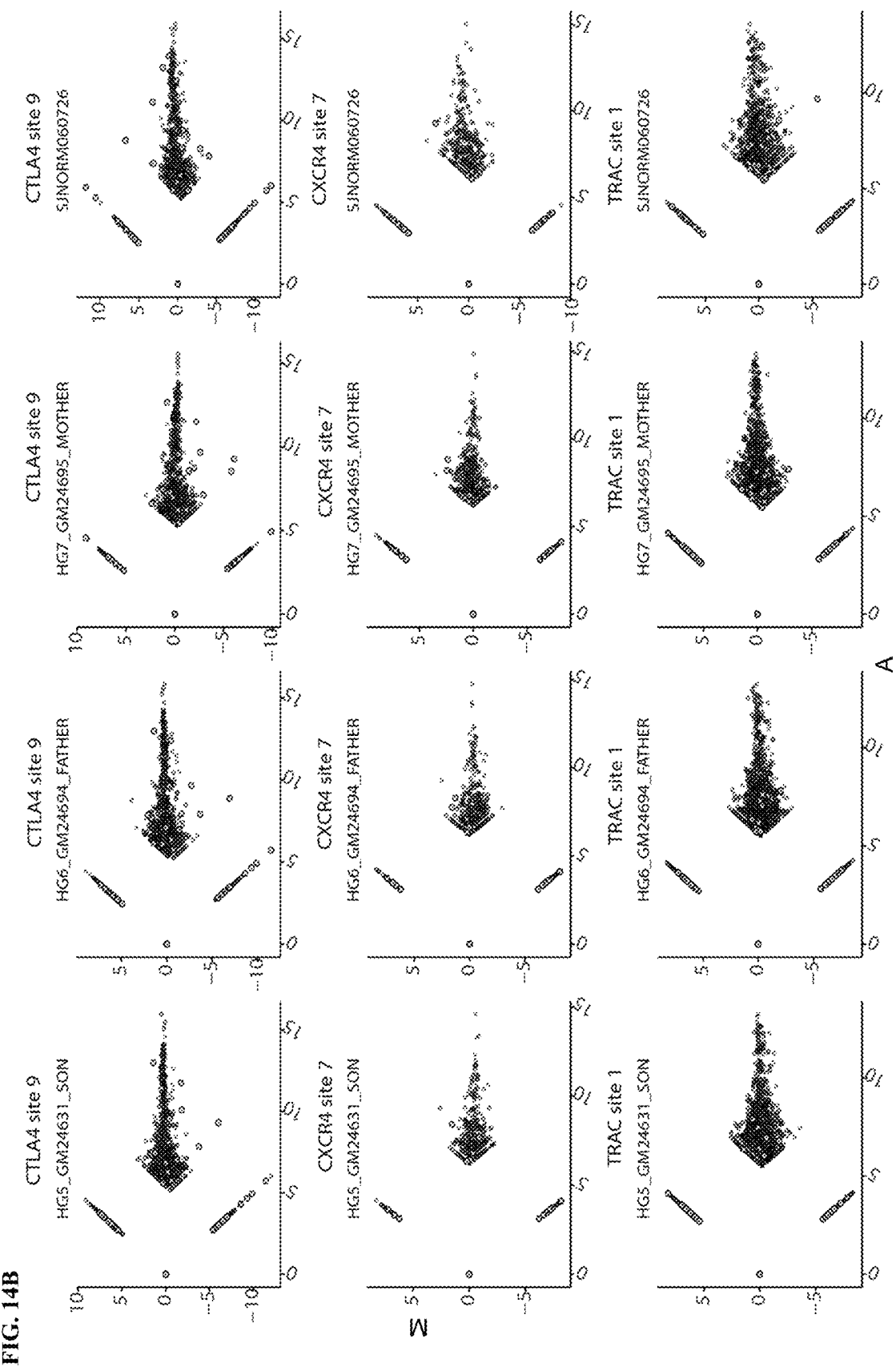

Genetic variation has the potential to affect genome editing activity. CHANGE-seq can be used to potentially detect the effects of human genetic variation on the genome-wide activity of CRISPR-Cas nucleases. The inventors performed CHANGE-seq in high-throughput on 7 well-characterized sources of genomic DNA (previously characterized by the National Institute of Standards and Technology Genome-in-a-bottle consortium) at 6 targets in duplicates (84 CHANGE-seq samples). They found that CHANGE-seq is sensitive to the effects of human genetic variation on in vitro activity of genome editing nucleases as measured by CHANGE-seq read counts. The results for three sites are shown in FIGS. 14A-14B. There are points that are clearly observable outside of the main grouping in the MA plots that correspond to off-target sites that contain non-reference human genetic variation.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method of preparing a library of covalently closed circular double-stranded DNA (dsDNA) molecules, the method comprising:
   (a) providing a sample comprising dsDNA;
   (b) performing a tagmentation of the dsDNA by incubating the dsDNA with a transposome complex comprising a transposase and a transposon DNA to add sequences that enable circularization;
   (c) gap-repairing single-stranded DNA (ssDNA) gaps in the DNA molecules generated in step (b);
   (d) treating the repaired dsDNA molecules to produce staggered DNA ends that can mediate intramolecular circularization;
   (e) incubating the DNA molecules obtained in step (d) with a ligase to induce intramolecular ligation; and
   (f) treating circularized DNA molecules obtained in step (e) with exonuclease(s) to degrade any remaining linear molecules with unligated ends and to produce a library of covalently closed circular dsDNA molecules.

2. The method of claim 1, wherein step (c) comprises treating the DNA molecules with an uracil-tolerant proofreading polymerase.

3. The method of claim 2, wherein step (c) comprises treating the DNA molecules with both the uracil-tolerant proofreading polymerase and a thermostable ligase.

4. The method of claim 3, wherein the thermostable ligase is Taq ligase.

5. The method of claim 1, wherein the transposon DNA includes a 4-8 base pair sequence for generating an overhang.

6. The method of claim 5, wherein one strand of the transposon DNA comprises an uracil base which can be excised by an uracil-specific excision reagent (USER) to generate an overhang.

7. The method of claim 5, wherein the transposon DNA comprises the sequence/5Phos/ACG/ideoxyU/AG-ATGTGTATAAGAGACAG (SEQ ID NO: 1) or the sequence/5Phos/CTGTCTCTTATACACATCTACGT (SEQ ID NO: 2), wherein/5Phos/indicates 5' phosphorylation and/ideoxyU/indicates internal deoxyuridine.

8. The method of claim 1, further comprising purifying the gap repaired DNA molecules between steps (c) and (d).

9. The method of claim 8, wherein the gap repaired DNA molecules are treated with a proteinase prior to purifying.

10. A method of detecting genome-wide activity of a genome editing enzyme, the method comprising:
    (g) contacting a library prepared according to the method of claim 1 with a genome editing enzyme to induce a site-specific cleavage;
    (h) preparing the cleaved fragments for end-ligation;
    (i) ligating a sequencing adapter at the cleavage site; and
    (j) sequencing the resulting fragments using primers that bind to the sequencing adapter.

11. The method of claim 10, wherein preparing the cleaved fragments for end-ligation in step (h) comprises A-tailing the dsDNA molecules to prevent dsDNA molecule concatemerization.

12. The method of claim 10, wherein preparing the cleaved fragments for end-ligation in step (h) comprises treating the cleaved fragments with a proteinase K.

13. The method of claim 10, wherein the genome editing enzyme is complexed with a specific guide RNA.

14. The method of claim 10, wherein the sequencing adapter of step (i) comprises a primer site compatible for use in PCR priming or sequencing.

15. The method of claim 14, wherein the sequencing adapter comprises a deoxyuridine and the method comprises contacting the library with one or more enzymes to nick at the deoxyuridine in the sequencing adapter between steps (i) and (j).

16. The method of claim 10, further comprising the steps of:
   using PCR amplification to enrich for adapter-ligated fragments and to add a full sequencing adapter; and
   sequencing those fragments bearing the full sequencing adapter.

17. The method of claim 10, wherein the genome editing enzyme is an enzyme that leaves staggered DNA ends, and the method further comprises an end-repair step after cleavage of the library of covalently closed circular dsDNA molecules in step (g).

18. The method of claim 17, wherein the genome editing enzyme is selected from Cas9, Cas12a (Cpf1), ZFNs, TALENs, meganucleases, megaTALs, and dimeric RNA-guided FokI-dCas9 nucleases.

19. The method of claim 10, wherein the genome editing enzyme is a base editor, and step (g) comprises (1) treating the library with the base editor and (2) treating the library with an additional enzyme to introduce a break at the site of a deaminated base.

20. The method of claim 19, wherein the base editor is a C>T base editor and the additional enzyme is an uracil-specific excision reagent.

21. The method of claim 19, wherein the base editor is an A>G base editor, and the additional enzyme is endonuclease V.

* * * * *

SEQUENCE LISTING

```
<160> NUMBER OF SEQ ID NOS: 186

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
acguagatgt gtataagaga cag                                             23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgtctctta tacacatcta cgt                                             23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 3
gtcagggttc tggatatctg ngg                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 4
gtcagggttc tggatatctg ngg                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 5
tccagggatc tggatatcag ngg                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 6
ctgagggttc tggatatctg nag                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 7
ttcaaggtta tggatatctg ngg                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 8
agtaggattc tagatatatg ngg                                           23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 9
gatcaggatc tggatatctg ngg                                           23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 10
gtcagaattc aggatatctg nga                                           23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 11
atcaggtatc aagatatctt ngg                                           23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 12
gccaaagttc tagatatctg ngg                                           23

```
<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 13
ttcaaggtac tagatatctt ngg                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 14
gccaggattc tagatgtctg ngg                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 15
ctcagggatc tggatacctg ngg                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 16
gtcagcattc tggatacctg ngg                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 17
gtcaggcctc tggataactg ngg                                          23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 18
gtcaaggtac ttaatatctg ngg                                          23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 19
gtgagtagag cggaggcagg ngg                                          23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 20
gtgagtagag cggaggcagg ngg                                          23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 21
ttgagtaggc agaggcaggn gg                                           22

<210> SEQ ID NO 22
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 22
ataagtagaa aggagacagg ngg                                           23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 23
aagagtaggg cagaggcagg nag                                           23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 24
gaaagtagag cgaaggcaga nag                                           23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 25
gtgtgtagag gagaggcagg ngg                                           23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 26
atgaatagag caggggcagg ngg                                           23

```
<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 27
gagagtagag agaaggcaga ngg                                           23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 28
atgagtagaa caaaggcagt ngg                                           23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 29
ggcggtagag aggaggcagt ngg                                           23

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 30
gtgagagaga ggaagcaggn gg                                            22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
```

<223> OTHER INFORMATION: a, c, t, g, unknown or other

<400> SEQUENCE: 31
gtgcatagag cgaaggaagg ngg                                           23

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 32
gtgagagaga gaaggcaggn ag                                            22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 33
gagagtagag aggagactgg ngg                                           23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 34
gagagagaga ggagacaggn gg                                            22

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 35
gagtccgagc agaagaagaa ngg                                           23

<210> SEQ ID NO 36
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 36
gagtccgagc agaagaagaa ngg                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 37
aaggccaagc agaagagtaa ngg                                              23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 38
gaggccgagc agaagaaaga ngg                                              23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 39
gagtcctagc aggagaagaa nag                                              23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 40
tcatccaagc agaagaagaa nag                                              23
```

```
<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 41
gagtctaagc agaagaagaa nag                                              23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 42
gaatccaagc aggagaagaa nga                                              23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 43
gagtaagaga agaagaagaa ngg                                              23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 44
gagttagagc agaagaagaa ngg                                              23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (21)..(21)
<223> OTHER INFORMATION: a, c, t, g, unknown or other

<400> SEQUENCE: 45
cactccaagt agaagaagaa nag                                              23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 46
gagtctaagc aggagaataa ngg                                              23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 47
aagtctgagc acaagaagaa ngg                                              23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 48
gagcctgagc agaaggagaa ngg                                              23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 49
aagcccgagc aaaggaagaa ngg                                              23

<210> SEQ ID NO 50
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 50
gagtcccagc aaaagaagaa nag                                              23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 51
cagtctgagt agaagaaaaa ngg                                              23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 52
gagtacaagc agatgaaaaa ngg                                              23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 53
ttctccaagc agaagaagaa nag                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 54
gaatccaagc agaagaagag nag                                        23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 55
gagcacgagc aagagaagaa ngg                                        23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 56 gggtggggggg agtttgctcc ngg                                       23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 57
ggatggaggg agtttgctcc ngg                                        23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 58
tagtggaggg agcttgctcc ngg                                        23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (21)..(21)
<223> OTHER INFORMATION: a, c, t, g, unknown or other

<400> SEQUENCE: 59
gggtgggggg agtttgctcc ngg                                              23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 60
ctggtggggg agcttgctcc ngg                                              23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 61 gcgtggggggg tgtttgctcc ngg                                             23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 62
cgggggaggg agtttgctcc ngg                                              23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 63
agggaggagg aatttgctcc ngg                                              23

<210> SEQ ID NO 64
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 64 ggggaggggga agtttgctcc ngg                                              23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 65
aagtaaggga agtttgctcc ngg                                               23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 66
agggagggag aatttgctcc ngg                                               23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 67
gggagggtgg agtttgctcc ngg                                               23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 68
```

-continued

```
gaggggagc agtttgctcc ngg                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 69
aggtggtggg agcttgttcc ngg                                             23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 70
atgtgtgggg aatttgctcc ngg                                             23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 71
gagggtgggg agtttactcc ngg                                             23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 72
acggtggggg aatttgctcc nga                                             23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (21)..(21)
<223> OTHER INFORMATION: a, c, t, g, unknown or other

<400> SEQUENCE: 73 ttggggggc agtttgctcc ngg                                             23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 74
agtttggggg agtttgcccc ngg                                            23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 75
aggaggggga agaatgctcc ngg                                            23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 76
ggtgggggtg ggtttgctcc ngg                                            23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 77
gagtccgagc agaagaagaa ngg                                            23

<210> SEQ ID NO 78
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 78
gagtccgagc agaagaagaa ngg                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 79
aaggccaagc agaagagtaa ngg                                              23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 80
gagtcctagc aggagaagaa nag                                              23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 81
gaggccgagc agaagaaaga ngg                                              23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 82
gaatccaagc aggagaagaa nga                                          23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 83
tcatccaagc agaagaagaa nag                                          23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 84
gagtctaagc aggagaataa ngg                                          23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 85
aagtccgagg agaggaagaa ngg                                          23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 86
gaagtagagc agaagaagaa ncg                                          23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 87
gagcctgagc agaaggagaa ngg                                            23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 88
aagcccgagc aaaggaagaa ngg                                            23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 89
aagtccatgc agaagaggaa ngg                                            23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 90
gagttagagc agaagaagaa ngg                                            23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 91
tcttccaagc agaggaagaa ngg                                            23
```

```
<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 92
gagtacaagc agatgaaaaa ngg                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 93
gaggccaagc agaaaaaaaa ngg                                           23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 94
gaagtagagc agaagaagaa ncg                                           23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 95
aagtccagac agaagaagaa nga                                           23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

<400> SEQUENCE: 96
aaatccaacc agaagaagaa ngg                                    23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 97
gagtctaagc agaagaagaa nag                                    23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 98
gaggccaagc agaaagaaaa ngg                                    23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 99
aggtcagagc agaagaaaag ngg                                    23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 100
gagtcccagc aaaagaagaa nag                                    23

<210> SEQ ID NO 101
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 101
cactccaagt agaagaagaa nag                                              23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 102
atgtccaagc agaagaagtc ngg                                              23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 103
aaggcagagc agaggaagag ngg                                              23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 104
aagtcccggc agaggaagaa ngg                                              23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 105
gaagtagagc agaagaagaa ncg                                              23
```

```
<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 106
ttctccaagc agaagaagaa nag                                            23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 107
gagtccaagc agtagaggaa ngg                                            23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 108
gagttagagc agaaaaaaaa ngg                                            23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 109
gaatccaagc agaagaagag nag                                            23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
```

<223> OTHER INFORMATION: a, c, t, g, unknown or other

<400> SEQUENCE: 110
agttccaagc agaggaagaa ngg                                               23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 111
gagcacgagc aagagaagaa ngg                                               23

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 112
aagtcagaga gaagaagaan ag                                                22

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 113
gagtccgagc agaagaagaa ngg                                               23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 114
gagtccgagc agaagaagaa ngg                                               23

<210> SEQ ID NO 115
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 115
gaggccgagc agaagaaaga ngg                                            23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 116
gaatccaagc agaagaagag nag                                            23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 117
aagtccatgc agaagaggaa ngg                                            23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 118
tcttccaagc agaggaagaa ngg                                            23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 119
gagcctgagc agaaggagaa ngg                                            23
```

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 120
aagtctgagc acaagaagaa ngg                                          23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 121
aaatccaacc agaagaagaa ngg                                          23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 122
gagtaagaga agaagaagaa ngg                                          23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 123
gagtcctagc aggagaagaa nag                                          23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 124
aagtcccggc agaggaagaa ngg                                         23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 125
gagtccaagc agtagaggaa ngg                                         23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 126
aagtccagac agaagaagaa nga                                         23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 127
acgtctgagc agaagaagaa ngg                                         23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 128
aaggccaagc agaagagtaa ngg                                         23

<210> SEQ ID NO 129
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 129
gagtacaagc agatgaaaaa ngg                                          23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 130
gagcacgagc aagagaagaa ngg                                          23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 131
atgtccaagc agaagaagtc ngg                                          23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 132
gagaaagagc agaggaagaa ngg                                          23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 133
```
aagcccgagc aaaggaagaa ngg                                          23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 134
aaatctgagc agaaaagaa nga                                           23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 135
gagcaggagc aagagaacaa ngg                                          23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 136
gagtcccagc aaaagaagaa nag                                          23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 137
agttccaagc agaggaagaa ngg                                          23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (21)..(21)
<223> OTHER INFORMATION: a, c, t, g, unknown or other

<400> SEQUENCE: 138
gaggccttgc agaagaagaa ngc                                             23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 139
aaggccgagc aggaggaaga ngg                                             23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 140
ggatgagagt agaagaagga ngg                                             23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 141
gagtttgagt agaagaagaa nag                                             23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 142
aagtccgagg agaggaagaa ngg                                             23

<210> SEQ ID NO 143
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 143
aggtccgatc agtaaaaaaa ngg                                         23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 144
tattcagagc tgaagaagaa ngg                                         23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 145
gaggaggaga agaagaagaa nga                                         23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 146
gagagagaga aggagaagaa nga                                         23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 147
```
tagtgttagc aaaagaagaa nag                                     23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 148
aagttggagc aggagaagaa ngg                                     23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 149
tcatccaagc agaagaagaa nag                                     23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 150
gagtccgagc agaagaagaa ngg                                     23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 151
gagtccgagc agaagaagaa ngg                                     23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (21)..(21)
<223> OTHER INFORMATION: a, c, t, g, unknown or other

<400> SEQUENCE: 152
gaggccgagc agaagaaaga ngg                                                 23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 153
aaggccaagc agaagagtaa ngg                                                 23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 154
gagtctaagc agaagaagaa nag                                                 23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 155
tcatccaagc agaagaagaa nag                                                 23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 156
gagtcctagc aggagaagaa nag                                                 23

<210> SEQ ID NO 157
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 157
gagttagagc agaagaagaa ngg                                              23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 158
gaatccaagc agaagaagag nag                                              23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 159
gagtctaagc aggagaataa ngg                                              23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 160
gaatccaagc aggagaagaa nga                                              23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

<400> SEQUENCE: 161
cactccaagt agaagaagaa nag                                              23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 162
aagtctgagc acaagaagaa ngg                                              23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 163
aagcccgagc aaaggaagaa ngg                                              23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 164
aagtccgagg agaggaagaa ngg                                              23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 165
gagtacaagc agatgaaaaa ngg                                              23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic

```
                                  oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 166
cagtctgagt agaagaaaaa ngg                                            23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 167
aagtccagac agaagaagaa nga                                            23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 168
agttccaagc agaggaagaa ngg                                            23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 169
gagcctgagc agaaggagaa ngg                                            23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 170
gagtcccagc aaaagaagaa nag                                            23
```

-continued

```
<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 171
gaagtagagc agaagaagaa ncg                                              23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 172
gagcacgagc aagagaagaa ngg                                              23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 173
gagtaagaga agaagaagaa ngg                                              23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 174
aagtccatgc agaagaggaa ngg                                              23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 175
gagtccaagc agtagaggaa ngg                                              23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 176
ttctccaagc agaagaagaa nag                                              23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 177
aagtcccggc agaggaagaa ngg                                              23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 178
gagtttgagt agaagaagaa nag                                              23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 179
gagcccaagc acaaaaagaa ngg                                              23

<210> SEQ ID NO 180
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 180
gagccggagc agaagaagga ngg                                              23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 181
gaagtagagc agaagaagaa ncg                                              23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 182
gaggccaagc agaaaaaaaa ngg                                              23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 183
acgtctgagc agaagaagaa ngg                                              23

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 184
aagtcagaga gaagaagaan ag                                               22

```
<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 185
aagtccaggc aggagaaaaa ngg                                            23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 186
aagtctgagt aggagaaaaa ngg                                            23
```